United States Patent
Deslattes Mays et al.

(10) Patent No.: US 10,308,952 B2
(45) Date of Patent: Jun. 4, 2019

(54) DROUGHT RESISTANCE IN PLANTS: UPL4

(71) Applicant: Keygene N.V., Wageningen (NL)

(72) Inventors: Anne Deslattes Mays, Wageningen (NL); Marieke Helena Adriana Van Hulten, Wageningen (NL); Shital Anilkumar Dixit, Wageningen (NL); Martin De Vos, Wageningen (NL); Jesse David Munkvold, Rockville, MD (US); Matthew Vitabile Dileo, Silver Spring, MD (US)

(73) Assignee: KEYGENE N.V., Wageningen (NL)

(*) Notice: Subject to any disclaimer, the term of this patent is extended or adjusted under 35 U.S.C. 154(b) by 533 days.

(21) Appl. No.: 14/377,842

(22) PCT Filed: Feb. 18, 2013

(86) PCT No.: PCT/NL2013/050100
§ 371 (c)(1),
(2) Date: Aug. 8, 2014

(87) PCT Pub. No.: WO2013/122471
PCT Pub. Date: Aug. 22, 2013

(65) Prior Publication Data
US 2016/0010106 A1 Jan. 14, 2016

Related U.S. Application Data

(60) Provisional application No. 61/599,963, filed on Feb. 17, 2012.

(51) Int. Cl.
*A01H 1/06* (2006.01)
*C12N 15/82* (2006.01)

(52) U.S. Cl.
CPC ................. *C12N 15/8273* (2013.01)

(58) Field of Classification Search
None
See application file for complete search history.

(56) References Cited

U.S. PATENT DOCUMENTS

| | | | |
|---|---|---|---|
| 7,435,874 B2 | 10/2008 | Gebhardt | |
| 2004/0031072 A1 | 2/2004 | La Rosa et al. | |
| 2004/0123343 A1 | 6/2004 | La Rosa et al. | |
| 2006/0150283 A1 | 7/2006 | Alexandrov et al. | |
| 2007/0266453 A1 | 11/2007 | Anderson | |
| 2009/0094717 A1 | 4/2009 | Troukhan et al. | |
| 2009/0144850 A1 | 6/2009 | Van Winkle | |
| 2010/0212050 A1 | 8/2010 | Shoseyov et al. | |
| 2012/0260373 A1 | 10/2012 | Nestor | |

FOREIGN PATENT DOCUMENTS

| EP | 1 685 242 B1 | 8/2006 |
|---|---|---|
| JP | 2015-508649 A | 3/2015 |
| JP | 2015-508650 A | 3/2015 |
| WO | WO-02/083911 A1 | 10/2002 |
| WO | WO-03/020015 A2 | 3/2003 |
| WO | WO-2004/035798 A2 | 4/2004 |
| WO | WO-2011/038389 A2 | 3/2011 |

OTHER PUBLICATIONS

Genbank Accession NP_195908.1, first avaiable online Aug. 21, 2001.*
Gul et al (Cell. Mol. Life Sci. (2017) 74:525-541).*
Coates et al (Plant Growth Signaling, vol. 10 of the series Plant Cell Monographs pp. 299-314, published on Jul. 28, 2007).*
Mudgil et al (Plant Physiology, Jan. 2004, vol. 134, pp. 59-66).*
Rotin et al (Nature Reviews Molecular Cell Biology 10, 398-409 (Jun. 2009).*
Downes et al (The Plant Journal (2003) 35, 729-742).*
NCBI Reference Sequence: NM_120366.4 (2017).*
NCBI Reference Sequence NM_120366.4 with alignment (2017).*
TAIR Accession Locus: AT5G02880 (2017).*
Downes et al (The Plant Journal (2003) 35: 729-742) (Year: 2003).*
Gul et al (Cell. Mol. Life Sci. (2017) 74:525-541) (Year: 2017).*
Rotin et al (Nature Reviews Molecular Cell Biology 10, 398-409 (Jun. 2009) (Year: 2009).*
Mudgil et al (Plant Physiology, Jan. 2004, vol. 134, pp. 59-66) (Year: 2004).*
Coates et al (Plant Growth Signaling, vol. 10 of the series Plant Cell Monographs pp. 299-314, published on Jul. 28, 2007) (Year: 2007).*
ABRC. Germplasm SALK_ 136556.27.x. Published Mar. 3, 2003. pp. 1-2.
ABRC. Germplasm SALK_136556C. Published Apr. 12, 2007, pp. 1-2.
An et al. Pepper pectin methylesterase inhibitor protein CaPMEI1 is required for antifungal activity, basal disease resistance and abiotic stress tolerance. Planta., 2008., vol. 228, pp. 61-78.
Chang et al. Papaya pectinesterase inhibition by sucrose. 24th Annual Meeting of the Institute of Food Technologies. May 24-28, 1964. pp. 218-222.
ExplorEnz. EC 3.1.1.11. Pectinesterase. 2001,. 1 pg.
Gray et al. The use of transgenic and naturally occurring mutants to understand and manipulate tomato fruit ripening. Plant, Cell and Environment. 1994. 17:557-571.
Hong et al., "Functional characterization of pectin methylesterase inhibitor (PMEI) in wheat", Genes Genet. Syst, 2010, vol. 85, pp. 97-106.
"*Arabidopsis thaliana* pectinesterase (AT5G19730)mRNA, complete cds", GenBank Database,Accession No. NM_121978.
Hall et al., "Antisense inhibition of pectin esterase gene expression in transgenic tomatoes", The Plant Journal, 1993, vol. 3, No. 1, pp. 121-129.

(Continued)

*Primary Examiner* — Lee A Visone
(74) *Attorney, Agent, or Firm* — Foley & Lardner LLP

(57) ABSTRACT

The present invention relates to a new method for increasing drought resistance of a plant. The method encompasses the impairment of the expression of a gene or genes in said plant. In comparison to a plant not manipulated to impair the expression of said gene(s), the plants display improved drought resistance. Also provided are plants and plant product that can be obtained by the method according to the invention.

8 Claims, 4 Drawing Sheets

Specification includes a Sequence Listing.

(56) References Cited

OTHER PUBLICATIONS

Aharoni, et al. "The SHINE Clade of AP2 Domain Transcription Factors Activates Wax Biosynthesis, Alters Cuticle Properties, and Confers Drought Tolerance when Overexpressed in *Arabidopsis*", The Plant Cell, Sep. 2004, vol. 16, pp. 2463-2480.
Bray, "Plant responses to water deficit", Trends in Plant Science, Feb. 1997, vol. 2, No. 2, pp. 48-54.
Cho, et al. "ROS-Mediated ABA Signaling", J. Plant Biol., 2009, vol. 52, pp. 102-113.
Denby, et al. "Engineering drought and salinity tolerance in plants: lessons from genome-wide expression profiling in *Arabidopsis*", Trends in Biotechnology, Nov. 2005, vol. 23, No. 11, pp. 547-552.
Devereux, J., et al., A comprehensive set of sequence analysis programs for the VAX, Nucleic Acids Research, 1984, vol. 12, Issue 1, pp. 387-395.
Harb, et al. "Molecular and Physiological Analysis of Drought Stress in *Arabidopsis* Reveals Early Responses Leading to Acclimation in Plant Growth", Plant Physiology, Nov. 2010, vol. 154, pp. 1254-1271.
Karaba, et al. "Improvement of water use efficiency in rice by expression of HARDY, an *Arabidopsis* drought and salt tolerance gene", PNAS, Sep. 2007, vol. 104, No. 39, pp. 15270-1575.
Kasuga et al., "Improving Plant Drought, Salt, and Freezing Tolerance by Gene Transfer of a Single Stress-inducible Transcription Factor," Nature Biotechnology, vol. 17, pp. 287-291 (1999).
Kilian, et al. "The AtGenExpress global stress expression data set: protocols, evaluation and model data analysis of UV-B light, drought and cold stress responses", The Plant Journal, 2007, vol. 50, pp. 347-363.
Kwak, et al. "NADPH oxidase AtrbohD and AtrbohF genes function in ROS-dependent ABA signaling in *Arabidopsis*", The EMBO Journal, 2003, vol. 22, No. 11, pp. 2623-2633.
Kwak, et al. "The Clickable Guard Cell, Version II: Interactive Model of Guard Cell Signal Transduction Mechanisms and Pathways", *Arabidopsis* Book, 2008, vol. 6, e0114, 16 pgs.
Kwak, et al. "The Role of Reactive Oxygen Species in Hormonal Responses", Plant Physiology, Jun. 2006, vol. 141, pp. 323-329.
Lee, et al. "Activation of Glucosidase via Stress-Induced Polymerization Rapidly Increases Active Pools of Abscisic Acid", Cell, Sep. 2006, vol. 126, pp. 1109-1120.
Pennisi, "The Blue Revolution, Drop by Drop, Gene by Gene", Science, Apr. 2008, vol. 320, pp. 171-173.
Serrano, et al. "A glimpse of the mechanisms of ion homeostasis during salt stress", Journal of Experimental Botany, Jun. 1999, vol. 50, Special Issue, pp. 1023-1036.
Sinaki, et al. "The Effects of Water Deficit During Growth Stages of Canola (*Brassica napus* L.)", American-Eurasian J. Agric. & Environ. Sci, 2007, vol. 2, No. 4, pp. 417-422.
Snow, et al. "Evaluation of a System for the Imposition of Plant Water Stress", Plant Physiol, 1985, vol. 77, pp. 602-607.
Swindell, "The Association Among Gene Expression Responses to Nine Abiotic Stress Treatments in *Arabidopsis thaliana*", Genetics, Dec. 2006, vol. 1811-1824.
Wang, et al. "Plant responses to drought, salinity and extreme temperatures: towards genetic engineering for stress tolerance", Planta, 2003, vol. 218, pp. 1-14.
Alonso, et al. "Genome-Wide Insertional Mutagenesis of *Arabidopsis thaliana*", Science, Aug. 1, 2003, vol. 301, pp. 653-657.
Cho, et al. "*Arabidopsis* PUB22 and PUB23 Are Homologous U-Box E3 Ubiquitin Ligases That Play Combinatory Roles in Response to Drought Stress", The Plant Cell, Jul. 2008, vol. 20, pp. 1899-1914.
Downes, et al. "The HECT ubiquitin-protein ligase (UPL) family in *Arabidopsis*: UPL3 has a specific role in trichome development", The Plant Journal, 2003, vol. 35, pp. 729-742.
International Search Report in PCT/NL2013/050100 dated Jun. 10, 2013.
International Search Report in PCT/NL2013/050101 dated Jun. 10, 2013.
International Search Report in PCT/NL2013/050102 dated Jun. 12, 2013.
Louvet, et al. "Comprehensive expression profiling of the pectin methylesterase gene family during silique development in *Arabidopsis thaliana*", Planta, 2006, vol. 226, pp. 782-791.
Paterson, et al. "The Sorghum bicolor genome and the diversification of grasses", Nature, Jan. 2009, vol. 457, pp. 551-556.
Qin, et al. "*Arabidopsis* DREB2A-Interacting Proteins Function as Ring E3 Ligases and Negatively Regulate Plant Drought Stress-Responsive Gene Expression", The Plant Cell, Jun. 2008, vol. 20, pp. 1693-1707.
Retrieved from EBI accession No. UNIPROT:C5Z1DO, Sep. 1, 2009, "RecName: Full=Pectinesterase; EC=3.1.1.11;".
Retrieved from EBI accession No. UNIPROT:Q8VYZ3, Mar. 1, 2002, "RecName: Full=Probable pectinesterase 53; Short=PE 53; EC=3.1.1.11; AltName: Full=Pectin methylesterase 53; short-AtPME53; Flags: Precursor;".
Coates et al., "Armadillo repeat proteins: versatile regulators of plant development and signaling", Plant Cell Monographs, 2007, vol. 10. pp. 299-314.
Gul et al., "Metozoan evolution of the armadillo repeat superfamily", Cell. Mol. Life Sci., 2017, vol. 74, pp. 525-541.
Mudgil et al., "A large complement of the predicted *Arabidopsis* ARM repeat proteins are members of the U-Box E3 ubiquitin ligase family", Plant Physiology, Jan. 2004, vol. 134, pp. 59-66.
Notice of Reasons for Rejection issued in co-pending Japanese Application No. 2014-557587, dated Jan. 31, 2017, with English translation.
Notice of Reasons for Rejection issued in co-pending Japanese Application No. 2014-557588, dated Jan. 31, 2017, with English translation.
Rotin et al., "Physiological functions of the HECT family of ubiquitin ligases", Nature Reviews Molecular Cell Biology, 2009, vol. 10, pp. 398-409.
Brenner, "Errors in genome annotation", TIG, 1999, vol. 15, No. 4, pp. 132-133.
Lionetti et al., "Engineering the cell wall by reducing de-methylesterified homogalacturonan improves saccharification of plants tissues for bioconversion", PNAS, Jan. 12, 2010, vol. 107, No. 2, pp. 616-621.
Qu et al, "Brassinosteroids regulate pectin methylesterase activity and AtPME41 expression in *Arabidopsis* under chilling stress", Cryobiology, 2011, vol. 63, pp. 111-117.
Szymanski, "Chapter 22: The role of actin during *Arabidopsis* Trichome morphogenesis", Actin: A Dynamic Framework for Multiple Plant Cell Functions, Springer-Science Business Media, B.V., 2000, 20 pages.
Barbagallo, et al. "Pectin methylesterase, polyphenol oxidase and physicochemical properties of typical long-storage cherry tomatoes cultivated under water stress regime", Journal of Science of food and Agriculture (2008) vol. 88, pp. 389-396.
Camacho-Cristobal, et al. "The expression of several cell wall-related genes in *Arabidopsis* roots is down-regulated under boron deficiency" Environmental and Experimental Botany (2008) vol. 63, pp. 351-358.
El Refy, et al. "The *Arabidopsis* KAKTUS gene encodes a HECT protein and controls the number of endoreduplication cycles", Mol Gen Genomics (2003), vol. 270, pp. 403-414.
Fagard, et al. "Cell wall mutants" Plant Physiology and Biochemistry (Jan. 2000) vol. 38,(1/2), pp. 15-25.
Hyun An, et al. "Pepper pectin methylesterase inhibitor protein CaPMEI1 is required for antifungal activity, basal disease resistance and abiotic stress tolerance", Planta (2008) vol. 228, pp. 61-78.
International Search Report & Written Opinion in NL Appln No. 2006007 dated Aug. 18, 2011.
Perazza, et al. "Trichome Cell Growth in *Arabidopsis thaliana* Can Be Depressed by Mutations in at Least Five Genes", Genetics (May 1999), vol. 152, pp. 461-476.
Search Report in NL Appln No. 2006006 dated Aug. 17, 2011.

(56) References Cited

OTHER PUBLICATIONS

Seymour, et al. "Down-regulation of two non-homologous endogenous tomato genes with a single chimaeric sense gene construct", Database Accession No. PREV199497005095 (1993).
Speulman, et al. "Target selected insertional mutagenesis on chromosome IV of *Arabidopsis* using the En-I transposon system", Journal of Biotechnology (2000), vol. 78, pbs 301-312.
Tian, et al. "Pollen-specific pectin methylesterase involved in pollen tube growth", Developmental Biology (2006) vol. 294, pp. 83-91.
Yamada, et al. "*Arabidopsis thaliana* putative pectin methylesterase (At5g19730) mRNA, complete cds", Database acession No. AY065431 (Dec. 13, 2001).
Zhi-Biao, et al. "Analysis of two antisense transgenes inhibiting expression of their endogenous genes in transgenic tomatoes", Database Accession No. PREV199699184897 (1996).

* cited by examiner

DROUGHT RESISTANCE IN PLANTS: UPL4

CROSS REFERENCE TO RELATED APPLICATIONS

The present application is a National Stage of International Application No. PCT/NL2013/050100 filed on Feb. 18, 2013, which claims the benefit of U.S. Application No. 61/599,963 filed on Feb. 17, 2012, the entire disclosures of which are incorporated herein by reference.

TECHNICAL FIELD

The present invention relates to a method for increasing drought resistance of a plant. The method encompasses the impairment of the expression of a gene or genes or a protein in said plant. In comparison to a plant not manipulated to impair the expression of said gene(s) or protein(s), the plants display improved drought resistance. Also provided are plants and plant product that can be obtained by the method according to the invention.

BACKGROUND OF THE INVENTION

Abiotic stresses, such as drought, salinity, extreme temperatures, chemical toxicity and oxidative stress are threats to agriculture and it is the primary cause of crop loss worldwide (Wang et al. (2003) Planta 218(1) 1-14).

In the art, several reports are available dealing with the biochemical, molecular and genetic background of abiotic stress (Wang et al. (2003) Planta 218(1) 1-14 or Kilian et al (2007) Plant J 50(2) 347-363). Plant modification to deal with abiotic stress is often based on manipulation of genes that protect and maintain the function and structure of cellular components. However, due to the genetically complex responses to abiotic stress conditions, such plants appear to be more difficult to control and engineer. Wang, (Wang et al. (2003) Planta 218(1) 1-14), inter alia, mentions that one of the strategies of engineering relies on the use of one or several genes that are either involved in signalling and regulatory pathways, or that encode enzymes present in pathways leading to the synthesis of functional and structural protectants, such as osmolytes and antioxidants, or that encode stress-tolerance-conferring proteins.

Although improvements in providing abiotic stress tolerant plants have been reported, the nature of the genetically complex mechanisms underlying it provides a constant need for further improvement in this field. For example, it has been reported that genetically transformed drought tolerant plants generally may exhibit slower growth and reduced biomass (Serrano et al (1999) J Exp Bot 50:1023-1036) due to an imbalance in development and physiology, thus having significant fitness cost in comparison with plants that are not transformed (Kasuga et al. (1999) Nature Biot. Vol. 17; Danby and Gehring (2005) Trends in Biot. Vol. 23 No. 11).

Several biotechnological approaches are proposed in order to obtain plants growing under stress conditions. Plants with increased resistance to salt stress are for example disclosed in WO03/020015. This document discloses transgenic plants that are resistant to salt stress by utilizing 9-cis-epoxycarotenoid dioxygenase nucleic acids and polypeptides.

Plants with increased drought tolerance are disclosed in, for example, US 2009/0144850, US 2007/0266453, and WO 2002/083911. US2009/0144850 describes a plant displaying a drought tolerance phenotype due to altered expression of a DR02 nucleic acid. US 2007/0266453 describes a plant displaying a drought tolerance phenotype due to altered expression of a DR03 nucleic acid and WO 2002/083911 describes a plant having an increased tolerance to drought stress due to a reduced activity of an ABC transporter which is expressed in guard cells. Another example is the work by Kasuga and co-authors (1999), who describe that overexpression of cDNA encoding DREB1A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291). There remains a need for new, alternative and/or additional methodology for increasing resistance to abiotic stress, in particular abiotic stress like drought.

It is an object of the current invention to provide for new methods to increase drought resistance in a plant. With such plant it is, for example, possible to produce more biomass and/or more crop and plant product derived thereof if grown under conditions of low water availability/drought in comparison with plants not subjected to the method according to the invention.

SUMMARY OF THE INVENTION

The present invention provides a method for producing a plant having improved drought resistance compared to a control plant, comprising the step of impairing expression of a UPL protein in a plant, said UPL protein comprising an amino acid sequence comprising at least one Pfam HECT domain according to PF00632 and at least one Superfamily ARM repeat according to model SSF48371, and optionally regenerating said plant.

In another aspect, the present invention provides a method for producing a plant having improved drought resistance compared to a control plant, comprising the step of impairing expression of functional UPL4 protein in a plant, plant cell or plant protoplast, wherein said functional UPL4 protein comprises an amino acid sequence comprising at least 35% identity with the amino acid sequence of SEQ ID NO:2, and optionally regenerating said plant.

Said functional UPL4 protein may comprise an amino acid sequence comprising at least one Pfam HECT domain according to PF00632 and at least one Superfamily ARM repeat according to model SSF48371.

The functional UPL4 protein may be a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed.

The invention is further directed to a method for producing a plant having improved drought resistance compared to a control plant, comprising the step of impairing expression of functional UPL4 protein in a plant, plant cell or plant protoplast, wherein said functional UPL4 protein comprises an amino acid sequence having at least one Pfam HECT domain according to PF00632 and at least one Superfamily ARM repeat according to model SSF48371, and optionally regenerating said plant.

The invention also pertains to a method for producing a plant having improved drought resistance compared to a control plant, comprising the step of impairing expression of functional UPL4 protein, wherein said functional UPL4 protein is encoded by a nucleic acid sequence comprising a nucleic acid sequence having at least 60% identity with the nucleic acid sequence of SEQ ID NO:1, and optionally regenerating said plant.

The functional UPL4 protein may be a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed.

The step of impairing expression of functional UPL4 protein may comprise mutating a nucleic acid sequence encoding said functional UPL4 protein. Mutating said nucleic acid sequence may involve an insertion, a deletion and/or substitution of at least one nucleotide. The step of impairing expression may comprise gene silencing. The step of impairing expression may comprise impairing expression of two or more functional UPL4 proteins in said plant.

The method may further comprise the step of producing a plant or plant product from the plant having improved drought resistance.

The invention also relates to the use of an amino acid sequence having at least 35% identity with the amino acid sequence of SEQ ID NO:2 or a nucleic acid sequence having at least 60% identity with the nucleic acid sequence of SEQ ID NO:1 in the screening for drought resistance in plants.

The invention is directed to use of an UPL4 amino acid sequence having SEQ ID NO:2 or a UPL4 nucleic acid sequence of SEQ ID NO:1 in the screening for drought resistance in *Arabidopsis thaliana* plants.

The invention is also concerned with use of at least part of a UPL4 nucleic acid sequence of SEQ ID NO:1 or at least part of an UPL4 amino acid sequence of SEQ ID NO:2 as a marker for breeding drought resistant *Arabidopsis thaliana* plants.

The invention further provides use of a functional UPL4 protein as defined herein for modulating, preferably increasing, drought resistance of a plant.

In another aspect, the invention provides use of a plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed for growing under drought stress conditions, wherein said drought stress conditions cause a control plant, plant cell or plant product wherein expression of said functional UPL4 protein is not impaired to show signs of drought stress such as wilting signs earlier than the plant, plant cell, or plant product wherein expression of functional UPL4 protein is impaired.

The invention also teaches a *Solanum lycopersicum, Gossypium hirsutum, Glycine max, Triticum* spp., *Hordeum vulgare., Avena saliva, Sorghum bicolor, Secale cereale*, or *Brassica napus* plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed. Said plant, plant cell, or plant product may comprise a disrupted endogenous UPL4 gene.

DEFINITIONS

Figure 1:
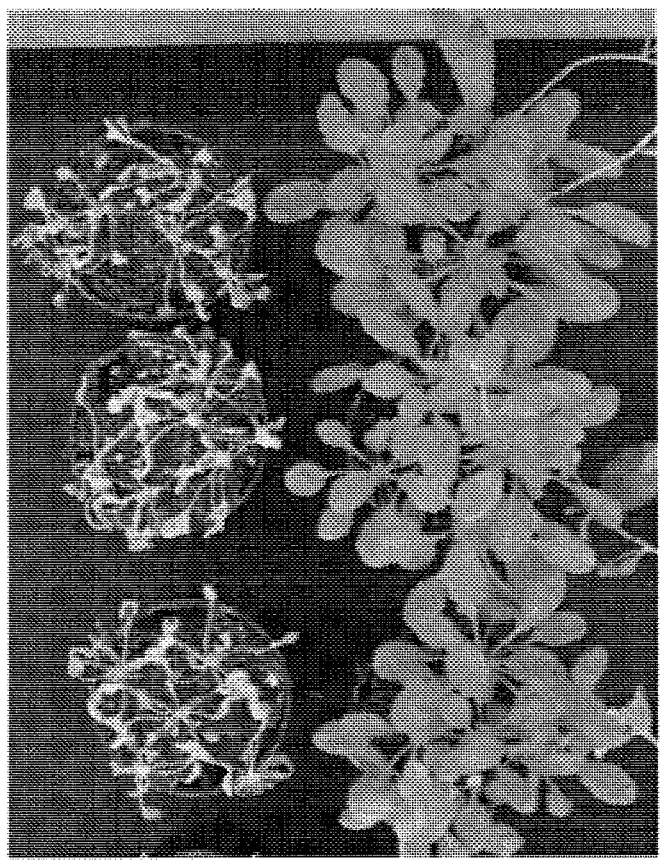
FIG. 1 shows the results of a typical experiment described in the Examples 1 and 2.

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

In this document and in its claims, the verb "to comprise" and its conjugations is used in its non-limiting sense to mean that items following the word are included, but items not specifically mentioned are not excluded. It encompasses the verbs "consisting essentially of" as well as "consisting of".

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

Aligning and alignment: With the term "aligning" and "alignment" is meant the comparison of two or more nucleotide sequences based on the presence of short or long stretches of identical or similar nucleotides. Several methods for alignment of nucleotide sequences are known in the art, as will be further explained below.

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment). "Ectopic expression" refers to expression in a tissue in which the gene is normally not expressed. "Expression of a protein" is used herein interchangeably with the term expression of a gene. It refers to the process in which a DNA region, which is operably linked to appropriate regulatory regions, particularly a promoter, is transcribed into an mRNA and which is subsequently translated into a protein or peptide (or active peptide fragment).

"Functional", in relation to UPL4 proteins (or variants, such as orthologs or mutants, and fragments), refers to the capability of the gene and/or encoded protein to modify the (quantitative and/or qualitative) drought resistance, e.g., by modifying the expression level of the gene (e.g. by overexpression or silencing) in a plant. For example, the functionality of a UPL4 protein obtained from plant species X can be tested by various methods. Preferably, if the protein is functional, silencing of the gene encoding the protein in plant species X, using e.g. gene silencing vectors, will lead to a improved drought resistance as can be tested as explained herein in detail. Also, complementation of a UPL4 knockout with a functional UPL4 protein will be capable of restoring or conferring the characteristic, in this case will restore drought sensitivity. The skilled person will have no difficulties in testing functionality.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sequence sites.

The term "cDNA" means complementary DNA. Complementary DNA is made by reverse transcribing RNA into a complementary DNA sequence. cDNA sequences thus correspond to RNA sequences that are expressed from genes. As mRNA sequences when expressed from the genome can undergo splicing, i.e. introns are spliced out of the mRNA and exons are joined together, before being translated in the cytoplasm into proteins, it is understood that expression of a cDNA means expression of the mRNA that encodes for the cDNA. The cDNA sequence thus may not be identical to the genomic DNA sequence to which it corresponds as cDNA may encode only the complete open reading frame, consisting of the joined exons, for a protein, whereas the genomic DNA encodes and exons interspersed by intron sequences. Genetically modifying a gene which encodes the cDNA may thus not only relate to modifying the sequences corresponding to the cDNA, but may also involve mutating intronic sequences of the genomic DNA and/or other gene regulatory sequences of that gene, as long as it results in the impairment of gene expression.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While a number of methods exist to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403).

As an illustration, by a polynucleotide having a nucleotide sequence having at least, for example, 95% "identity" to a reference nucleotide sequence encoding a polypeptide of a certain sequence it is intended that the nucleotide sequence of the polynucleotide is identical to the reference sequence except that the polynucleotide sequence may include up to five point mutations per each 100 nucleotides of the reference polypeptide sequence. Hence, the percentage of identity of a nucleotide sequence to a reference nucleic acid sequence is calculated over the entire length of the reference nucleic acid sequence. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 2 is intended that the amino acid sequence of the polypeptide is identical to the reference sequence except that the polypeptide sequence may include up to five amino acid alterations per each 100 amino acids of the reference amino acid of SEQ ID NO: 2. Hence, the percentage of identity of an amino acid sequence to a reference amino acid sequence is calculated over the entire length of the reference amino acid sequence. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

A nucleic acid according to the present invention may include any polymer or oligomer of pyrimidine and purine bases, preferably cytosine, thymine, and uracil, and adenine and guanine, respectively (See Albert L. Lehninger, Principles of Biochemistry, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked may mean that the DNA sequences being linked are contiguous.

"Plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing. "Plant cell(s)" include protoplasts, gametes, suspension cultures, microspores, pollen grains, etc., either in isolation or within a tissue, organ or organism.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" includes herein also the 5' UTR region (5' Untranslated Region) (e.g. the promoter may herein include one or more parts upstream (5') of the translation initiation codon of a gene, as this region may have a role in regulating transcription and/or translation. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in plants or plant cells" refers to the general capability of the promoter to drive transcription within a plant or plant cell. It does not make any implications about the spatio-temporal activity of the promoter.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

"Transgenic plant" or "transformed plant" refers herein to a plant or plant cell having been transformed, e.g. by the introduction of a non-silent mutation in an endogenous gene or part there of. Such a plant has been genetically modified to introduce for example one or more mutations, insertions and/or deletions in the gene and/or insertions of a gene silencing construct in the genome. A transgenic plant cell may refer to a plant cell in isolation or in tissue culture, or to a plant cell contained in a plant or in a differentiated organ or tissue, and both possibilities are specifically included herein. Hence, a reference to a plant cell in the description or claims is not meant to refer only to isolated cells or protoplasts in culture, but refers to any plant cell, wherever it may be located or in whatever type of plant tissue or organ it may be present.

Targeted nucleotide exchange (TNE) is a process by which a synthetic oligonucleotide, partially complementary to a site in a chromosomal or an episomal gene directs the reversal of a single nucleotide at a specific site. TNE has been described using a wide variety of oligonucleotides and targets. Some of the reported oligonucleotides are RNA/DNA chimeras, contain terminal modifications to impart nuclease resistance.

As used herein, the term "drought stress" or "drought" refers to a sub-optimal environmental condition associated with limited availability of water to a plant. Limited availability of water may occur when for instance rain is absent or lower and/or when the plants are watered less frequently than required. Limited water availability to a plant may also occur when for instance water is present in soil, but can not efficiently be extracted by the plant. For instance, when soils strongly bind water or when the water has a high salt content, it maybe more difficult for a plant to extract the water from the soil. Hence, many factors can contribute to result in limited availability of water, i.e. drought, to a plant. The effect of subjecting plants to "drought" or "drought stress" may be that plants do not have optimal growth and/or development. Plants subjected to drought may have wilting signs. For example, plants may be subjected to a period of at least 15 days under specific controlled conditions wherein no water is provided, e.g. without rain fall and/or watering of the plants.

The term "improved drought resistance" refers to plants which, when provided with improved drought resistance, when subjected to drought or drought stress do not show effects or show alleviated effects as observed in plants not provided with improved drought resistance. A normal plant has some level of drought resistance. It can easily be determined whether a plant has improved drought resistant by comparing a control plant with a plant provided with improved drought resistance under controlled conditions chosen such that in the control plants signs of drought can be observed after a certain period, i.e. when the plants are subjected to drought or drought stress. The plants with improved drought resistance will show less and/or reduced signs of having been subjected to drought, such as wilting, as compared to the control plants. The skilled person knows how to select suitable conditions such as for example the controlled conditions in the examples. When a plant has "improved drought resistance", it is capable of sustaining normal growth and/or normal development when being subjected to drought or drought stress would otherwise would have resulted in reduced growth and/or reduced development of normal plants. Hence, "improved drought resistance" is a relative term determined by comparing plants, whereby the plant most capable of sustaining (normal) growth under drought stress is a plant with "improved drought resistant" plant. The skilled person is well aware how to select appropriate conditions to determine drought resistance of a plant and how to measure signs of droughts, such as described in for example manuals provided by the IRRI, Breeding rice for drought prone environments, Fischer et al., 2003, and by the CIMMYT, Breeding for drought and nitrogen stress tolerance in maize: from theory to practice, Banzinger et al, 2000. Examples of methods determining improved drought resistance in plants are provided in Snow and Tingey, 1985, Plant Physiol, 77, 602-7 and Harb et al., Analysis of drought stress in *Arabidopsis*, AOP 2010, Plant Physiology Review, and as described in the example section below.

DETAILED DESCRIPTION OF THE INVENTION

The current invention relates to the improvement of drought resistance of a plant by impairing the expression of a functional UPL4 protein in said plant. The improvement is relative to a control plant, in which such modification has not been introduced or is not present and in which expression of a functional UPL4 protein is not impaired. In other words, modified plant according to the invention is, in comparison to the control plant, i.e. non-modified plant, better able to grow and survive under conditions of reduced water availability, (temporary) water-deprivation or conditions of drought. It is understood that according to the invention modifying, e.g., impairing, expression of functional UPL4 protein may involve genetic modification, e.g., of UPL4 gene expression, or targeted nucleotide exchange.

Genetic modification includes introducing mutations, insertions, deletions in the nucleic acid sequence of interest and/or insertion of gene silencing constructs into a genome of a plant or plant cell that target the nucleic acid sequence of interest. Genetically modifying a nucleic acid sequence, e.g., a gene, which encodes the mRNA may not only relate to modifying exon sequences corresponding to the mRNA sequence, but may also involve mutating intronic sequences of genomic DNA and/or (other) gene regulatory sequences of that nucleic acid sequence, e.g., gene.

In the context of the present invention, the functional UPL4 protein may be a protein that, when expressed in an *Arabidopsis thaliana* T-DNA insertion line having a disrupted endogenous UPL4 gene, such as an At5g02880 knockout line, e.g., SALK_091246C recited herein, results in a plant with an impaired drought resistance compared to the drought resistance of said *Arabidopsis thaliana* T-DNA insertion line having a disrupted endogenous UPL4 gene, e.g., an At5g02880 knockout line, e.g., SALK_091246C, in which said functional UPL4 protein is not expressed.

The term "disrupted endogenous UPL4 gene" as used herein refers to a UPL4 gene naturally present in the genome of a plant which is disrupted, e.g., interrupted, e.g., by means of a T-DNA insertion into said UPL4 gene. Disruption of said endogenous UPL4 gene may result in the absence of expression of said endogenous UPL4 gene, and thus in the absence of endogenous UPL4 protein (either functional or non-functional).

The term "control plant" as used herein refers to a plant of the same species, preferably of the same variety, preferably of the same genetic background.

The current invention also relates to the modulation of drought resistance of a plant by modifying the expression of functional UPL4 protein in said plant. The modulation is relative to a control plant (preferably of the same species and/or variety, and preferably of the same genetic background) in which such modification has not been introduced or is not present.

In an aspect, the present invention provides a method for producing a plant having improved drought resistance compared to a control plant, comprising the step of impairing expression of a UPL protein in a plant, said UPL protein comprising an amino acid sequence comprising at least one Pfam HECT domain according to PF00632 and at least one Superfamily ARM repeat according to model SSF48371.

In another aspect, the invention is concerned with a method for producing a plant having improved drought resistance compared to a control plant, the method comprising the step of impairing the expression of functional UPL4 protein in said plant.

"Impairing expression of a functional UPL4 protein" as used herein may mean that the expression of the UPL4 gene is impaired, and/or that expression of the UPL4 gene is normal but translation of the resulting mRNA is inhibited or prevented (for example, by RNA interference), and/or that the amino acid sequence of UPL4 protein has been altered such that its ubiquitin protein ligase specific activity is reduced compared to the ubiquitin protein ligase specific activity of the protein as depicted in SEQ ID NO:2, preferably under physiological conditions, particularly identical physiological conditions. Alternatively, a UPL4 protein may become non-functional or less functional by scavenging thereof using UPL4 inhibitors such as an antibody specifically binding to said UPL4 protein, or other UPL4 inhibitors, e.g., proteins that stop, prevent, or reduce the activity of a UPL4 proteins, or chemical inhibitors such as ions, or metals, or scavenging of cofactors. For example, an antibody specifically binding to said UPL4 protein may be expressed simultaneously with said UPL4 protein, thereby reducing its specific activity. The ubiquitin protein ligase specific activity of a UPL4 protein may be considered "reduced" if the ubiquitin protein ligase specific activity of such protein is statistically significantly less than the ubiquitin protein ligase specific activity of the protein as depicted in SEQ ID NO:2. The ubiquitin protein ligase specific activity of a UPL4 protein may, for example, be reduced by at least 5%, 10%, 15%, 20%, 25%, 30%, 35%, 40%, 45%, 50%, or more. Reduced expression of the endogenous UPL4 gene of a plant may be accomplished by altering the promoter sequence, for example, using targeted mutagenesis. The skilled person will be capable of determining ubiquitin protein ligase specific activity based on routine methods.

It is believed by the current inventors that impairing expression (e.g. by reducing, repressing or deleting expression and/or activity) of functional UPL4 protein leads to the absence or a reduced level of functional UPL4 protein, either as a consequence of low expression, e.g. via RNA interference, or as a consequence of decreased activity/functionality of the UPL4 protein, or one or more of the above, and that said absence or reduced level of functional UPL4 protein leads to decreased need for water or improved resistance to drought of said plant.

Ubiquitin Protein Ligase proteins (UPLs) are known to be involved in the selective degradation of regulatory proteins in both yeast and animals (Huibregtse et al. (1995) Proc. Natl. Acad. Sci. USA 92, 2563-2567; Pickart (2001) Annu. Rev. Biochem. 70, 503-533). Proteins committed for degradation are modified with a chain of multiple Ubiquitins and are then recognized by the 26S proteasome. An important class of these Ubiquitin Protein Ligase proteins is formed by the HECT E3s, which comprise a conserved 350-amino acid domain called the HECT domain at the C-terminal end (based on its homology to the C-terminus of human E6-Associated Protein (E6-AP) (Huibregtse et al. (1995) Proc. Natl. Acad. Sci. USA, 92, 2563-2567). The HECT domain includes a highly conserved region surrounding the positionally invariant cystein required to catalyze Ubiquitin transfer.

According to Downes et al. (2003, Plant J 35, 729-742), plants also contain HECT E3s, with seven present in *Arabidopsis*: UPL1, UPL2, UPL3, UPL4, UPL5, UPL6, and UPL7. Downes et al. further describe that UPL1, UPL2, UPL3, UPL4, UPL5, UPL6, and UPL7 can be grouped by structure into four subfamilies based on intron/exon positions of the corresponding genes, protein sequence and length, and the presence of additional protein motifs upstream of the HECT domain: UPL1/2, UPL3/4, UPL5, and UPL6/7. The presence of a variety of domains upstream of the HECT domain suggests that individual members of the UPL1-UPL7 family have distinct sets of targets and functions (see Downes et al. 2003 The Plant Journal, 35, 729-742, in particular FIG. 1 thereof, for more information on the distinct characteristics of the different UPL proteins).

In *Arabidopsis thaliana*, Ubiquitin Protein Ligase 4 can be distinguished from Ubiquitin Protein Ligase 3 for instance by the absence of a 225-residue region 650 amino acids from the C-terminus of Ubiquitin Ligase 4 (Downes et al. (2003) Plant J 35, 729-742).

Ubiquitin Protein Ligase 4 as found in *Arabidopsis thaliana* has been reported to have approximately 54% amino acid sequence identity to Ubiquitin Protein Ligase 3 (Downes et al. (2003) Plant J 35, 729-742). The locus name of the Ubiquitin Protein Ligase 4 is At5g02880, and the ORF name is F9G14.

The UPL4 protein of *Arabidopsis thaliana* is comprised of 1502 amino acids (as depicted in SEQ ID NO:2). The cDNA encoding the UPL4 protein of *Arabidopsis thaliana* comprises 4506 nucleotides (depicted in SEQ ID NO:1). The UPL4 gene of *Arabidopsis thaliana* is also referred to as KLI5 (for Kaktus Like on chromosome 5) based on its similarity with the KAKTUS gene in *Arabidopsis* (see Refy et al. Mol Gen Genomics (2003) 270: 403-414).

A "UPL4 protein" as used herein comprises the protein depicted in SEQ ID NO:2, as well as fragments and variants thereof. Variants of a UPL4 protein include, for example, proteins having at least 40%, 50%, 60%, 70%, 75%, 80%, 85%, 90%, 95%, 96%, 97%, 98%, 99%, or more, such as 100%, amino acid sequence identity, preferably over the entire length, to SEQ ID NO:2. Amino acid sequence identity is determined by pairwise alignment using the Needleman and Wunsch algorithm and GAP default parameters as defined above.

An *Arabidopsis thaliana* plant having a T-DNA insertion in the gene encoding UPL3 is known from Downes et al. ((2003) Plant J. 35, 729-742). This UPL3 mutant shows aberrant trichome development. Downes et al. also describe an *Arabidopsis thaliana* plant having a T-DNA insertion in the gene encoding UPL4. Downes et al describe that, in contrast to the UPL3 mutant, the UPL4 mutant showed no abnormal phenotypes when grown under optimal growth conditions and developed normal trichomes.

In another aspect there is provided for a method for producing a plant having improved drought resistance, the method comprising the step of impairing the expression in said plant of a gene encoding a UPL4 protein.

"Impaired expression" according to the present invention denotes the absence or reduced presence of a functional UPL4 protein and variants thereof comprising an amino acid sequence with more than 40%, 50%, 60%, 70%, 80%, 90%, 95% sequence identity therewith. It also denotes the absence of lowered presence of proteins described herein that comprise at least one Pfam HECT domain, PF00632, and at least one Superfamily ARM repeat, model SSF48371. A skilled person is well aware of the many mechanism available to him in the art to impair the expression of a gene at for example the transcription level or the translation level.

In another aspect there is provided for a method for increasing drought resistance of a plant, the method comprising the step of impairing the expression in said plant of a gene, wherein the amino acid sequence (or protein) encoded by said gene comprises at least one Pfam HECT domain (PF00632) and at least one Superfamily ARM repeat (model SSF48371), as determined as described below. It is understood that the phrase "at least one Superfamily ARM repeat model SSF48371" comprises the four Armadillo repeat sequences from the UPL4 gene of the amino acid sequence of FIG. 3. Thus, the phrase "at least one Superfamily ARM repeat model SSF48371" means to comprise the four Armadillo repeat sequences.

As used herein "Pfam" or "PFAM" refers to a large collection of multiple sequence alignments and hidden Markov models covering many common protein families. The Pfam database contains a large collection of protein families, each represented by multiple alignments. These alignments have been used to build hidden Markov models (HMMs) for each protein domain family. The alignments represent evolutionary conserved structures and the presence of a domain in a protein of interest can be indicative towards its biological function. Profile hidden Markov models (profile HMMs) built from the Pfam alignments are useful for automatically recognizing that a new protein belongs to an existing protein family even if the homology by alignment appears to be low. Other proteins in the same protein family are identified by querying the amino acid sequence of a protein sequence against the Hidden Markov Model using HMMER software. The HMMER software is able to use this HMM to search for a presence of this domain in new sequences. Potential candidate proteins hits were derived by taking into account only HMMER hits in their sequences that were above the default inclusion threshold.

Pfam version 24.0 (October 2009) contains alignments and models for 11912 protein families (see The Pfam protein families database: R. D. Finn, et al Nucleic Acids Research (2010) Database Issue 38:D211-222). Pfam is based on a sequence database called Pfamseq, which is based on UniProt release 15.6 (Swiss-Prot release 57.6 and SP-TrEMBL release 40.6).

The alignments in the Pfam database represent evolutionary conserved structures that may be relevant for a protein's function. The hidden Markov models (HMMs) built from the Pfam alignments are useful for establishing if a protein belongs to an existing protein family. This is even the case if homology/identity by alignment would be low. Once, for example, a protein which is involved in a certain characteristic (e.g. sensitivity to drought) is recognized, and, for example, impairment of its expression imparts an enhanced trait (e.g. increased resistance to drought), other proteins in the same protein family can be identified by the skilled person by comparing the amino acid sequence of a protein (and encoded by candidate DNA) against the Hidden Markov Model which characterizes the Pfam domain (in the current invention Pfam HECT PF00632 model) using HMMER software.

After establishment of the presence of a Pfam HECT domain (PF00632) as described above, a candidate protein also has to meet the requirement of comprising at least on Superfamily ARM repeat (HMM model SSF48371; as can be established by, for example using the InterProScan application (Quevillon et al. (2005) 33(2) W116-W120; E. M. Zdobnov and R. Apweiler (2001) *Bioinformatics,* 17, 847-848). Quevillon and colleagues describe that the InterProScan is a tool that combines different protein signature recognition methods from the InterPro consortium member databases into one resource, with distinct publicly available databases in the application. Protein as well as DNA sequences can be analyzed. A web-based version is accessible for academic and commercial organizations from the EBI.

The SUPERFAMILY annotation is based on a collection of hidden Markov models, which represent structural protein domains at the SCOP superfamily level. A superfamily groups together domains which have an evolutionary relationship. The annotation is produced by scanning protein sequences from over 1,400 completely sequenced genomes against the hidden Markov models.

All software is applied under default settings.

In summary, a Hidden Markov model for the HECT domain (PF00632 model was obtained from the Pfam database and placed into a separate file. The HMMER software was used to determine that the amino proteins sequences are characterized by the Pfam HECT domain. In addition, the filtered protein set was further reduced by employing the SuperFamily package (using the SSF48371 model) from the InterProScan application (Quevillon et al. to mine for ARM repeats). Furthermore, the sequences were aligned using the MUSCLE multiple alignment tool. The phylogenetic tree was inferred using the protpars algorithm from the PHYLIP package. (Plant) Proteins meeting both requirements (having a Pfam HECT PF00632 domain and a SuperFamily SSF48371 model Arm repeat), are proteins according to the invention; and impairment of the expression thereof may be useful in providing improved/increased drought resistance to the plant, and examples of such proteins and cDNA are disclosed herein. The skilled person is well aware on how to determine and test based on the information provided above.

Without being bound by theory, the current inventors speculate that the presence of this combination of domains in the protein according to the invention increases sensitivity of the plants for drought, and that impairment of the expression of such proteins having these domains, improves resistance of a plant to drought.

Impairment at the transcriptional level can be the result of the introduction of one or more mutations in transcription regulation sequences, including promoters, enhancers, initiation, termination or intron splicing sequences. These sequences are generally located 5' of, 3' of, or within the coding sequence of the genes according to the invention. Independently, or at the same time, impairment of expression can also be provided by deletion, substitution, rearrangement or insertion of nucleotides in the coding region of the genes.

For example, in the coding region, nucleotides may be substituted, inserted or deleted leading to the introduction of one, two or more premature stop-codons. Also, insertion, deletion, rearrangement or substitution can lead to modifications in the amino acid sequence encoded, and thereby providing for impaired expression of functional UPL4 protein. Even more, large parts of the genes may be removed, for example, at least 10%, 20%, 30%, 40%, 50%, 60%, 70%, 80%, 90% or even 100% of the (coding region) of the gene is removed from the DNA present in the plant, thereby impairing the expression of functional UPL4 protein.

Alternatively, one, two, three of more nucleotides may be introduced in the gene or genes encoding for a UPL4 protein, either leading to, for example, a frame-shift, or leading to the introduction of a sequence encoding additional amino acids, or the introduction of sequence not encoding amino acids, or the introduction of large inserts, thereby impairing the provision/expression of functional UPL4 protein.

In other words, deletion, substitution or insertion of nucleotide(s) in a nucleotide sequence encoding a UPL4 protein, as described above, may lead to, for example, a frame shift, an introduction of a stop codon, or the introduction of a non-sense codon. In particular the introduction of a stop codon and the introduction of a frame shift mutation are generally accepted as efficient ways to produce a knockout plant, that is, a plant with reduced, repressed or deleted expression and/or activity of a specific protein.

A frame shift mutation (also called a framing error or a reading frame shift) is a genetic mutation caused by indels (insertions or deletions) of a number of nucleotides that is not evenly divisible by three in a nucleotide sequence. Due to the triplet nature of gene expression by codons, the insertion or deletion can change the reading frame (the grouping of the codons), resulting in a completely different translation from the original. The earlier in the sequence the deletion or insertion occurs, the more altered the protein produced is. A frame shift mutation will in general cause the reading of the codons after the mutation to code for different amino acids, but there may be exceptions resulting from the redundancy in the genetic code. Furthermore, the stop codon ("UAA", "UGA" or "UAG") in the original sequence will not be read, and an alternative stop codon may result at an earlier or later stop site. The protein produced may be abnormally short or abnormally long.

The introduction of a stop codon in a nucleotide sequence encoding a UPL4 protein as defined herein may result in a premature stop of transcription, which generally results in a truncated, incomplete, and non-functional UPL4 protein. Preferably, the stop codon is introduced early in the transcription direction. The earlier in the nucleotide sequence the stop codon is introduced, the shorter and the more altered the protein produced is. The introduction of a nonsense codon in a nucleotide sequence encoding a UPL4 protein may result in transcript mRNA wherein e.g. one codon no longer codes for the amino acid as naturally occurring in UPL4, for example a codon that normally codes for an amino acid which is essential for a UPL4 protein to be functional. Hence, such UPL4 protein may not be functional.

In other words, the impairment may comprise mutating one or more nucleotides in the genes disclosed herein resulting either in the presence of less or even in the total absence of protein expression product (i.e. the absence of protein that would be obtained when the genes according to the invention were not modified as described above), or in the presence of non-functional protein.

Therefore, in one embodiment of the method disclosed herein, the impairment is the consequence of one or more mutations in said gene resulting in the presence of less protein expression product or absence of a protein expression product.

The term inhibition/presence of less as used herein relates to a reduction in protein expression of at least 10%, 20%, 30%, 40%, 50%, 60%, 70%, 80%, 90% or even 99% in comparison to a control plant, in which the expression is not impaired. The term "absence of protein expression" refers to the virtual absence of any expression product, for example less than 5%, 4%, 3%, 2% or even less than 1% in comparison to the control.

As will be understood by a skilled person, a mutation may also be introduced in a nucleotide sequence encoding UPL4 as defined herein by the application of mutagenic compounds, such as ethyl methanesulfonate (EMS) or other compounds capable of (randomly) introducing mutations in nucleotide sequences. Said mutagenic compounds or said other compound may be used as a means for creating plants harboring a mutation in a nucleotide sequence encoding a UPL4 protein.

Alternatively, the introduction of a mutation in a nucleotide sequence encoding a (UPL4) protein according to the invention may be effected by the introduction of transfer-DNA (T-DNA) in the nucleotide sequence encoding such protein, for instance T-DNA of the tumor-inducing (Ti) plasmid of some species of bacteria such as *Agrobacterium tumefaciens*. A T-DNA element may be introduced in said nucleotide sequence, leading to either a non-functional protein or to the absence of expression of the protein, consequently decreasing the need for water of a plant obtained by the method according to the invention (see for example Krysan et al. 1999 The Plant Cell, Vol 11. 2283-2290). Likewise advantage can be taken from the use of transposable element insertion (See for Example Kunze et al (1997) Advances in Botanical Research 27 341-370 or Chandlee (1990) Physiologia Planta 79(1) 105-115).

In an embodiment, introducing a mutation in a nucleotide sequence encoding a protein according to the invention is performed by targeted nucleotide exchange (TNE), for instance as described in WO2007073170. By applying TNE, specific nucleotides can be altered in a nucleotide sequence encoding UPL4, whereby, for instance, a stop codon may be introduced which may for instance result in a nucleotide sequence encoding a truncated protein according to the invention with decreased or disappeared activity.

In another embodiment there is provided a method as disclosed above wherein the impairment of expression of functional UPL4 protein is caused by expression of non-functional protein. As explained above, a skilled person has no problem in determining functionality of the genes according to the invention. For example, he may perform complementation studies, by introducing the control gene, without any modifications, into a plant in which the expression of a protein according to the invention has been impaired and study drought resistance.

Alternatively he may perform experiments analogous to those experiments described below in the examples, and determine drought resistance in a plant in which one or more mutations were introduced in the genes according to the invention, by comparison to a suitable control/wild-type plant.

Impairment can also be provided at the translational level, e.g. by introducing a premature stop-codon or by posttranslational modifications influencing, for example, protein folding.

Independent of the mechanism, impairment according to the present invention is indicated by the absence or reduced presence of functional UPL4 protein. In contrast, non-functional UPL4 protein may be present at normal levels.

As explained above the term inhibition of expression or reduced presence as used herein relates to a reduction in protein expression of at least 10%, 20%, 30%, 40%, 50%, 60%, 70%, 80%, 90% or even 99% in comparison to a control plant, in which the expression is not impaired. The term "absence of protein expression" refers to the virtual absence of any expression product, for example less than 5%, 4%, 3%, 2% or even less than 1% in comparison to the control.

According to another embodiment, impairment is caused by gene silencing, for example with RNA interference or RNA silencing.

With the help of molecular biology methods readily available to the skilled person, impairment of the genes can also be accomplished by gene silencing, for example using RNA interference techniques, dsRNA or other expression silencing techniques (see for example, Kusaba et. al (2004) Current Opinion in Biotechnology 15:139-143, or Preuss and Pikaard (2003) in RNA Interference (RNAi)~Nuts & Bolts of siRNA Technology (pp. 23-36), ©2003 by DNA Press, LLC Edited by: David Engelke, Ph.D.) or, as already discussed above, knocking out.

In another preferred embodiment, and as already discussed above, there is provided for a method according to the invention wherein the impairment is caused by insertion, deletion and/or substitution of at least one nucleotide. For example, 1, 2, 3 . . . 10, 40, 50, 100, 200, 300, 1000, or even more nucleotides may be inserted, deleted or substituted in the genes according to the invention. Also anticipated are combinations of insertion, deletion and/or substitution, either in the coding or in the non-coding regions of the gene.

In another embodiment of the method disclosed herein the method comprises the step of impairing the expression in said plant of more than 1, for example 2, 3, 4, 5, or all genes encoding a UPL4 protein.

In this embodiment, the expression of more than one gene as described above, and present in a particular plant is impaired. For example the expression of one, two, three, four, or all of the genes encoding a UPL4 protein, as present in a plant, is impaired. By impairing the expression of more genes as described above at the same time (when present in a plant) even more improved drought resistance can be achieved.

In another embodiment, the plant provided by the method according to the invention can be used for the production of further plants and or plant products derived there from. The term "plant products" refers to those material that can be obtained from the plants grown, and include fruits, leaves, plant organs, plant fats, plant oils, plant starch, plant protein fractions, either crushed, milled or still intact, mixed with other materials, dried, frozen, and so on. In general such plant products can, for example be recognized by the presence of a gene as disclosed herein so modified that the expression of a functional protein is impaired, as detailed above.

Preferably, expression and/or activity of the UPL4 protein according to the invention is impaired (e.g. reduced, repressed or deleted) in a plant belonging to the Brassicaceae family including *Brassica napus* (rape seed), Solanaceae-family, including tomato, or Curcurbitaceae family, including melon and cucumber, or the Poacease family including *Oryza*, including rice, or *Zea mays*, including maize (corn), or the Fabaceae including legume, pea, or bean. Preferably the method according to the invention is applied in tomato, rice, maize, melon, or cucumber, thereby providing a plant with decreased need for water or improved resistance to drought in comparison to a corresponding non-transformed plant. Also provided is a plant cell, plant or plant product obtainable by the method according to the invention, and wherein said plant cell, plant or plant product shows reduced expression of functional UPL4 protein, compared to a control plant not subjected to the method according to the invention.

Also provided is a plant cell, plant or plant product, characterized in that in said plant cell, plant or plant product the expression of at least one, preferably all genes encoding UPL4 protein, such as those wherein the cDNA sequence corresponding to the mRNA transcribed from said at least one gene comprises the sequence shown in SEQ ID NO:1, and those wherein the cDNA sequence corresponding to the mRNA sequence transcribed from said at least one gene comprise at least 40%, 50%, 60%, 70%, 80%, 90%, 95% identity with the nucleotide sequence of SEQ ID NO:1 and/or wherein the amino acid sequence encoded by said at least one gene comprises the sequence shown in SEQ ID NO:2, or wherein the amino acid sequence encoded by said at least one gene comprises at least 40%, 50%, 60%, 70%, 80%, 90%, 95% identity with the amino acid sequence of SEQ ID NO:2 and/or wherein the amino acid sequence encoded by said at least one gene comprises at least one Pfam HECT domain (PF00632) and at least one Superfamily ARM repeat (model SSF48371) as defined above, is impaired. Preferably the plant is not the *Arabidopsis thaliana* mutant as described in the examples below, or a *Brachypodium* T-DNA insertion mutant, or a *Zea mays* T-DNA insertion mutant, or an *Oryza sativa* T-DNA insertion mutant.

Figure 2:
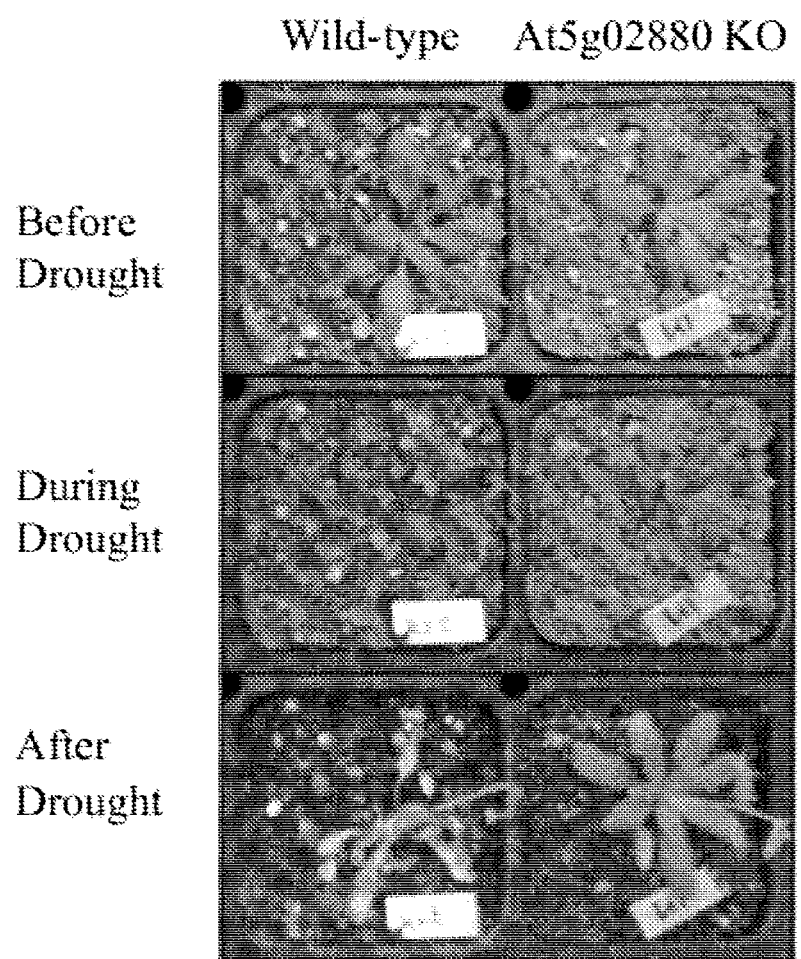
FIG. 2 shows the drought resistant phenotype of the UPL4 knockout (*Arabidopsis* At5g02880 insertion mutant) as compared to the drought sensitive phenotype of a control (wild-type) plant.

In another aspect there the invention is directed to a use of a gene wherein the cDNA sequence corresponding to the mRNA sequence transcribed from said gene comprises the sequence shown in SEQ ID NO: 1 and FIG. 2, and those wherein the cDNA sequence corresponding to the mRNA sequence transcribed from said gene comprises at least 40%, 50%, 60%, 70%, 80%, 90%, 95% identity therewith and/or wherein the amino acid sequence encoded by said gene comprises the sequence shown in SEQ ID NO:2, and amino acid sequence sequences with more than 35%, 40%, 50%, 60%, 70%, 80%, 90%, 95% identity therewith and/or wherein the amino acid sequence encoded by said gene comprises at least one Pfam HECT domain (PF00632) and at least one Superfamily ARM repeat (model SSF48371) as defined above, for providing increased drought resistance to a plant.

In this embodiment, the gene described can be used as a target for improving drought resistance in a plant, in accordance with the disclosure herein, or the gene can be used to identify new proteins involved in drought sensitivity and resistance.

In another embodiment a use is provided of a UPL4 sequence having SEQ ID No.1 or 2 of the *Arabidopsis thaliana* species in the screening for drought resistance in *Arabidopsis thaliana* plants. In addition, a use is provided wherein the UPL4 sequence is an analogous sequence to SEQ ID No.1 or 2 of an other plant species and wherein the screening is in plants of the other plant species. Furthermore, a method is provided for screening plants or plant cells with improved drought resistance comprising the steps of:
  providing a heterogenic population of plant cells or plants of the *Arabidopsis thaliana* species;
  providing a UPL4 sequence having SEQ ID No.1 or 2;
  determining the sequence of at least part of the UPL4 gene of the plants cells or plants;
  comparing the determined UPL4 sequences from the plant cells or plants with the provided UPL4 sequence;
  identifying plant cells or plants wherein the UPL4 sequence comprises a mutation.

Alternatively, in the method, the plant cells or plants that are provided are of an other species, and wherein the UPL4 gene sequence that is provided is an analogous sequence of the other species.

Hence, by using the UPL4 sequence SEQ ID No.1 or SEQ ID No.2 of the species *Arabidopsis thaliana*, or an analogous sequence thereof from an other species, mutated UPL4 sequences can be identified in the plant species that may provide improved drought resistance. An analogous sequence, in an other species, of the UPL4 sequence SEQ ID No.1 or SEQ ID No.2 of the species *Arabidopsis thaliana* is defined as a sequence having at least 35%, 40%, 50%, 60%, 70%, 75%, 80%, 85%, 90%, 95%, or at least 99%, sequence identity therewith. The analogous UPL4 protein may have substantially the same function as SEQ ID No.1 or SEQ ID No.2.

In the method, a heterogenic population of plant cells or plants of the species is provided. The heterogenic population may for example be provided by subjecting plant cells to a mutagen that introduces random mutations thereby providing a heterogenic population of plant cell. Hence, the heterogenic population may be derived from a single plant variety, which is subjected to random mutagenesis in order to obtain a variety of mutations in the offspring thereby providing a heterogenic population. Many mutagens are known in the art, e.g. ionic radiation, UV-radiation, and mutagenic chemicals such as azides, ethidium bromide or ethyl methanesulfonate (EMS). Hence the skilled person knows how to provide for a heterogenic population of plants or plant cells. Also, the skilled person may also provide a variety of plants as a heterogenic population, i.e. not a single variety from a species. A variety of plants show genetic variety, they are not genetically identical, but because the plants are from the same species they are substantially identical. In any case, a heterogenic population of plant cells or plants may have at least 95%, 96%, 97%, 98%, 98%, 99%, 99.5% or at least 99.9% sequence identity.

By determining at least part of the sequence of the UPL4 gene sequence with the sequence of the plants or plant cells from the heterogenic population, and subsequently comparing these sequences with the provided UPL4 gene sequence (the reference), plant cells or plants can be identified that comprise a mutation in the UPL4 gene sequence. It is understood that such a comparison can be done by alignment of the sequences and that a mutation is a difference in respect of at least one nucleic acid or amino acid position in the analogous (reference) UPL4 sequence of the plant species. In this way, plants or plant cells are identified that have mutations in the UPL4 gene (e.g. insertions, deletions, substitutions) that may provide improved drought resistance.

Preferably, plants are selected that have mutations that would result in an impairment of expression of a functional UPL4 protein, such as already outlined above. Mutations that would impair expression of a functional UPL4 protein may be mutations that would disrupt the open reading frame (introduce a frame shift or a stop codon) or disrupt or otherwise alter the function of the encoded protein by altering nucleotides in codons encoding amino acids that are essential for the proper functioning of the protein, thereby leading to modified (e.g. increased) resistance to draught in comparison to the non-altered protein. The method may also be used for example in the screening and selection of plants that have been subjected to genetic modification which targets the UPL4 sequence as outlined above. Also, the UPL4 sequence may also be used in a screening assay, in which a (heterogenic) population of plants are subjected to drought.

In another embodiment, the use is provided of at least part of UPL4 having SEQ ID No.1 or SEQ ID No.2 of the *Arabidopsis thaliana* species as a marker for breeding drought resistant *Arabidopsis thaliana* plants. Also, the UPL4 sequence may be of an analogous sequence of an other species wherein the marker is for breeding drought resistant plants of the other plant species.

The present invention also relates to use of a plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed for growing under drought stress conditions, wherein said drought stress conditions cause a control plant, plant cell, or plant product wherein expression of said functional UPL4 protein is not impaired to show signs of drought stress such as wilting signs earlier than the plant, plant cell, or plant product wherein expression of functional UPL4 protein is impaired.

In an aspect, the present invention pertains to a plant, plant cell or plant product obtainable or obtained by the method taught herein. Additionally, the invention provides a seed derived from such plant.

The invention also relates to a plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed. Said plant, plant cell or plant product may, for example, comprise a disrupted endogenous UPL4 gene.

The plant, plant cell or plant product may be any plant or plant cell, or may be derived from any plant, such as monocotyledonous plants or dicotyledonous plants, but most preferably the plant belongs to the family Solanaceae. For example, the plant may belong to the genus *Solanum* (including *lycopersicum*), *Nicotiana*, *Capsicum*, *Petunia* and other genera. The following host species may suitably be used: Tobacco (*Nicotiana* species, e.g. *N. benthamiana, N. plumbaginifolia, N. tabacum*, etc.), vegetable species, such as tomato (*Solanum lycopersicum*) such as e.g. cherry tomato, var. *cerasiforme* or currant tomato, var. *pimpinellifolium*) or tree tomato (*S. betaceum*, syn. *Cyphomandra betaceae*), potato (*Solanum tuberosum*), eggplant (*Solanum melongena*), pepino (*Solanum muricatum*), cocona (*Solanum sessiliflorum*) and naranjilla (*Solanum quitoense*), peppers (*Capsicum annuum, Capsicum frutescens, Capsicum baccatum*), ornamental species (e.g. *Petunia hybrida, Petunia axillaries, P. integrifolia*).

Alternatively, the plant may belong to any other family, such as to the Cucurbitaceae or Gramineae. Suitable host plants include for example maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa* indica cultivar-group or *japonica* cultivar-group), forage grasses, pearl millet (*Pennisetum* spp. e.g. *P. glaucum*), tree species (*Pinus*, poplar, fir, plantain, etc), tea, coffea, oil palm, coconut, vegetable species, such as pea, zucchini, beans (e.g. *Phaseolus* species), cucumber, artichoke, asparagus, broccoli, garlic, leek, lettuce, onion, radish, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, *Petunia*, Chrysanthemum, Lily, *Gerbera* species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*), or model organisms, such as *Arabidopsis thaliana*.

Preferred hosts are "crop plants", i.e. plant species which is cultivated and bred by humans. A crop plant may be cultivated for food purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork and the like.

Preferably, the plant, plant cell or plant product of the invention is not an *Arabidopsis thaliana* or *Brachypodium* plant, plant cell or plant product.

The plant, plant cell or plant product of the invention may, for example, be a *Solanum lycopersicum* or *Brassica rapa* plant, plant cell or plant product.

Thus, the invention pertains, for example, to a *Solanum lycopersicum, Gossypium hirsutum, Glycine max, Triticum* spp., *Hordeum vulgare., Avena sativa, Sorghum bicolor, Secale cereale*, or *Brassica napus* plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed. Said plant, plant cell, or plant product may comprise a disrupted endogenous UPL4 gene.

All references recited herein are herein incorporated by reference in their entirety.

EXAMPLES

Example 1 Drought Test

*Arabidopsis thaliana* (At) seeds transformed with *Agrobacterium tumefaciens* vector pROK2, leading to the absence of functional UPL4 protein (NASC ID: N655716, AGI code AT5G02880 and SALK_091246 C; hereafter referred to a mutant seeds or mutant plants) were obtained from the Nottingham *Arabidopsis* Stock Centre (NASC; School of Biosciences, University of Nottingham, Sutton Bonington Campus, Loughborough, LE12 5RD United Kingdom). As control At Col-0 (Columbia, N60000); hereafter referred to as control seed or plant) were used.

Growth Medium:

A soil mixture comprising one part of sand and vermiculite and two parts of compost was used (sand:vermiculite:compost=1:1:2). This mixture increases the water percolation hence facilitates uniform water uptake by each pot and better water drainage. Before sowing, the seeds were kept at 4° C. for 3 days under dark and humid conditions for stratification.

Both mutant and control seeds were sown in a rectangular tray containing 8×5=40 pots of ~4 cm diameter with density of 5 plants per pot. Nutrient solution (EC=1.5) was supplied to all the plants from the bottom of the pots in the tray 10 days after germination (DAG), and at 15 DAG the plants were subjected to drought (for 15, 16, 17 or 18 days) by transferring the pots to dry trays. Subsequently, plants were rehydrated and observed for recovery after 1 week.

Three pot replicates of each genotype were included in the pre-drought screening. Total time needed for a complete test was approx. 36-39 days.

Drought Assay Examination

Once the plants reached the 2 true leaves stage they were thinned to maintain exactly 5 plants per pot. At 10 DAG, plants received nutrition (EC=1.5) and at 15 DAG each pot was moved to a dry tray. From this day onwards the plants did not receive any water. Every day the plants, especially the control (or wild type) (Col-0) were observed for wilting signs. On the 15$^{th}$ day of drought (DOD), Col-0 wilted completely and did not recover upon rehydration. We determined this day as its permanent wilting point (PWP). From this day onwards one replicate from the mutant was rehydrated and observed for recovery signs and pictures were taken. The mutant showed survival for at least 2 days more under drought compared to the control and was subjected for further rigorous screening.

Example 2 Drought Test

Growth Medium

The same mutant and control plants as in Example 1 were grown in similar tray set-up as described above in the pre-screening test. Plants were stressed by withholding water from 15 DAG until the control reached its PWP. During this period every alternate day pots were shuffled within the trays to reduce the position effects and allow uniform evaporation. On day 15 DOD, control plants reached PWP and did not recover upon rehydration. One pot replicate from the mutant was rehydrated everyday from 15 DOD onwards and checked for drought stress recovery. Pictures were taken and recovery was scored. The mutant showed recovery from drought stress for at least 3 days more after the control reached its PWP.

FIG. 1 shows a photograph comparing mutant and control, demonstrating the superior effect of the mutant with respect to resistance to drought stress.

Example 3 Drought Test

Materials and Methods

Plant Material.

A TDNA insertion line with a disrupted AT5G02880 (UPL4) gene (SALK_091246C) was obtained from the Nottingham *Arabidopsis* Stock Centre (NASC). Complementation lines were produced by stable transformation of *Arabidopsis thaliana* plants using floral dip transformation (Bent et al., 2006. Methods Mol. Biol. Vol. 343:87-103). Homologs of the *Arabidopsis thaliana* (AT5G02880) UPL4 gene were identified from several crop species, including *Brassica rapa* (cabbage), *Solanum lycopersicum* (tomato) and *Oryza sativa* (rice) and the model species *Arabidopsis thaliana* (UPL3; A14G38600).

TABLE 1

Homologs of *Arabidopsis thaliana* UPL4 gene and UPL4 protein

| Annotation | Arabidopsis thaliana | Brassica rapa | Solanum lycopersicum | Oryza sativa |
|---|---|---|---|---|
| UPL4 | AT5G02880 (SEQ ID NO: 1 & 2; UPL4) | Br17038 (SEQ ID NO: 5 & 6) | Slg98247 (SEQ ID NO: 9 & 10) | Os05g03100 (SEQ ID NO: 11 & 12) |
|  | AT4G38600 (SEQ ID NO: 3 & 4; UPL3) | Br47159 (SEQ ID NO: 7 & 8) |  |  |

TABLE 2

Percentage of nucleic acid sequence identity between the *Arabidopsis thaliana* UPL4 cDNA sequence (SEQ ID NO: 1) and cDNA sequences of homologues in *Arabidopsis thaliana* (At4g38600 (UPL3); SEQ ID NO: 3), *Brassica rapa* (Br17038; SEQ ID NO: 5 & Br47159; SEQ ID NO: 7), *Solanum lycopersicum* (Slg98247; SEQ ID NO: 9), and *Oryza sativa* (Os05g03100; SEQ ID NO: 11)(first column); and percentage of amino acid sequence identity between the *Arabidopsis thaliana* UPL4 protein sequence (SEQ ID NO: 2) and protein sequences of homologues in *Arabidopsis thaliana* (At4g38600; SEQ ID NO: 4), *Brassica rapa* (Br17038; SEQ ID NO: 6 & Br47159; SEQ ID NO: 8), *Solanum lycopersicum* (Slg98247; SEQ ID NO: 10), and *Oryza sativa* (Os05g03100; SEQ ID NO: 12)(second column).

|  | Nucleotide sequence | Amino acid sequence |
|---|---|---|
| At4g38600 | 62 | 40 |
| Br17038 | 86 | 81 |
| Br47159 | 86 | 80 |
| Slg98247 | 63 | 39 |
| Os05g03100 | 61 | 36 |

Drought Assay.

Wild-type, TDNA knock-out and complementation lines were sown in a replicated blocked design in 50-cell seedlings trays containing a 2:1:1 mix of Metro-Mix 852 soilless medium, fine sand and vermiculite. Planted trays were placed at 4° C. for three days to break dormancy and then transferred to a growth chamber (16 h 22/20° C., 50% rH) for germination and establishment. Complementation lines were sprayed with a glufosinate formulation (20 mg glufosinate, 20 μL Silwet surfactant, 200 mL water) once they had fully expanded cotyledons to assure that only transformed lines were selected. Following this treatment, seedlings in each cell were thinned to a single plant. Once plants reached the 4-6 true leaf stage they were acclimated to greater vapour pressure deficit conditions to promote even drought stress (28/26° C., 25% rH) and unusually small plants were identified for removal prior to drought treatment. Planting trays were soaked with water and then allowed to drain, leaving all cells at pot capacity. Entire trays were watered once half of the wild-type plants in any given tray appeared to be at their permanent wilting point (1.5-2 weeks of drought treatment). Plants were allowed to recover over a few days and survival was recorded, with pre-identified abnormally small plants omitted from further analyses.

Statistical Analysis.

Statistical significance of differing probabilities of survival over this drought treatment was assessed by applying the test of equal or given proportions in the statistical software program, R. The function prop.test was used to test the null hypothesis that the proportions of surviving plants between mutant and wild-type (one-tailed), or alternatively, between insertion mutant lines containing or not containing complementing transgenes (two-tailed), were equal.

Results

FIG. 2 shows the drought resistant phenotype of the UPL4 knockout (*Arabidopsis* At5g02880 insertion mutant) as compared to the drought sensitive phenotype of a control (wild-type) plant.

Figure 3:
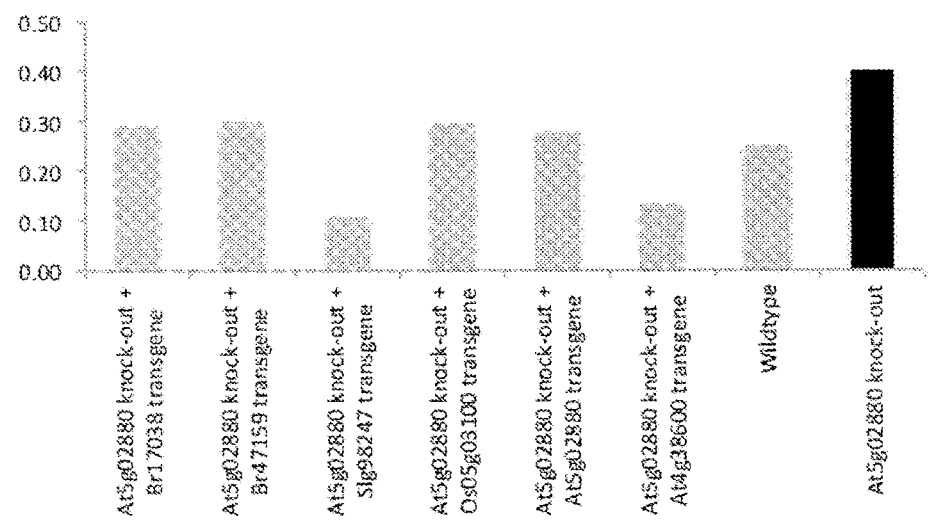
FIG. 3 shows drought survival of At5g02880-insertion mutant (UPL4). The *Arabidopsis thaliana* At5g02880 insertion mutant survived drought significantly better (p<0.05) than wild-type (Col-0) plants or At5g02880 insertion mutants complemented with the coding sequence (CDS) of At5g02880 (SEQ ID NO:1; positive control) and homologs from *Arabidopsis thaliana* (SEQ ID NO:3), *Brassica rapa* (SEQ ID NOs:5 or 7), *Solanum lycopersicum* (SEQ ID NO:9) or *Oryza sativa* (SEQ ID NO:11). This figure demonstrates that an insertion mutation in the UPL4 gene produces a drought resistant phenotype. Moreover, it also indicates that homologs of this gene from monocot and dicot species operate to restore the normal drought-susceptible phenotype. Hence, these homologs perform the same function in drought tolerance in their respective crop species. The observation that both monocot and dicot UPL4 genes can restore drought susceptibility when inserted into the UPL4 insertion mutant of *Arabidopsis* suggests that a reduced activity of the protein encoded by the UPL4 gene renders drought tolerant phenotypes throughout the entire plant kingdom. Hence, prediction of UPL4 (based on homology searches and characteristic domain [HECT] and Armadillo repeat sequences) will allow identification of plant UPL4 homologs in plant species. Subsequently, one can use well-known methods to reduce protein activity of these plant homologs (e.g. mutagenesis, TDNA or transposon insertion, RNAi, etc) to obtain drought resistant plants. Gray bars have significantly lower values (p<0.05) than black bars.

The *Arabidopsis* At5g02880 insertion mutant survived drought significantly better ($p<0.05$) than wild-type (Col-0) plants or At5g02880 insertion mutants complemented with the coding sequence (CDS) of At5g02880 (SEQ ID NO:1; positive control) and homologs from *Arabidopsis thaliana* (SEQ ID NO:3), *Brassica rapa* (SEQ ID NOs: 5 and 7), *Solanum lycopersicum* (SEQ ID NO:9) or *Oryza sativa* (SEQ ID NO:11). FIG. 3 demonstrates that an insertion mutation in the UPL4 gene produces a drought resistant phenotype. Moreover, it also indicates that homologs of this gene from monocot and dicot species operate to restore the normal drought-susceptible phenotype. Hence, these homologs perform the same function in drought tolerance in their respective crop species. The observation that both monocot and dicot UPL4 genes can restore drought susceptibility when inserted into the UPL4 mutant of *Arabidopsis* suggests that a reduced activity of the protein encoded by the UPL4 gene renders drought tolerant phenotypes throughout the entire plant kingdom. Hence, prediction of UPL4 (based on homology searches and characteristic domain [HECT] and Armadillo repeat sequences) will allow identification of plant UPL4 homologs in plant species. Subsequently, one can use well-known methods to reduce protein activity of these plant homologs (e.g. mutagenesis, TDNA or transposon insertion, RNAi, etc) to obtain drought resistant plants. Grey bars have significantly lower values ($p<0.05$) than black bars.

Example 4 Drought Resistance in Tomato

Plant Material

A novel mutation in the tomato gene Solyc10g055450 (SIg98247; SEQ ID NO:9) was generated through EMS screening. The mutation consisted of an amino acid change of valine (hydrophobic properties) to glutamic acid (negatively charged amino acid) (in position 158 of the protein). A segregating M2 population containing homozygous, heterozygous and wild-type allele were used for all drought experiments.

A second mutation was identified in the same tomato gene, causing an amino acid change of aspartic acid (negatively charged amino acid) to glutamic acid (negative charged amino acid) (in position 114 of the protein). Due to the similarity in biochemical properties, this mutation was unlikely to cause significant changes to the protein properties and was therefore used as a negative control in the drought assays. Sift (Ng and Henikoff, 2003—Nucl. Acids Res. 31: 3812-3814) analysis showed that this mutation is likely to be tolerated. A segregating M2 population containing homozygous, heterozygous and wild-type allele were used for all drought experiments.

Drought Assay.

Tomato seedlings that were homozygous, heterozygous or wild-type for the described V158E mutation were grown in 2.5 inch plastic pots containing a 2:1:1 mix of Metro-Mix 852 soilless medium, fine sand and vermiculite in a growth chamber (16 h 22/20° C., 50% rH. Upon establishment, seedlings were acclimated to greater vapor pressure deficit conditions to promote even drought stress (28/26° C., 25% rH). Pots were soaked with water and then allowed to drain, leaving all plants at pot capacity. Plants were subjected to a drought stress period of 1 week and then watered and allowed to recover for 24 h, when survival was assessed.

Statistical Analysis.

Statistical significance of differing probabilities of survival over this drought treatment was assessed by apply the test of equal or given proportions in the statistical software program, R. The function prop.test was used to test the null hypothesis that the proportions of surviving plants between homozygous and wild-type mutants (one-tailed) were equal.

Results

Figure 4:
FIG. 4 shows the drought phenotype of a tomato (*Solanum lycopersicum*) UPL4-mutant. A segregating M2 population containing homozygous, heterozygous and wild-type allele were used for a drought experiment. The photograph—taken 21 days after initiation of the drought treatment—shows a wild-type tomato plant (right) and a plant carrying the V158E mutation in SIg98247 (left). Drought tolerant phenotype and survival of the drought treatment was significantly better (p<0.1) for the plant carrying the V158E mutation in SIg98247 compared to the wild-type allele, indicating that this alteration of the protein leads to a drought tolerant phenotype in tomato.

Tomato plants, homozygous for the V158E mutation in SIg98247 survived the drought treatment significantly better ($p<0.1$) compared to the wild-type allele, indicating that this alteration of the protein leads to a drought tolerant phenotype in tomato (FIG. 4). As expected the additional mutation in SIg98247 (D114E) did not show any drought related phenotype (all plants from the segregating M2 population were equally drought susceptible).

The invention claimed is:

1. A method for identifying one or more plants with drought resistance, comprising determining the sequence of at least part of the endogenous UPL4 gene of said plants; identifying one or more plants having a mutation in the endogenous UPL4 gene resulting in impaired expression of functional UPL4 protein, wherein the functional UPL4 protein comprises the amino acid sequence of any of SEQ ID NO: 2, 6, 8, and 12, wherein the functional UPL4 protein has ubiquitin-protein ligase activity; and exposing the identified one or more plants to drought stress and assaying the plants for drought resistance to select a plant exhibiting improved drought resistance.

2. The method according to claim 1, wherein the one or more plants are *Arabidopsis thaliana*.

3. The method according to claim 1, wherein the one or more plants are *Solanum lycopersicum, Brassica rapa*, and *Oryza sativa*.

4. The method according to claim 1, wherein the one or more plants are part of a heterogenic population.

5. The method according to claim 4, wherein the heterogenic population is provided by subjecting plant cells to a mutagen that introduces random mutations.

6. The method according to claim 1, wherein the one or more plants have been subjected to genetic modification targeting the UPL4 gene sequence.

7. The method according to claim 1, wherein the at least one mutation involves an insertion, a deletion and/or substitution of at least one nucleotide.

8. The method according to claim 1, wherein impaired expression comprises gene silencing.

* * * * *

SEQUENCE LISTING

```
<160> NUMBER OF SEQ ID NOS: 12

<210> SEQ ID NO 1
<211> LENGTH: 4509
<212> TYPE: DNA
<213> ORGANISM: Arabidopsis thaliana
```

```
<400> SEQUENCE: 1
atggagaaca gaggccagaa acgaatggag gttgtggaag agttacctgc tgataagaga      60
gcttgtaact ctcaggattt tagaccaagc acatccggat catctgttca agctcaagct     120
aatgatacga atccaggaca tgaaaacgtt gacgctgata tggatacttc ttcatctgct     180
tcgccttcga gtcgatcaga tgaagaagaa caggaagagc aggataagga ggattcggac     240
tatggatctt gcgattctga tgaggaagat ccgaggcaga gggtgcttca ggattaccag     300
aggcagagat catctggtga tcatgggaaa ttgaagtctc ttttgttgaa tttgactgga     360
gaaactgatc cttctggaca gttatccagg ctcactgagt tatgtgaagt gttgtcattt     420
tctactgaag aatcgctgtc cagtgttatg gccaacatgc tatcaccggt gcttgtaaag     480
ttagctaagc atgagaacaa tgcagatatt atgctcctcg caattagagc tattacttat     540
ttgtgtgatg tttatccgcc gtcagtagaa ttccttgtaa gacatgatac cattcctgct     600
ctctgccaaa gacttttgac tattgagtac ttggacgttg ctgagcagtg tttgcaagca     660
cttgagaaaa tatcccgaga tgagccggta gcctgcttga atgctggagc aattatggca     720
gtgctttcgt ttattgattt cttctcaaca agcatacaga gagtcgcaat ttctactgtg     780
gtcaatatat gtaagcagct ttcttctgag tctccctcgc cttttcatgga tgctgttcca     840 atattatgca ctcttcttca atatgaagat cgacagctgg tcgagaatgt ggctatttgc     900
ttgacaaaaa tagcagatca agccagtgag tcaccggcaa tgttggatca actgtgtagg     960
catggactaa ttaatgaatc aacacatctc ttaaacttga atagccgcac tacccctatct    1020 caacctgtct acaatggtgt gattggaatg ctaagaaaac tatcttctgg ttcagcttta    1080
gctttcagaa cgttatatga gcttaacatt ggctacagtt taaaagaaat catgtccacg    1140
tatgacattt ctcattcagt gtcttctaca catcctatca atgcatgttc taatcaggtg    1200
catgaagtcc tgaagttggt gattgagctt cttccagctt cacccgtaga ggataatcag    1260
ctggcatcgg aaaaggaaag ttttctcgtc aatcagcctg atcttttgca acaatttgga    1320
agagacatgc ttcctgtcat gattcaggtg ctaaactctg gagctaacgt atatgtttct    1380
tatggttgcc tatcagcaat tcacaagctg acttgcttga gtaagtccgg tgatattgtc    1440
gagttactga agaacaccaa catgtcaagt gttttggctg gcattctgtc aaggaaggat    1500
catcatgtaa ttgtagtagc actacaggtt gcggaagtgc ttcttgagaa atacagagat    1560 actttttga attctttat aaaggaaggt gttttttcg cgattgaagc actcttaagt    1620
tctgatagag ggcaacaaaa tcagggatca gctgaccttt cacaaaagcc tgttacaaaa    1680
gagattgtga atgcttgtg ccaatctttt gaaagatcgc tatcctcttc ttcacaaact    1740
tgtaagattg aaaaggattc tgtctacgtt cttgcaacac gtatcaagga gggtttcttt    1800
ggacctgagg tattcaactc tgagaaaggc ttgacagatg tcctccaaaa cctcaagaac    1860
ttgtcggtag cacttagcga gttgatgact gtacccattg atgcgcatgt cctgcatgat    1920
gagaaattct tctcaatatg gaaccaaatc atggaaaggc tgaatggaag ggaatctgtg    1980
tccacttttg aattcattga gagcggagtt gtaaagtcac tggcaagtta tctttctaat    2040
ggactctatc aaaggaaact tagcaaaggg ggtcctgaat gtgatagttt accatttatt    2100
ggtaagagat ttgaggtgtt cacaagattg ctttggtctg atggagaggc aacttcatcc    2160
ttgttaatac agaagctcca aaattcccct tcttctttgg aaaacttccc aattgtccta    2220
agccaatttt tgaagcagaa gaactcattt gcggctattc caaatgggcg ttgcactagt    2280
tatccatgcc taaaagttcg ttttctgaaa gcagagggg agacttcttt gcgtgattac    2340
```

```
tcccaagact tgtcactgt tgacccactt tgctatttgg atgctgtcga tcaatacttg      2400
tggcctaaag ttaatataga acctatagat tctgtggaag caaaagatca agctatagaa      2460
tgtcaatctt ctcaattgca gtcaacttcg atatcttgtc aagctgaaag ctcaagtcct      2520
atggagattg acagtgagtc ttctgatgcg tctcagttgc agggatctca agtggaagat      2580
cagacgcaac ttccaggaca cagaatgct tcctcctctg aaacctcctc tgaaaaagag       2640
gatgcggtac ctagactttt gtttcgtctc gaagggcttg aactagaccg ttctttgaca      2700
gtatatcagg cgattctctt gcacaaacta aaatcagaaa gtgaagcaac caacgattcg      2760
aagctgagtg accccacaa catcacttat gaaaggtctg cacaacttgg ggattctcgt       2820
gaaaatctgt ttccacctgg atctatggaa gatgatgagt atcgcccgtt cttgtcctat      2880
ttgtttactc atagcttgc tttgcgcctg aaggggtcaa gtcatcctcc gtatgacata       2940
ttgtttcttc ttaagagtct ggagggcatg aacagatttc tctttcacct gatttctctt      3000
gaacggatta atgcttttgg tgaaggtagg ctagagaatt tggatgatct gagggtacaa      3060
gttcgtcctg tgccacattc tgaatttgtt agcagtaagc ttacagagaa gttagagcag      3120
cagcttcgtg attctttgc tgtgtcaacc tgcggtctgc caccatggtt taatgatcta       3180
atggattcat gtccgtgttt atttagtttt gaagccaagt ctaaatactt ccgacttgca      3240
gcctttggtt cacagaaaat ccgtcatcat ccacagcacc ttagcagttc aaatgttcat      3300
ggcgaagcgc gcccagtgac tggtagttta cctcgtaaaa agttcttagc ttgccgtgaa      3360
aacattctag agtctgctgc caaaatgatg gagttatatg aaaccagaa ggtggtcatt       3420 gaggttgaat acagtgaaga gtcgggact ggtcttgggc caacactgga gttctatacg       3480
cttgtcagta gggcatttca aaatcccgat cttggtatgt ggagaaatga ttgtagtttt      3540
attgttggaa agccagtcga acactcggga gttttggcat cttcttcagg actctttcca      3600
cgcccttggt caggtacatc aactacgtca gatgtgctgc agaaatttgt cctcttgggg      3660
acagtggtag caaaggcttt acaagatgga cgagtcttag accttccact ttccaaagcc      3720
ttctacaaat taattctcgg acaggagttg agttcatttg acatccactt cgttgaccct      3780
gaactttgta aaacactggt ggaattgcaa gctctggtac gtaggaaaaa gcttttcgct      3840
gaagcacatg gtgattccgg agcagccaag tgtgatttaa gtttccatgg aacaaagatt      3900
gaggaccttt gtcttgaatt tgcattgcct ggctacacgg attatgatct cgctccctat      3960
tctgcaaatg atatggtaaa tttggataac ctcgaggaat atatcaaggg tattgtcaat      4020
gccacagtat gtaatgggat ccaaaaacaa gtggaagcat ttcggtctgg atttaatcag      4080
gttttctcta ttgaacatct tcggatattc aacgaagagg agctggaaac tatgctgtgt      4140
ggagaatgtg atctctttag tatgaatgaa gtcttggatc acatcaagtt tgatcatgga      4200
tatacttcta gcagcccacc agttgaatat ttattgcaga ttctgcatga gtttgataggg     4260 gagcaacaac gagcctttt gcaatttgta acaggatctc cccggttacc tcatggtggt       4320
ttggcgtctc tcagtcccaa actaacaatc gtccgcaagc atggtagcga ttcttcagat      4380
actgacctcc ctagtgtgat gacatgcgcc aattatctga agcttcctcc ttattcatcc      4440
aaagagaaga tgaaggagaa gctgatttat gccataacgg aaggtcaagg ttccttccat      4500
ctctcttaa                                                              4509
```

<210> SEQ ID NO 2
<211> LENGTH: 1502
<212> TYPE: PRT
<213> ORGANISM: Arabidopsis thaliana

<400> SEQUENCE: 2

```
Met Glu Asn Arg Gly Gln Lys Arg Met Glu Val Val Glu Leu Pro
1               5                   10                  15

Ala Asp Lys Arg Ala Cys Asn Ser Gln Asp Phe Arg Pro Ser Thr Ser
            20                  25                  30

Gly Ser Ser Val Gln Ala Gln Ala Asn Asp Thr Asn Pro Gly His Glu
            35                  40                  45

Asn Val Asp Ala Asp Met Asp Thr Ser Ser Ala Ser Pro Ser Ser
        50                  55                  60

Arg Ser Asp Glu Glu Gln Glu Glu Gln Asp Lys Glu Asp Ser Asp
65                  70                  75                  80

Tyr Gly Ser Cys Asp Ser Asp Glu Glu Asp Pro Arg Gln Arg Val Leu
                85                  90                  95

Gln Asp Tyr Gln Arg Gln Arg Ser Ser Gly Asp His Gly Lys Leu Lys
            100                 105                 110

Ser Leu Leu Leu Asn Leu Thr Gly Glu Thr Asp Pro Ser Gly Gln Leu
            115                 120                 125

Ser Arg Leu Thr Glu Leu Cys Glu Val Leu Ser Phe Ser Thr Glu Glu
    130                 135                 140

Ser Leu Ser Ser Val Met Ala Asn Met Leu Ser Pro Val Leu Val Lys
145                 150                 155                 160

Leu Ala Lys His Glu Asn Asn Ala Asp Ile Met Leu Leu Ala Ile Arg
                165                 170                 175

Ala Ile Thr Tyr Leu Cys Asp Val Tyr Pro Pro Ser Val Glu Phe Leu
            180                 185                 190

Val Arg His Asp Thr Ile Pro Ala Leu Cys Gln Arg Leu Leu Thr Ile
            195                 200                 205

Glu Tyr Leu Asp Val Ala Glu Gln Cys Leu Gln Ala Leu Glu Lys Ile
    210                 215                 220

Ser Arg Asp Glu Pro Val Ala Cys Leu Asn Ala Gly Ala Ile Met Ala
225                 230                 235                 240

Val Leu Ser Phe Ile Asp Phe Phe Ser Thr Ser Ile Gln Arg Val Ala
                245                 250                 255

Ile Ser Thr Val Val Asn Ile Cys Lys Gln Leu Ser Ser Glu Ser Pro
            260                 265                 270

Ser Pro Phe Met Asp Ala Val Pro Ile Leu Cys Thr Leu Leu Gln Tyr
            275                 280                 285

Glu Asp Arg Gln Leu Val Glu Asn Val Ala Ile Cys Leu Thr Lys Ile
    290                 295                 300

Ala Asp Gln Ala Ser Glu Ser Pro Ala Met Leu Asp Gln Leu Cys Arg
305                 310                 315                 320

His Gly Leu Ile Asn Glu Ser Thr His Leu Leu Asn Leu Asn Ser Arg
                325                 330                 335

Thr Thr Leu Ser Gln Pro Val Tyr Asn Gly Val Ile Gly Met Leu Arg
            340                 345                 350

Lys Leu Ser Ser Gly Ser Ala Leu Ala Phe Arg Thr Leu Tyr Glu Leu
            355                 360                 365

Asn Ile Gly Tyr Ser Leu Lys Glu Ile Met Ser Thr Tyr Asp Ile Ser
    370                 375                 380

His Ser Val Ser Ser Thr His Pro Ile Asn Ala Cys Ser Asn Gln Val
385                 390                 395                 400

His Glu Val Leu Lys Leu Val Ile Glu Leu Leu Pro Ala Ser Pro Val
                405                 410                 415
```

```
Glu Asp Asn Gln Leu Ala Ser Glu Lys Glu Ser Phe Leu Val Asn Gln
            420                 425                 430

Pro Asp Leu Leu Gln Gln Phe Gly Arg Asp Met Leu Pro Val Met Ile
        435                 440                 445

Gln Val Leu Asn Ser Gly Ala Asn Val Tyr Val Ser Tyr Gly Cys Leu
    450                 455                 460

Ser Ala Ile His Lys Leu Thr Cys Leu Ser Lys Ser Gly Asp Ile Val
465                 470                 475                 480

Glu Leu Leu Lys Asn Thr Asn Met Ser Ser Val Leu Ala Gly Ile Leu
                485                 490                 495

Ser Arg Lys Asp His His Val Ile Val Ala Leu Gln Val Ala Glu
                500                 505                 510

Val Leu Leu Glu Lys Tyr Arg Asp Thr Phe Leu Asn Ser Phe Ile Lys
        515                 520                 525

Glu Gly Val Phe Phe Ala Ile Glu Ala Leu Leu Ser Ser Asp Arg Gly
    530                 535                 540

Gln Gln Asn Gln Gly Ser Ala Asp Leu Ser Gln Lys Pro Val Thr Lys
545                 550                 555                 560

Glu Ile Val Lys Cys Leu Cys Gln Ser Phe Glu Arg Ser Leu Ser Ser
                565                 570                 575

Ser Ser Gln Thr Cys Lys Ile Glu Lys Asp Ser Val Tyr Val Leu Ala
                580                 585                 590

Thr Arg Ile Lys Glu Gly Phe Phe Gly Pro Glu Val Phe Asn Ser Glu
        595                 600                 605

Lys Gly Leu Thr Asp Val Leu Gln Asn Leu Lys Asn Leu Ser Val Ala
    610                 615                 620

Leu Ser Glu Leu Met Thr Val Pro Ile Asp Ala His Val Leu His Asp
625                 630                 635                 640

Glu Lys Phe Phe Ser Ile Trp Asn Gln Ile Met Glu Arg Leu Asn Gly
                645                 650                 655

Arg Glu Ser Val Ser Thr Phe Glu Phe Ile Glu Ser Gly Val Val Lys
                660                 665                 670

Ser Leu Ala Ser Tyr Leu Ser Asn Gly Leu Tyr Gln Arg Lys Leu Ser
        675                 680                 685

Lys Gly Gly Pro Glu Cys Asp Ser Leu Pro Phe Ile Gly Lys Arg Phe
    690                 695                 700

Glu Val Phe Thr Arg Leu Leu Trp Ser Asp Gly Glu Ala Thr Ser Ser
705                 710                 715                 720

Leu Leu Ile Gln Lys Leu Gln Asn Ser Leu Ser Leu Glu Asn Phe
                725                 730                 735

Pro Ile Val Leu Ser Gln Phe Leu Lys Gln Lys Asn Ser Phe Ala Ala
            740                 745                 750

Ile Pro Asn Gly Arg Cys Thr Ser Tyr Pro Cys Leu Lys Val Arg Phe
        755                 760                 765

Leu Lys Ala Glu Gly Glu Thr Ser Leu Arg Asp Tyr Ser Gln Asp Phe
    770                 775                 780

Val Thr Val Asp Pro Leu Cys Tyr Leu Asp Ala Val Asp Gln Tyr Leu
785                 790                 795                 800

Trp Pro Lys Val Asn Ile Glu Pro Ile Asp Ser Val Glu Ala Lys Asp
                805                 810                 815

Gln Ala Ile Glu Cys Gln Ser Ser Gln Leu Gln Ser Thr Ser Ile Ser
            820                 825                 830
```

-continued

Cys Gln Ala Glu Ser Ser Pro Met Glu Ile Asp Ser Glu Ser Ser
            835                 840                 845

Asp Ala Ser Gln Leu Gln Gly Ser Gln Val Glu Asp Gln Thr Gln Leu
850                 855                 860

Pro Gly Gln Gln Asn Ala Ser Ser Ser Glu Thr Ser Ser Glu Lys Glu
865                 870                 875                 880

Asp Ala Val Pro Arg Leu Leu Phe Arg Leu Glu Gly Leu Glu Leu Asp
                885                 890                 895

Arg Ser Leu Thr Val Tyr Gln Ala Ile Leu Leu His Lys Leu Lys Ser
            900                 905                 910

Glu Ser Glu Ala Thr Asn Asp Ser Lys Leu Ser Gly Pro His Asn Ile
            915                 920                 925

Thr Tyr Glu Arg Ser Ala Gln Leu Gly Asp Ser Arg Glu Asn Leu Phe
            930                 935                 940

Pro Pro Gly Ser Met Glu Asp Asp Glu Tyr Arg Pro Phe Leu Ser Tyr
945                 950                 955                 960

Leu Phe Thr His Arg Leu Ala Leu Arg Leu Lys Gly Ser Ser His Pro
                965                 970                 975

Pro Tyr Asp Ile Leu Phe Leu Leu Lys Ser Leu Glu Gly Met Asn Arg
            980                 985                 990

Phe Leu Phe His Leu Ile Ser Leu Glu Arg Ile Asn Ala Phe Gly Glu
            995                 1000                1005

Gly Arg Leu Glu Asn Leu Asp Asp Leu Arg Val Gln Val Arg Pro
    1010                1015                1020

Val Pro His Ser Glu Phe Val Ser Ser Lys Leu Thr Glu Lys Leu
    1025                1030                1035

Glu Gln Gln Leu Arg Asp Ser Phe Ala Val Ser Thr Cys Gly Leu
    1040                1045                1050

Pro Pro Trp Phe Asn Asp Leu Met Asp Ser Cys Pro Cys Leu Phe
    1055                1060                1065

Ser Phe Glu Ala Lys Ser Lys Tyr Phe Arg Leu Ala Ala Phe Gly
    1070                1075                1080

Ser Gln Lys Ile Arg His His Pro Gln His Leu Ser Ser Ser Asn
    1085                1090                1095

Val His Gly Glu Ala Arg Pro Val Thr Gly Ser Leu Pro Arg Lys
    1100                1105                1110

Lys Phe Leu Ala Cys Arg Glu Asn Ile Leu Glu Ser Ala Ala Lys
    1115                1120                1125

Met Met Glu Leu Tyr Gly Asn Gln Lys Val Val Ile Glu Val Glu
    1130                1135                1140

Tyr Ser Glu Glu Val Gly Thr Gly Leu Gly Pro Thr Leu Glu Phe
    1145                1150                1155

Tyr Thr Leu Val Ser Arg Ala Phe Gln Asn Pro Asp Leu Gly Met
    1160                1165                1170

Trp Arg Asn Asp Cys Ser Phe Ile Val Gly Lys Pro Val Glu His
    1175                1180                1185

Ser Gly Val Leu Ala Ser Ser Gly Leu Phe Pro Arg Pro Trp
    1190                1195                1200

Ser Gly Thr Ser Thr Thr Ser Asp Val Leu Gln Lys Phe Val Leu
    1205                1210                1215

Leu Gly Thr Val Val Ala Lys Ala Leu Gln Asp Gly Arg Val Leu
    1220                1225                1230

Asp Leu Pro Leu Ser Lys Ala Phe Tyr Lys Leu Ile Leu Gly Gln

```
      1235               1240               1245
Glu Leu Ser Ser Phe Asp Ile His Phe Val Asp Pro Glu Leu Cys
    1250                1255               1260

Lys Thr Leu Val Glu Leu Gln Ala Leu Val Arg Arg Lys Lys Leu
    1265                1270               1275

Phe Ala Glu Ala His Gly Asp Ser Gly Ala Ala Lys Cys Asp Leu
    1280                1285               1290

Ser Phe His Gly Thr Lys Ile Glu Asp Leu Cys Leu Glu Phe Ala
    1295                1300               1305

Leu Pro Gly Tyr Thr Asp Tyr Asp Leu Ala Pro Tyr Ser Ala Asn
    1310                1315               1320

Asp Met Val Asn Leu Asp Asn Leu Glu Glu Tyr Ile Lys Gly Ile
    1325                1330               1335

Val Asn Ala Thr Val Cys Asn Gly Ile Gln Lys Gln Val Glu Ala
    1340                1345               1350

Phe Arg Ser Gly Phe Asn Gln Val Phe Ser Ile Glu His Leu Arg
    1355                1360               1365

Ile Phe Asn Glu Glu Glu Leu Glu Thr Met Leu Cys Gly Glu Cys
    1370                1375               1380

Asp Leu Phe Ser Met Asn Glu Val Leu Asp His Ile Lys Phe Asp
    1385                1390               1395

His Gly Tyr Thr Ser Ser Ser Pro Pro Val Glu Tyr Leu Leu Gln
    1400                1405               1410

Ile Leu His Glu Phe Asp Arg Glu Gln Gln Arg Ala Phe Leu Gln
    1415                1420               1425

Phe Val Thr Gly Ser Pro Arg Leu Pro His Gly Gly Leu Ala Ser
    1430                1435               1440

Leu Ser Pro Lys Leu Thr Ile Val Arg Lys His Gly Ser Asp Ser
    1445                1450               1455

Ser Asp Thr Asp Leu Pro Ser Val Met Thr Cys Ala Asn Tyr Leu
    1460                1465               1470

Lys Leu Pro Pro Tyr Ser Ser Lys Glu Lys Met Lys Glu Lys Leu
    1475                1480               1485

Ile Tyr Ala Ile Thr Glu Gly Gln Gly Ser Phe His Leu Ser
    1490                1495               1500

<210> SEQ ID NO 3
<211> LENGTH: 5667
<212> TYPE: DNA
<213> ORGANISM: Arabidopsis thaliana

<400> SEQUENCE: 3
atggaaactc ggagccgcaa gcgggcggag gcgacctcag ctgccccatc ttcttcttct      60
tcttctcctc ctcctcctcc ctctgcctct ggtcccacca cccgcagcaa acgcgctcgt     120
ctttcttctt cttcttcttc ctcacttgcc cccactcctc cttcttcctc caccaccacc     180
cgctctcgtt cttctcgctc tgccgccgcc gctgctccca tggacacctc caccgactct     240
tctggatttc gccgaggcgg acgtggtaac aggggaaaca acaacgataa ttctgacaaa     300
ggtaaggaga aggaacatga cgttaggatt agggagcgtg aaagagaaag agaccgagcc     360
agagaacaac tcaacatgga tgctgccgcc gccgctgcta ggagcgctga cgaggatgac     420
gacaatgaca gtgaggatgg caacggcggt tcatgcatc ctaacatgag ctctgcgagc     480
agtgctttac aaggcttgct caggaagctc ggtgctggat tggatgactt gcttccttct     540
```

```
tccggtatcg gctctgcttc ttcctcccac ttgaatggaa ggatgaagaa gattctctct      600
ggcttgcgcg ctgaaggaga agagggaaaa caggtcgagg cttaaccca gctttgtgag       660
atgttatcca ttgggaccga agactcgctt agcaccttct ctgttgattc cttcgtccca      720
gttcttgtcg gtctacttaa ccatgaaagc aatcccgaca ttatgcttct tgctgccagg      780
gctcttaccc atctatgtga tgtcttgccg tcttcttgtg ctgctgttgt acattacggg      840
gcagtttcat gcttggtggc cagattgcta accatagaat acatggactt ggcggaacag      900
tctctgcaag ctctcaaaaa gatatctcag gagcacccaa ctgcctgttt gcgagctggt      960
gctcttatgg ctgtgctctc gtatctggat tccttctcca ctggtgttca gcgcgtagca     1020
ctatctactg ctgccaacat gtgcaagaaa ctaccttctg atgcatctga ttatgttatg     1080
gaagctgtac ctttgctgac aaacctactt cagtatcatg attcgaaggt tttggaatat     1140
gcttctatct gtctgactcg aattgctgaa gcatttgcac cgtatcccga gaaattagat     1200
gaattatgta accatggcct ggtgacgcaa gctgcgtctc ttatttccac gagcaattca     1260
ggaggtgggc aagcatctct tagtgtgtca acatacacgg ggttaatccg attactttct     1320
acctgtgcga gcgggtcacc tcttggattc aggacattac ttcttcttgg tattagtagc     1380
attcttaagg atattctgtt gggttctggg gtctctgcta atgcatctgt atccccagca     1440
ctgagccggc ctgcagatca gatttatgag atagtcaacc tagcgaatga gctcctccct     1500
ccattgccag aaggagttat ctctcttcct actagcacaa acgctcttgt gaaaggttca     1560
tgccaaaaga aatctagtcc aagtacttca ggaaaacaag aagatattct aaaaatttca     1620
ccaagagaaa aattacttgg tgatcaacct gaacttctgc agcagtttgg attggatctt     1680
cttccagttt tagtgcagat ctatggttct agtgtcaatg gtacgattcg ccataaatgt     1740
ctctcagtca ttgaaaagtt gatgtatttc agcagttcag aaatgattca atctctaatt     1800
ggtgacacaa atatttcgag cttcttggct ggtgtcttgg catggaaaga cccacaggtc     1860
ttggttcctg ctctacaagt tgcagagatt ttgatggaaa agcttcctga acattctcg      1920
aaagtgtttg tgagggaagg ggtagtccat gctgtagatc aacttgtctt ggttggtaaa     1980
ccatcccatg cctcacctac tgataaggac aatgactgtg tacccggatc tgcacgatct     2040
aggcgttata gacggcgcag tagtaatgcc aattccgatg gaaaccagtc ggaagagcct     2100
aagaatcctg cgtcccttac catagggca aaccataatt cccttgatac tcctacagct      2160
agcttcatgc taagggaaac agttagttcc tgcgccaaag cattcaaaga caagtacttc     2220
ccgtctgatg gtggggatgt tgatgttgga gttacagatg atcttttaca tctgaagaat     2280
cttttgcacga agctaactgc tggtatagat gatcataaag tgaaaggaaa gggaaaatct    2340
aaagcctctg ggccattcct tggcgatttc tctgctagca aggaagagta cttgattggt     2400
gtcatttctg agatacttgg cgagataagt aaagggatg gtgtctcaac ttttgagttt       2460
attggcagtg gtgtggttgc agcattgctt aactatttt cttgtggata cttttccaaa      2520
gagaagatct ccgaacttaa tttgcccaaa cttcgccagg agggactcag aaggttaaaa     2580
gcttttctag aagtcgctct tccttttgat ggtaatgagg gaaaggtccc tcctatgaca     2640
gttttgattc agaaacttca aaatgcttta tcgtcactgg agcgctttcc tgttgtcctt     2700
agccatccct caaggtcact aagtggaagt gctcggctct cctcgggttt gagtgctttg     2760
gcacatcctt taaagttgcg attatgccga gcatctggag agaaaacact acgtgattac     2820
tcctccaata ttgtacttat agatccattg gcaagcttag cagcagtgga ggaatttctg     2880
tggccccgag ttcaacggag tgaatctgct ctgaagccgg cagcgcctat tggcaataca     2940
```

```
gagccaggca cgttacctag cggtgctggt gtttcatcac catcttcgtc aactccagct    3000
tcaaccactc gtcgtcattc ttctagatct cgatcggcaa ttaacatcgg tgatacttca    3060
aagaaagatc ctgtgcatga gaaaggtacc agctcatcga aaggaaaagg taaaggcgtt    3120
atgaaaccgg ctcaggcgga taaggggcct caaacaagga gcaatgctca aaagagagct    3180
gttcttgaca aagatactca aatgaaacca gctagcggag actccagttc tgaggatgag    3240
gaattggaaa tatccccagt cgacattgat gatgccttgg tgattgaaga ggatgacatt    3300
tctgatgatg aagatgatga taatgaagat gttttggatg acagtcttcc catgtgcacg    3360
cctgataaag tccatgatgt gaaattggcg gactcagtgg atgatgatgg tctagcaacc    3420
agcggccgac aaatgaatcc agcttctgga ggcactagtg gagccgcagc agcaagggca    3480
tctgattcta ttgatactgg cattgggaat tcctatggtt ctagaggtgc actctccttt    3540
gctgctgcag cgatggctgg gcttggagct gccagtggta gaggtatcag gggaagtagg    3600
gacttgcatg gacgtaccct aaatcgaagt tcagatgagc cctctaagtt gatatttact    3660
gcggcaggaa acaacttag taggcatttg acgatttatc aggctgtaca gcgacaactt    3720
atgctagatg aagatgatga tgacaggttt ggtggcagtg atctagtctc aagtgatgga    3780
agcagattca atgatattta caccatcatg taccagaggc cagacagcca agtgaatagg    3840
ttgtctgttg gtggagcaag ttctaccaca ccgtcaaaat ccacgaaatc tgctactacc    3900
aattccagtg tagaatctca gtcacatagg gcatctcttt tggatagtat cttacaaggg    3960
gagcttccat gcgaccttga gaagtcgaat tctacatata atgttctggc actgttacgt    4020
gtattagagg gtttaaatca gctttgccct cgtttaagag cccaaactct ttccgatcgt    4080
tttgcagagg gtaaaattac aagtctagat gatctgagta caactgctgc taaggttcct    4140
cttgatgaat ttgtcaatag caaacttaca cccaaattgg ctcgacaaat ccaggatgcg    4200
cttgctttgt gcagtggaag tcttccctct tggtgctacc agttgactag agcatgccca    4260
tttttgtttc cgtttcaaac ccggagacag tatttctact cgactgcttt tgggttgtct    4320
cgtgcattga atcgtttgca gcagcagcaa ggtgctgacg gcagtgggtc tacaaatgaa    4380
cgagagatga gaataggag attgcagcgc cagaaagtcc gtgtatcccg aaataggata    4440
ttagattctg ctgcaaaagt tatgagatg tattctagcc agaaagctgt gcttgaagta    4500
gaatattttg gtgaagttgg tactggtcta ggccctaccc ttgagtttta cacacttcta    4560
agccatgatc tgcaaaaggc ttccctaggg atgtggagat caagttctgg tgacaaggta    4620
tctatgcaaa ttgtagagata tgagattgaa gacggaaaac catctgcagc taacagagat    4680
atagttctgg caccacttgg attgtttcct cggccttggc cctcaacagc tgacatatct    4740
gaaggtggtc agtttcataa agtcattgaa tatttccgcc ttttagggcg tgtgatggcc    4800
aaagcacttc aagatggacg gctattggac gtcccattga gtacagcgtt ttataaactt    4860
attcttggtc aagagcttga tttgcatgat attgtattat ttgacgctga acttggcaag    4920
accttgcaag agctgcgtgt tgttgttgcc cgcaagcact atctggaggg agtaggtggt    4980
gacaatagca gcacgatttc tgatttatgt ttacgtggat gccgaataga agatctctcc    5040
ttggaattca cgctacctgg ctatcctgag tacatcctga gatcaggaga tgaaattgtt    5100
gatattacta atcttgagga gtatatatcc cttgtcgttg atgctactgt caagagagga    5160
gtcactcggc agatcgaagc cttcagatct ggattcaatc aggtgtttga cataacatct    5220
ctacaaatat tcaccccttc tgagctggac tatttgctgt gtggtcgtag agagttgtgg    5280
```

```
gaggtggaga ctcttgctga acatatcaaa tttgatcatg ggtataatgc caaaagtccg    5340
gcaatcatta acttactgga gatcatggga gaacttacag cagatcagca gagggctttc    5400
tgccaatttg taactggagc tcctaggctt cctcctggtg gcttagctgt tctgaaccca    5460
aagcttacga ttgtgagaaa gcactcatcg acctcaagtg cagcagccaa cggagcaggg    5520
gcttcggaga cagcagatga tgatttgccc agtgtcatga cttgcgcaaa ctaccttaaa    5580
ctccctcctt attctacaaa ggaaatcatg tacaagaaac tgctctacgc catcaacgaa    5640
gggcaaggat cgttcgacct ctcataa                                       5667
```

<210> SEQ ID NO 4
<211> LENGTH: 1888
<212> TYPE: PRT
<213> ORGANISM: Arabidopsis thaliana

<400> SEQUENCE: 4

```
Met Glu Thr Arg Ser Arg Lys Arg Ala Glu Ala Thr Ser Ala Ala Pro
1               5                   10                  15

Ser Ser Ser Ser Ser Ser Pro Pro Pro Pro Ser Ala Ser Gly Pro
                20                  25                  30

Thr Thr Arg Ser Lys Arg Ala Arg Leu Ser Ser Ser Ser Ser Ser
                35                  40                  45

Leu Ala Pro Thr Pro Pro Ser Ser Ser Thr Thr Thr Arg Ser Arg Ser
 50                  55                  60

Ser Arg Ser Ala Ala Ala Ala Pro Met Asp Thr Ser Thr Asp Ser
65                  70                  75                  80

Ser Gly Phe Arg Arg Gly Gly Arg Gly Asn Arg Gly Asn Asn Asn Asp
                85                  90                  95

Asn Ser Asp Lys Gly Lys Glu Lys Glu His Asp Val Arg Ile Arg Glu
                100                 105                 110

Arg Glu Arg Glu Arg Asp Arg Ala Arg Glu Gln Leu Asn Met Asp Ala
                115                 120                 125

Ala Ala Ala Ala Ala Arg Ser Ala Asp Glu Asp Asp Asn Asp Ser
        130                 135                 140

Glu Asp Gly Asn Gly Gly Phe Met His Pro Asn Met Ser Ser Ala Ser
145                 150                 155                 160

Ser Ala Leu Gln Gly Leu Leu Arg Lys Leu Gly Ala Gly Leu Asp Asp
                165                 170                 175

Leu Leu Pro Ser Ser Gly Ile Gly Ser Ala Ser Ser Ser His Leu Asn
                180                 185                 190

Gly Arg Met Lys Lys Ile Leu Ser Gly Leu Arg Ala Glu Gly Glu Glu
        195                 200                 205

Gly Lys Gln Val Glu Ala Leu Thr Gln Leu Cys Glu Met Leu Ser Ile
        210                 215                 220

Gly Thr Glu Asp Ser Leu Ser Thr Phe Ser Val Asp Ser Phe Val Pro
225                 230                 235                 240

Val Leu Val Gly Leu Leu Asn His Glu Ser Asn Pro Asp Ile Met Leu
                245                 250                 255

Leu Ala Ala Arg Ala Leu Thr His Leu Cys Asp Val Leu Pro Ser Ser
                260                 265                 270

Cys Ala Ala Val Val His Tyr Gly Ala Val Ser Cys Leu Val Ala Arg
        275                 280                 285

Leu Leu Thr Ile Glu Tyr Met Asp Leu Ala Glu Gln Ser Leu Gln Ala
        290                 295                 300
```

-continued

```
Leu Lys Lys Ile Ser Gln Glu His Pro Thr Ala Cys Leu Arg Ala Gly
305                 310                 315                 320

Ala Leu Met Ala Val Leu Ser Tyr Leu Asp Phe Phe Ser Thr Gly Val
            325                 330                 335

Gln Arg Val Ala Leu Ser Thr Ala Ala Asn Met Cys Lys Lys Leu Pro
        340                 345                 350

Ser Asp Ala Ser Asp Tyr Val Met Glu Ala Val Pro Leu Leu Thr Asn
    355                 360                 365

Leu Leu Gln Tyr His Asp Ser Lys Val Leu Glu Tyr Ala Ser Ile Cys
370                 375                 380

Leu Thr Arg Ile Ala Glu Ala Phe Ala Pro Tyr Pro Glu Lys Leu Asp
385                 390                 395                 400

Glu Leu Cys Asn His Gly Leu Val Thr Gln Ala Ala Ser Leu Ile Ser
            405                 410                 415

Thr Ser Asn Ser Gly Gly Gln Ala Ser Leu Ser Val Ser Thr Tyr
        420                 425                 430

Thr Gly Leu Ile Arg Leu Leu Ser Thr Cys Ala Ser Gly Ser Pro Leu
        435                 440                 445

Gly Phe Arg Thr Leu Leu Leu Gly Ile Ser Ser Ile Leu Lys Asp
450                 455                 460

Ile Leu Leu Gly Ser Gly Val Ser Ala Asn Ala Ser Val Ser Pro Ala
465                 470                 475                 480

Leu Ser Arg Pro Ala Asp Gln Ile Tyr Glu Ile Val Asn Leu Ala Asn
            485                 490                 495

Glu Leu Leu Pro Pro Leu Pro Glu Gly Val Ile Ser Leu Pro Thr Ser
        500                 505                 510

Thr Asn Ala Leu Val Lys Gly Ser Cys Gln Lys Lys Ser Ser Pro Ser
    515                 520                 525

Thr Ser Gly Lys Gln Glu Asp Ile Leu Lys Ile Ser Pro Arg Glu Lys
530                 535                 540

Leu Leu Gly Asp Gln Pro Glu Leu Leu Gln Phe Gly Leu Asp Leu
545                 550                 555                 560

Leu Pro Val Leu Val Gln Ile Tyr Gly Ser Ser Val Asn Gly Thr Ile
            565                 570                 575

Arg His Lys Cys Leu Ser Val Ile Gly Lys Leu Met Tyr Phe Ser Ser
        580                 585                 590

Ser Glu Met Ile Gln Ser Leu Ile Gly Asp Thr Asn Ile Ser Ser Phe
    595                 600                 605

Leu Ala Gly Val Leu Ala Trp Lys Asp Pro Gln Val Leu Val Pro Ala
610                 615                 620

Leu Gln Val Ala Glu Ile Leu Met Glu Lys Leu Pro Glu Thr Phe Ser
625                 630                 635                 640

Lys Val Phe Val Arg Glu Gly Val Val His Ala Val Asp Gln Leu Val
            645                 650                 655

Leu Val Gly Lys Pro Ser His Ala Ser Pro Thr Asp Lys Asp Asn Asp
        660                 665                 670

Cys Val Pro Gly Ser Ala Arg Ser Arg Arg Tyr Arg Arg Ser Ser
    675                 680                 685

Asn Ala Asn Ser Asp Gly Asn Gln Ser Glu Glu Pro Lys Asn Pro Ala
690                 695                 700

Ser Leu Thr Ile Gly Ala Asn His Asn Ser Leu Asp Thr Pro Thr Ala
705                 710                 715                 720

Ser Phe Met Leu Arg Glu Thr Val Ser Ser Cys Ala Lys Ala Phe Lys
```

```
                    725                 730                 735
Asp Lys Tyr Phe Pro Ser Asp Gly Gly Asp Val Asp Val Gly Val Thr
                740                 745                 750

Asp Asp Leu Leu His Leu Lys Asn Leu Cys Thr Lys Leu Thr Ala Gly
            755                 760                 765

Ile Asp Asp His Lys Val Lys Gly Lys Gly Lys Ser Lys Ala Ser Gly
        770                 775                 780

Pro Phe Leu Gly Asp Phe Ser Ala Ser Lys Glu Glu Tyr Leu Ile Gly
785                 790                 795                 800

Val Ile Ser Glu Ile Leu Gly Glu Ile Ser Lys Gly Asp Gly Val Ser
                805                 810                 815

Thr Phe Glu Phe Ile Gly Ser Gly Val Val Ala Ala Leu Leu Asn Tyr
            820                 825                 830

Phe Ser Cys Gly Tyr Phe Ser Lys Glu Lys Ile Ser Glu Leu Asn Leu
        835                 840                 845

Pro Lys Leu Arg Gln Glu Gly Leu Arg Arg Phe Lys Ala Phe Leu Glu
850                 855                 860

Val Ala Leu Pro Phe Asp Gly Asn Glu Gly Lys Val Pro Pro Met Thr
865                 870                 875                 880

Val Leu Ile Gln Lys Leu Gln Asn Ala Leu Ser Ser Leu Glu Arg Phe
                885                 890                 895

Pro Val Val Leu Ser His Pro Ser Arg Ser Leu Ser Gly Ser Ala Arg
            900                 905                 910

Leu Ser Ser Gly Leu Ser Ala Leu Ala His Pro Leu Lys Leu Arg Leu
        915                 920                 925

Cys Arg Ala Ser Gly Glu Lys Thr Leu Arg Asp Tyr Ser Ser Asn Ile
930                 935                 940

Val Leu Ile Asp Pro Leu Ala Ser Leu Ala Ala Val Glu Glu Phe Leu
945                 950                 955                 960

Trp Pro Arg Val Gln Arg Ser Glu Ser Ala Leu Lys Pro Ala Ala Pro
                965                 970                 975

Ile Gly Asn Thr Glu Pro Gly Thr Leu Pro Ser Gly Ala Gly Val Ser
            980                 985                 990

Ser Pro Ser Ser Ser Thr Pro Ala  Ser Thr Thr Arg Arg  His Ser Ser
        995                 1000                 1005

Arg Ser Arg Ser Ala Ile Asn  Ile Gly Asp Thr Ser  Lys Lys Asp
    1010                 1015                 1020

Pro Val His Glu Lys Gly Thr  Ser Ser Ser Lys Gly  Lys Gly Lys
    1025                 1030                 1035

Gly Val Met Lys Pro Ala Gln  Ala Asp Lys Gly Pro  Gln Thr Arg
    1040                 1045                 1050

Ser Asn Ala Gln Lys Arg Ala  Val Leu Asp Lys Asp  Thr Gln Met
    1055                 1060                 1065

Lys Pro Ala Ser Gly Asp Ser  Ser Ser Glu Asp Glu  Glu Leu Glu
    1070                 1075                 1080

Ile Ser Pro Val Asp Ile Asp  Asp Ala Leu Val Ile  Glu Glu Asp
    1085                 1090                 1095

Asp Ile Ser Asp Asp Glu Asp  Asp Asn Glu Asp  Val Leu Asp
    1100                 1105                 1110

Asp Ser Leu Pro Met Cys Thr  Pro Asp Lys Val His  Asp Val Lys
    1115                 1120                 1125

Leu Ala Asp Ser Val Asp Asp  Asp Gly Leu Ala Thr  Ser Gly Arg
    1130                 1135                 1140
```

```
Gln Met Asn Pro Ala Ser Gly Gly Thr Ser Gly Ala Ala Ala Ala
1145                1150                1155

Arg Ala Ser Asp Ser Ile Asp Thr Gly Ile Gly Asn Ser Tyr Gly
1160                1165                1170

Ser Arg Gly Ala Leu Ser Phe Ala Ala Ala Met Ala Gly Leu
1175                1180                1185

Gly Ala Ala Ser Gly Arg Gly Ile Arg Gly Ser Arg Asp Leu His
1190                1195                1200

Gly Arg Thr Leu Asn Arg Ser Ser Asp Glu Pro Ser Lys Leu Ile
1205                1210                1215

Phe Thr Ala Ala Gly Lys Gln Leu Ser Arg His Leu Thr Ile Tyr
1220                1225                1230

Gln Ala Val Gln Arg Gln Leu Met Leu Asp Glu Asp Asp Asp Asp
1235                1240                1245

Arg Phe Gly Gly Ser Asp Leu Val Ser Ser Asp Gly Ser Arg Phe
1250                1255                1260

Asn Asp Ile Tyr Thr Ile Met Tyr Gln Arg Pro Asp Ser Gln Val
1265                1270                1275

Asn Arg Leu Ser Val Gly Gly Ala Ser Ser Thr Thr Pro Ser Lys
1280                1285                1290

Ser Thr Lys Ser Ala Thr Thr Asn Ser Ser Val Glu Ser Gln Ser
1295                1300                1305

His Arg Ala Ser Leu Leu Asp Ser Ile Leu Gln Gly Glu Leu Pro
1310                1315                1320

Cys Asp Leu Glu Lys Ser Asn Ser Thr Tyr Asn Val Leu Ala Leu
1325                1330                1335

Leu Arg Val Leu Glu Gly Leu Asn Gln Leu Cys Pro Arg Leu Arg
1340                1345                1350

Ala Gln Thr Leu Ser Asp Arg Phe Ala Glu Gly Lys Ile Thr Ser
1355                1360                1365

Leu Asp Asp Leu Ser Thr Thr Ala Ala Lys Val Pro Leu Asp Glu
1370                1375                1380

Phe Val Asn Ser Lys Leu Thr Pro Lys Leu Ala Arg Gln Ile Gln
1385                1390                1395

Asp Ala Leu Ala Leu Cys Ser Gly Ser Leu Pro Ser Trp Cys Tyr
1400                1405                1410

Gln Leu Thr Arg Ala Cys Pro Phe Leu Phe Pro Phe Gln Thr Arg
1415                1420                1425

Arg Gln Tyr Phe Tyr Ser Thr Ala Phe Gly Leu Ser Arg Ala Leu
1430                1435                1440

Asn Arg Leu Gln Gln Gln Gln Gly Ala Asp Gly Ser Gly Ser Thr
1445                1450                1455

Asn Glu Arg Glu Met Arg Ile Gly Arg Leu Gln Arg Gln Lys Val
1460                1465                1470

Arg Val Ser Arg Asn Arg Ile Leu Asp Ser Ala Ala Lys Val Met
1475                1480                1485

Glu Met Tyr Ser Ser Gln Lys Ala Val Leu Glu Val Glu Tyr Phe
1490                1495                1500

Gly Glu Val Gly Thr Gly Leu Gly Pro Thr Leu Glu Phe Tyr Thr
1505                1510                1515

Leu Leu Ser His Asp Leu Gln Lys Ala Ser Leu Gly Met Trp Arg
1520                1525                1530
```

Ser Ser Ser Gly Asp Lys Val Ser Met Gln Ile Gly Arg Asp Glu
1535                1540                1545

Ile Glu Asp Gly Lys Pro Ser Ala Ala Asn Arg Asp Ile Val Leu
1550                1555                1560

Ala Pro Leu Gly Leu Phe Pro Arg Pro Trp Pro Ser Thr Ala Asp
1565                1570                1575

Ile Ser Glu Gly Gly Gln Phe His Lys Val Ile Glu Tyr Phe Arg
1580                1585                1590

Leu Leu Gly Arg Val Met Ala Lys Ala Leu Gln Asp Gly Arg Leu
1595                1600                1605

Leu Asp Val Pro Leu Ser Thr Ala Phe Tyr Lys Leu Ile Leu Gly
1610                1615                1620

Gln Glu Leu Asp Leu His Asp Ile Val Leu Phe Asp Ala Glu Leu
1625                1630                1635

Gly Lys Thr Leu Gln Glu Leu Arg Val Val Val Ala Arg Lys His
1640                1645                1650

Tyr Leu Glu Gly Val Gly Gly Asp Asn Ser Ser Thr Ile Ser Asp
1655                1660                1665

Leu Cys Leu Arg Gly Cys Arg Ile Glu Asp Leu Ser Leu Glu Phe
1670                1675                1680

Thr Leu Pro Gly Tyr Pro Glu Tyr Ile Leu Arg Ser Gly Asp Glu
1685                1690                1695

Ile Val Asp Ile Thr Asn Leu Glu Glu Tyr Ile Ser Leu Val Val
1700                1705                1710

Asp Ala Thr Val Lys Arg Gly Val Thr Arg Gln Ile Glu Ala Phe
1715                1720                1725

Arg Ser Gly Phe Asn Gln Val Phe Asp Ile Thr Ser Leu Gln Ile
1730                1735                1740

Phe Thr Pro Ser Glu Leu Asp Tyr Leu Leu Cys Gly Arg Arg Glu
1745                1750                1755

Leu Trp Glu Val Glu Thr Leu Ala Glu His Ile Lys Phe Asp His
1760                1765                1770

Gly Tyr Asn Ala Lys Ser Pro Ala Ile Ile Asn Leu Leu Glu Ile
1775                1780                1785

Met Gly Glu Leu Thr Ala Asp Gln Gln Arg Ala Phe Cys Gln Phe
1790                1795                1800

Val Thr Gly Ala Pro Arg Leu Pro Pro Gly Gly Leu Ala Val Leu
1805                1810                1815

Asn Pro Lys Leu Thr Ile Val Arg Lys His Ser Ser Thr Ser Ser
1820                1825                1830

Ala Ala Ala Asn Gly Ala Gly Ala Ser Glu Thr Ala Asp Asp Asp
1835                1840                1845

Leu Pro Ser Val Met Thr Cys Ala Asn Tyr Leu Lys Leu Pro Pro
1850                1855                1860

Tyr Ser Thr Lys Glu Ile Met Tyr Lys Lys Leu Leu Tyr Ala Ile
1865                1870                1875

Asn Glu Gly Gln Gly Ser Phe Asp Leu Ser
1880                1885

<210> SEQ ID NO 5
<211> LENGTH: 4524
<212> TYPE: DNA
<213> ORGANISM: Brassica rapa

<400> SEQUENCE: 5

-continued

```
atggagaaca gggggcagaa acgaatggag gatgtggagg agctacctgc tgataagaga      60
gcttgtaact cacaggactc taggtcaagc tcatctggtg gctcgtctgt tcagagccag     120
tctcaagaag cagccaatgg agcgagctcg ggacacgaaa ccactgacgc tgatatggac     180
acttcttcat cagattctcc ttctagtcat tcagatggag agccagacaa ggaggaggag     240
gaggaggagg actacggatc ttgcgattct gatgatgatg atgaagaagg tgaagatccg     300
aggcacaagg cgcttcagga tgttcagtgg gggagatcgt ctgaggatca gcagaagttg     360
agttctcttg tgacgagatt gagtgaagaa gtcgatcctt cttttgcagt tgactggtct     420
acggagctgt gtgaggtctt gtctttctgt actgaagatt cgctgtccac cgttatggcc     480
gatacgcttt cccgggtgct tgttaagttg gctaatcatg agagcaatgc agatattatg     540
ctgcttgcta tcagagcggt tacttacttg tctgatgttt atccgcggtc tgtagcattc     600
cttgtgaaac atgagactct ccctgctctt tgccagagac tacaggcaat tgagtacttg     660
gacgttgctg agcagtgttt gcaagcactt gagaaaatat ccaaagatga gccagtggcg     720
tgcttgaatg ctggagcaat taaggcagtg cttccgtata ttgatttctt ctcaactagc     780
ttacagagag tcgcagtttc tactgtggtg aatatatgta ggaagctttc atctgagtct     840
ccctccccct ttatggatgc tgttccaatt ttatgcaatc ttcttcagta tgaagatcga     900
cagttggtgg aaaatgtggc tatttgctta acaaaaatag cagatcaagt tagcgagtca     960
cctgaaatgt tggatcaact atctagccat ggtctgattc atcaatccat acatctttta    1020
aacttgaatg ccgcaccac cctatctcaa cctgtttaca atggtgtgat tggattgcta    1080
agaaaactat cttctggttc aatttttagcc ttcagaacgt tatatgaact taacattggc    1140
tacagactaa aagaaattat atccacgtat gacatttccc attcagtgtc ttctacacat    1200
cccaacaata catgttccaa ccaggtgcat gaagtcctga agttggtgat tgagcttctt    1260
ccatcttcgc ctgtagagga taatcagctg gcattggaaa aggaaagttt tcttgttaat    1320
cagcccgatc tcttgcaaca atttggagca gacatacttc ctgttatgat tcaggtgcta    1380
aaatctggag cgaacgtata tgttttttat ggttgcctat cagcaatcca caagctgact    1440
tgcttgagta agtcagtcga ttttgtcgat ttactgaaga atgcaaacat tttaagtgtt    1500
ttggcgggca ttttgtcaag gaaagttcat catgtggttg ttgtagcact acagattgct    1560
gaagcgcttc ttgggaaata cagtgatgat tttttgaatt cgtttataaa ggagggtgtt    1620
tatttcgcaa ttgaagcgct tttaaactcg ggcaacaga atcaaggatc agctgacggt    1680
tcagaagagc atgttccgaa agagactgtg aaatgcttgt gccagtcttt tgaaagatcg    1740
agttcctctt cttcacaaac ttgtaagatc gagaaggatt ctgtctacat tctcgcaaca    1800
cgtatcaagg agagtttctt tggacctgag gtattcgact ctcagaaagg cttgacagat    1860
gttctccaga acctcaagca cttgtctgca gcacttgacg atttgatgac tgaacctatt    1920
gatgcacatg ccctgcacga tgagaagttc ttctcagtat ggagccaaat catggaaagg    1980
ctgaatggaa gggaatctgt gtccacattt gaatttacag agagtggagt tgtgaaggca    2040
ctgacaaatt acctgtctaa tagactccac caaaggaaat ttagcaaagg cgattcagaa    2100
tgtgatagtt tgccatttgt tggtaacaga tttgaagtgt tcacaagatc actttggtct    2160
gatggcgagg caacttcatc cgtattaata aagaatctcc aaaattcctt atcttcatta    2220
gagaactacc caattgtcct aagccagttt ttgaagcaaa ggaactcatt cgcgactgtt    2280
cccaatggac gtagcataag ctatccaatc ctaagagttc gttttgtcaa agcagagggg    2340
```

```
gagacttgct tgcgtgatta ctcccaagac ttggtcaccg ttgacccact ttgcttcttg    2400
gatgctgtcg atcaatacat gtggcctaaa gtgcagttag aacctttata ttccgttgaa    2460
gaaaaagatc aagctatgga atgtccatct tctcagctgg agtcaacttc tatatcttgt    2520
caaggtgaaa gctcaaccca tatggagatt gacagtccta acgcatctca gttgcaggga    2580
tctcaagagg aagaccaaga gcagcttcca gattcagggg aagataatac ttcctcatct    2640
gaagaggagg atgcgttacc tgaggaggat gcgttaccta acttttgtt tcgtctagaa     2700 gggcttgaac tagaccgctc tttgactgta taccaggcta ttctcttgca caaactaaaa    2760
tcaggaagtg aaactaccaa cgattccaag ctgagtggat cccacaccat cacgtatgaa    2820
agggccccac aacttgcaga gtctgatgaa aatctgtttc ctctcggatt tatggacaat    2880
gacgagtatc acccgttttt atccttcttg tttgctcaaa gacttgattt gcgccacaaa    2940
gcaacaaatc ctcctgcgta cgacatgttg tttctgctca agagtctgga gggcatgaac    3000
agatttctct ttcacctgat ttgtcatgaa cggataaatg ctttggggga aggtaggctg    3060
gagaatttgg atgatctgag ggtgcagctt cgtcctgtgc catatgctga atttgttagt    3120
agtaagctaa cagagaagct ggagcagcag ctgcgtgatt cctttgctgt gtcaacctgc    3180
ggtctaccac cgtggtttaa tgatctaatg ggttcatgcc cttttctgtt tagttttgaa    3240
gtcaaaacca aatacttccg gctagcagca ttcggttcgc agaaagtcca tcatcatcca    3300
caacacctta gcagtgaagg gcgcccagta actggtagtt tacctcgcaa aaagttctta    3360
gcttgccgtg aaaccattct agagtctgct tcaaaaatga tggagttgca cggcaaccag    3420
aaggtggtaa ttgaggttga gtacagtgaa gaagtgggaa ctggtcttgg gccaacgctg    3480
gagttctaca cacttgtcag tagagcgttt caaaatccag accttggcat gtggaggtgt    3540
gatcgtagtt cctttgctgg aaaaccaaag gaagactcag gattttggt ggctccttcg     3600 ggactctttc cacgaccttg gtcagataca tcagctgctt tcccagatgt gctacagaaa    3660
tttgtgctct tagggacagt ggtagcaaag gctctacatg atggacgagt tttggacatt    3720
cctttctcca aagccttcta taaactgatt atcggacagg agttgagttc atttgacatc    3780
cacttcattg accctgaact ttgtaaaaca ctggtggaat tgcaagctct gacacgtagg    3840
aaaaaggttt tctcagaatc acaaactgat gcccgagcag ccaagtgtga tttgagtttc    3900
cgtggaacaa atattgagga tctttgtctt gaatttgtgc tgcctggcta cacagactat    3960
gttctcgctc ttcattctgc taatgatatg gtaaatttgg ataacctcga ggagtatatc    4020
aaggctattg tcaatgcaac aatatgtaac gggatccaaa aacaagtgga agcatttcgg    4080
tctggattta acaaagtttt ccctattgaa catcttggga tattcaatga agaagaactg    4140
gaaactctct tgtgtggaga acgagatctc tttaatatga atgaagtctt ggatcacatc    4200
aagtttgatc atgatatac ttctagcagc ccaccagttg aaaatttgtt ggagattctg      4260
catgagtttg acaaggatca acaacgagcc tttctgcagt ttgtaacagg atgtcctcgt    4320
ctacctcctg ggggcttggc gtctctcaat cccaaactaa caattgtccg caagcgtggt    4380
agcgattctt cagaaactga cttgccgagt gtgatgacat cgctaattac tctaaagctt    4440
ccaccttact cttccaaaga aaagatgaag gagaagctaa tttatgctat aactgaaggc    4500
caaggttcct tccatctctc ttaa                                            4524

<210> SEQ ID NO 6
<211> LENGTH: 1507
<212> TYPE: PRT
<213> ORGANISM: Brassica rapa
```

<400> SEQUENCE: 6

```
Met Glu Asn Arg Gly Gln Lys Arg Met Glu Asp Val Glu Glu Leu Pro
1               5                   10                  15

Ala Asp Lys Arg Ala Cys Asn Ser Gln Asp Ser Arg Ser Ser Ser Ser
            20                  25                  30

Gly Gly Ser Ser Val Gln Ser Gln Ser Gln Glu Ala Ala Asn Gly Ala
        35                  40                  45

Ser Ser Gly His Glu Thr Thr Asp Ala Asp Met Asp Thr Ser Ser Ser
    50                  55                  60

Asp Ser Pro Ser Ser His Ser Asp Gly Glu Pro Asp Lys Glu Glu Glu
65              70                  75                  80

Glu Glu Glu Asp Tyr Gly Ser Cys Asp Ser Asp Asp Asp Glu Glu
                85                  90                  95

Gly Glu Asp Pro Arg His Lys Ala Leu Gln Asp Val Gln Trp Gly Arg
            100                 105                 110

Ser Ser Glu Asp Gln Gln Lys Leu Ser Ser Leu Val Thr Arg Leu Ser
        115                 120                 125

Glu Glu Val Asp Pro Ser Leu Gln Leu Thr Gly Leu Thr Glu Leu Cys
130                 135                 140

Glu Val Leu Ser Phe Cys Thr Glu Asp Ser Leu Ser Thr Val Met Ala
145                 150                 155                 160

Asp Thr Leu Ser Arg Val Leu Val Lys Leu Ala Asn His Glu Ser Asn
                165                 170                 175

Ala Asp Ile Met Leu Leu Ala Ile Arg Ala Val Thr Tyr Leu Ser Asp
            180                 185                 190

Val Tyr Pro Arg Ser Val Ala Phe Leu Val Lys His Glu Thr Leu Pro
        195                 200                 205

Ala Leu Cys Gln Arg Leu Gln Ala Ile Glu Tyr Leu Asp Val Ala Glu
210                 215                 220

Gln Cys Leu Gln Ala Leu Glu Lys Ile Ser Lys Asp Glu Pro Val Ala
225                 230                 235                 240

Cys Leu Asn Ala Gly Ala Ile Lys Ala Val Leu Ser Tyr Ile Asp Phe
                245                 250                 255

Phe Ser Thr Ser Leu Gln Arg Val Ala Val Ser Thr Val Val Asn Ile
            260                 265                 270

Cys Arg Lys Leu Ser Ser Glu Ser Pro Ser Phe Met Asp Ala Val
        275                 280                 285

Pro Ile Leu Cys Asn Leu Leu Gln Tyr Glu Asp Arg Gln Leu Val Glu
        290                 295                 300

Asn Val Ala Ile Cys Leu Thr Lys Ile Ala Asp Gln Val Ser Glu Ser
305                 310                 315                 320

Pro Glu Met Leu Asp Gln Leu Ser Ser His Gly Leu Ile His Gln Ser
                325                 330                 335

Ile His Leu Leu Asn Leu Asn Gly Arg Thr Thr Leu Ser Gln Pro Val
            340                 345                 350

Tyr Asn Gly Val Ile Gly Leu Leu Arg Lys Leu Ser Ser Gly Ser Ile
        355                 360                 365

Leu Ala Phe Arg Thr Leu Tyr Glu Leu Asn Ile Gly Tyr Arg Leu Lys
    370                 375                 380

Glu Ile Ile Ser Thr Tyr Asp Ile Ser His Ser Val Ser Ser Thr His
385                 390                 395                 400

Pro Asn Asn Thr Cys Ser Asn Gln Val His Glu Val Leu Lys Leu Val
```

-continued

```
                405                 410                 415
Ile Glu Leu Leu Pro Ser Ser Pro Val Glu Asp Asn Gln Leu Ala Leu
            420                 425                 430
Glu Lys Glu Ser Phe Leu Val Asn Gln Pro Asp Leu Leu Gln Gln Phe
            435                 440                 445
Gly Ala Asp Ile Leu Pro Val Met Ile Gln Val Leu Lys Ser Gly Ala
450                 455                 460
Asn Val Tyr Val Phe Tyr Gly Cys Leu Ser Ala Ile His Lys Leu Thr
465                 470                 475                 480
Cys Leu Ser Lys Ser Val Asp Phe Val Asp Leu Leu Lys Asn Ala Asn
                485                 490                 495
Ile Leu Ser Val Leu Ala Gly Ile Leu Ser Arg Lys Val His His Val
            500                 505                 510
Val Val Val Ala Leu Gln Ile Ala Glu Ala Leu Leu Gly Lys Tyr Ser
            515                 520                 525
Asp Asp Phe Leu Asn Ser Phe Ile Lys Glu Gly Val Tyr Phe Ala Ile
530                 535                 540
Glu Ala Leu Leu Asn Ser Gly Gln Gln Asn Gln Gly Ser Ala Asp Gly
545                 550                 555                 560
Ser Glu Glu His Val Pro Lys Glu Thr Val Lys Cys Leu Cys Gln Ser
                565                 570                 575
Phe Glu Arg Ser Ser Ser Ser Ser Gln Thr Cys Lys Ile Glu Lys
            580                 585                 590
Asp Ser Val Tyr Ile Leu Ala Thr Arg Ile Lys Glu Ser Phe Phe Gly
            595                 600                 605
Pro Glu Val Phe Asp Ser Gln Lys Gly Leu Thr Asp Val Leu Gln Asn
610                 615                 620
Leu Lys His Leu Ser Ala Ala Leu Asp Asp Leu Met Thr Glu Pro Ile
625                 630                 635                 640
Asp Ala His Ala Leu His Asp Glu Lys Phe Phe Ser Val Trp Ser Gln
                645                 650                 655
Ile Met Glu Arg Leu Asn Gly Arg Glu Ser Val Ser Thr Phe Glu Phe
            660                 665                 670
Thr Glu Ser Gly Val Val Lys Ala Leu Thr Asn Tyr Leu Ser Asn Arg
            675                 680                 685
Leu His Gln Arg Lys Phe Ser Lys Gly Asp Ser Glu Cys Asp Ser Leu
            690                 695                 700
Pro Phe Val Gly Asn Arg Phe Glu Val Phe Thr Arg Ser Leu Trp Ser
705                 710                 715                 720
Asp Gly Glu Ala Thr Ser Ser Val Leu Ile Lys Asn Leu Gln Asn Ser
                725                 730                 735
Leu Ser Ser Leu Glu Asn Tyr Pro Ile Val Leu Ser Gln Phe Leu Lys
            740                 745                 750
Gln Arg Asn Ser Phe Ala Thr Val Pro Asn Gly Arg Ser Ile Ser Tyr
            755                 760                 765
Pro Ile Leu Arg Val Arg Phe Val Lys Ala Glu Gly Glu Thr Cys Leu
            770                 775                 780
Arg Asp Tyr Ser Gln Asp Leu Val Thr Val Asp Pro Leu Cys Phe Leu
785                 790                 795                 800
Asp Ala Val Asp Gln Tyr Met Trp Pro Lys Val Gln Leu Glu Pro Leu
                805                 810                 815
Tyr Ser Val Glu Glu Lys Asp Gln Ala Met Glu Cys Pro Ser Ser Gln
            820                 825                 830
```

```
Leu Glu Ser Thr Ser Ile Ser Cys Gln Gly Glu Ser Ser Thr His Met
        835                 840                 845

Glu Ile Asp Ser Pro Asn Ala Ser Gln Leu Gln Gly Ser Gln Glu Glu
850                 855                 860

Asp Gln Glu Gln Leu Pro Asp Ser Gly Glu Asp Asn Thr Ser Ser Ser
865                 870                 875                 880

Glu Glu Glu Asp Ala Leu Pro Glu Glu Asp Ala Leu Pro Arg Leu Leu
                885                 890                 895

Phe Arg Leu Glu Gly Leu Glu Leu Asp Arg Ser Leu Thr Val Tyr Gln
                900                 905                 910

Ala Ile Leu Leu His Lys Leu Lys Ser Gly Ser Glu Thr Thr Asn Asp
                915                 920                 925

Ser Lys Leu Ser Gly Ser His Thr Ile Thr Tyr Glu Arg Ala Pro Gln
        930                 935                 940

Leu Ala Glu Ser Asp Glu Asn Leu Phe Pro Leu Gly Phe Met Asp Asn
945                 950                 955                 960

Asp Glu Tyr His Pro Phe Leu Ser Phe Leu Ala Gln Arg Leu Asp
                965                 970                 975

Leu Arg His Lys Ala Thr Asn Pro Pro Ala Tyr Asp Met Leu Phe Leu
                980                 985                 990

Leu Lys Ser Leu Glu Gly Met Asn  Arg Phe Leu Phe His  Leu Ile Cys
                995                 1000                1005

His Glu  Arg Ile Asn Ala Phe  Gly Glu Gly Arg Leu  Glu Asn Leu
        1010                1015                1020

Asp Asp  Leu Arg Val Gln Leu  Arg Pro Val Pro Tyr  Ala Glu Phe
        1025                1030                1035

Val Ser  Ser Lys Leu Thr Glu  Lys Leu Glu Gln Gln  Leu Arg Asp
        1040                1045                1050

Ser Phe  Ala Val Ser Thr Cys  Gly Leu Pro Pro Trp  Phe Asn Asp
        1055                1060                1065

Leu Met  Gly Ser Cys Pro Phe  Leu Phe Ser Phe Glu  Val Lys Thr
        1070                1075                1080

Lys Tyr  Phe Arg Leu Ala Ala  Phe Gly Ser Gln Lys  Val His His
        1085                1090                1095

His Pro  Gln His Leu Ser Ser  Glu Gly Arg Pro Val  Thr Gly Ser
        1100                1105                1110

Leu Pro  Arg Lys Lys Phe Leu  Ala Cys Arg Glu Thr  Ile Leu Glu
        1115                1120                1125

Ser Ala  Ser Lys Met Met Glu  Leu His Gly Asn Gln  Lys Val Val
        1130                1135                1140

Ile Glu  Val Glu Tyr Ser Glu  Val Gly Thr Gly  Leu Gly Pro
        1145                1150                1155

Thr Leu  Glu Phe Tyr Thr Leu  Val Ser Arg Ala Phe  Gln Asn Pro
        1160                1165                1170

Asp Leu  Gly Met Trp Arg Cys  Asp Arg Ser Ser Phe  Ala Gly Lys
        1175                1180                1185

Pro Lys  Glu Asp Ser Gly Phe  Leu Val Ala Pro Ser  Gly Leu Phe
        1190                1195                1200

Pro Arg  Pro Trp Ser Asp Thr  Ser Ala Ala Phe Pro  Asp Val Leu
        1205                1210                1215

Gln Lys  Phe Val Leu Leu Gly  Thr Val Val Ala Lys  Ala Leu His
        1220                1225                1230
```

```
Asp Gly Arg Val Leu Asp Ile Pro Phe Ser Lys Ala Phe Tyr Lys
    1235                1240                1245

Leu Ile Ile Gly Gln Glu Leu Ser Ser Phe Asp Ile His Phe Ile
    1250                1255                1260

Asp Pro Glu Leu Cys Lys Thr Leu Val Glu Leu Gln Ala Leu Thr
    1265                1270                1275

Arg Arg Lys Lys Val Phe Ser Glu Ser Gln Thr Asp Ala Arg Ala
    1280                1285                1290

Ala Lys Cys Asp Leu Ser Phe Arg Gly Thr Asn Ile Glu Asp Leu
    1295                1300                1305

Cys Leu Glu Phe Val Leu Pro Gly Tyr Thr Asp Tyr Val Leu Ala
    1310                1315                1320

Leu His Ser Ala Asn Asp Met Val Asn Leu Asp Asn Leu Glu Glu
    1325                1330                1335

Tyr Ile Lys Ala Ile Val Asn Ala Thr Ile Cys Asn Gly Ile Gln
    1340                1345                1350

Lys Gln Val Glu Ala Phe Arg Ser Gly Phe Asn Lys Val Phe Pro
    1355                1360                1365

Ile Glu His Leu Gly Ile Phe Asn Glu Glu Leu Glu Thr Leu
    1370                1375                1380

Leu Cys Gly Glu Arg Asp Leu Phe Asn Met Asn Glu Val Leu Asp
    1385                1390                1395

His Ile Lys Phe Asp His Gly Tyr Thr Ser Ser Ser Pro Pro Val
    1400                1405                1410

Glu Asn Leu Leu Glu Ile Leu His Glu Phe Asp Lys Asp Gln Gln
    1415                1420                1425

Arg Ala Phe Leu Gln Phe Val Thr Gly Cys Pro Arg Leu Pro Pro
    1430                1435                1440

Gly Gly Leu Ala Ser Leu Asn Pro Lys Leu Thr Ile Val Arg Lys
    1445                1450                1455

Arg Gly Ser Asp Ser Ser Glu Thr Asp Leu Pro Ser Val Met Thr
    1460                1465                1470

Cys Ala Asn Tyr Leu Lys Leu Pro Pro Tyr Ser Ser Lys Glu Lys
    1475                1480                1485

Met Lys Glu Lys Leu Ile Tyr Ala Ile Thr Glu Gly Gln Gly Ser
    1490                1495                1500

Phe His Leu Ser
    1505

<210> SEQ ID NO 7
<211> LENGTH: 4446
<212> TYPE: DNA
<213> ORGANISM: Brassica rapa

<400> SEQUENCE: 7
atggagaaca gaggacagaa acgaatggag gttgtggggg agccacctgc tgataagaga      60
gcttgcaact cacaagactt cacatctggc gcctcctctg ctcaggctca acaagccaat     120
ggtaacactg atgctgacat ggacacttct tcctctgcct ctccttcgag tcgttcagat     180
ggagaacaag acagggagga ggaggaggag gaggaatccg actacggatc atgcgattcc     240
gatgatgagg atccgaggag gagggtgctt cagcggtatc agaggggag atcaacagga      300 gatcagctga aactgaagtc tctcgcgtcg aggttgagtg aagaaaacga tccttctctg     360
cagttgactg gtcttacgga gctctgtgaa gtgttgtctt tctgtactga ggactctctg     420
```

```
tccattgtga tggctgactt gctctcgcgt gtgcttgtta agttggctaa gcatgagagc   480
aatgcagata tcatgctgct cgcaatcaga gcggttactt acttgtctga tgtttatccg   540
cggtcggtag cgttccttgt taaacatgag accattcctg ctctctgcca aagactactg   600
acgattgagt acttggatgt tgctgagcag tgtttgcaag cacttgagaa gatatccaga   660
gatcagccgg tagcatgctt gaacgctgga gcaattatgg cagtgctttc gtatatcgat   720
ttcttttcaa caagcataca gagagtcgca gtttctactg tggtgaatat atgtaggaag   780
cttccacctg agcctccctc gcctgtcatg gatgctgttc cagtattatg caatcttctt   840
caatatgaag accgacagtt ggtggagagt gtcgctattt gcttgacaaa aatagcagat   900
caagttagcc agtcgcctgc tatgttggat caactatgta gccatggact tatccatcaa   960
tcaacacatc ttttaaactt gaacagccgc acaaccctat ctcaacctgt ttacaacggc  1020
gtgattggat tgctaagaaa actatcttct ggttcaactt tagcttttcag aacattgtat  1080
gagcttaaca ttggctacag actaaaagaa atcatatcca cctatgacat ttctcattca  1140
gtttcttcta cacagcccat ccatccatgc tccaaccagg tgcatgaagt cttgaagttg  1200
gtgattgagc ttcttccagc ttcacctgtt ggggataatc agctggcatt agaaaaggaa  1260
agttttcttg tcgatcagcc taatctcttg caacaatttg gagcagacat gcttcctgtt  1320
atgactcagg tgctaaagtc tggagctagc gtttatgttt cttatggttg cctatcagca  1380
attcacaagc tgacttgctt aagtaagtca gacgatcttg tcgagttact gaacaatgct  1440
aacatttcaa gtgttttggc gggcattttt tcaaggaaag atcatcatgt ggtcgttgtt  1500
gcactacaga ttgctgaagt gcttcttgag aaatacagag atgctttttt gaattccttt  1560
ataaaagagg gtgttttttt cgcaatcgca gcactcctaa cttctgatag gggacaacag  1620
atcaatccag tatccggttt cattcaagga tctgttccga aagagattgt gaaatgcttg  1680
tgccagtctt ttgaaggatc agtttcctct tcttcacaaa cttgcaaggt tggaaatgat  1740
tctgtctaca tcctcgcaac acgtatcaag gagagtttct ttggacctga ggtattcgac  1800
tctcagaaag gcttgacgga tgtcctccag aacctcaaga atctgtcggc agaactcaac  1860
gatttggtga ctgtacctgt cgatgcgcat gtcctgcatg tgagaggtt cttctcaata  1920
tggaatcaaa tcatggcaag gctgaaagag agggaatctg tgtccacttt tgaatttact  1980
gagagtggag ttgtgaaggc tctggcaaat tatctgtcta atggactcta cgaaaggaaa  2040
cttaacaaag gcgatcctga atgtgatagt ttaccacttg ttggtaacag atttgaagtg  2100
ttcacaagac tactttggtc tgatggcgag gcaactccgt ccgctttaat acagaagctc  2160
caaaattcct tatcttcttt agaaaactac ccaattgtcc tgagccagtt tttgaagcaa  2220
aggaactgtt tcgctgctat tccaaatgga cgttgcataa gttatccagt cctaagagtt  2280
cgttttgcta aagcagaggg ggagacttgt ctgcgtgatt actctccaaa ctttgtcacc  2340
gttgacccac tttgctactt ggcgctgtt agtcagtgcc tgtggcccca agtgaatttg   2400
gaacctttaa attctgtcga agcgaaagat caggctatag aatgtcaatc ttcacagctg  2460
cagtcaactt cgatatcttg tcaaggtgaa agctcaagcc atatggaaat tgactgtcct  2520
aatgcatctc agctgcaggg atctcaagag gaggaagacc aatatcacct tatagattca  2580
ggagaagaga attcttcctc atctaaagaa gaggatgtgc gacctcgact tttgtttcgt  2640
ctggaagggc ttgagctaga cccctctttg actgtttacc aggcaattct ctcgcacaaa  2700
ctaaaatcag aaaatgagac taccaacgat tcaaagctta gtggacacca caccatcact  2760
tacgaaagag ctccacagct tgcagtgtct catgaaaatc tgtttcccct cagatctatg  2820
```

```
gacaacgacg agcatcaccc gtttttatcc tacttgtttg ctcatagact tggtttgcgc    2880
cacaaaggga caagtcctcc tgagtatgcc atattgtttc tgctcaagag tctggagggc    2940
atgaacagat ttctctttca gctgatttgt catgaaagga ttaatgcttt tggggaaggt    3000
aggctggaga gtttggatga tctaactgtg caggtgcgtc cggtgccata tgctgaattt    3060
gttagctcta agcttacaga gaagttagag cagcagctgc gtgattcttt tgctgtgtca    3120
ccgtgcggtc taccaccgtg gtttaatgat ctaatggctt catgcccgtt tctgtttagt    3180
tttgaagtca aatctaaata cttccgactt gcagcgttcg gtccacagca agtccataat    3240
cagccacagc accttggtag ttcaaatgtt catggtagtt tacctcgtaa aaagtttta    3300 gcttgccgtg aaaagattct agagtctgct gcgaaaatga tggagttaca cggcacccag    3360
aaggtggccg ttgaggttgc gtacagtgaa gaagtcggaa ctggccttgg gccaacgctg    3420
gagttctaca cacttgtcag tagagcattt caaaatccgg atcttggtat gtggaggagt    3480
gatcctagct ccttggctgg aaagccaatg gtacctcctt caggactctt ccacgccct    3540 tggtcggcta catcagctgc ttttccaggt gtgctgcaga gtttgttct cttggggaca    3600 gtggtagcca aggctctaca agatggacga gtcttggaca ttcctttctc taaaaccttc    3660
tataaactaa ttctcggaca ggagttgagt tcatttgaca tccatttcgt tgaccctgaa    3720
ctttgtaaaa cactggtgga attgcaagct ctggcacgta ggagaaaggt tatctcagaa    3780
tcacaaagtg atgtccgagc agctaagtgt gacttgagtt ccgtggaac aaagattgag    3840 gacctttgtc ttgattttc cctgcctggc tacacggact atgttctctc tcctcggttt    3900
gctaatgata tggtaaattt gggtaacctc gaggagtatg taaaggctat tgtcaatgcc    3960
acagtatgta atgggatcaa aaaacaagtg gaagcgtttc ggtctggatt taacaaagtt    4020
ttccctattg aacatcttaa gatatttaat gaagaagaac tggaaacttt gttgtgtgga    4080
gaacgagatc tctttaatat gaatgaagtc ttggaccaca tcaagtttga tcatggttat    4140
acttctagca gcccaccagt tcaaaatttg ttggagattc tgcatgagtt tcacaaggag    4200
caacagcgag cttttctgca atttgtaaca ggatgtcctc ggctacccc tggcggtttg    4260 gcgtctctca gtcccaaact taccattgtc cgcaagcacg gtagtgattc atcagaaaca    4320
gacctgccta gtgtgatgac ctgcgccaat tatctgaaac ttccaccta ctcttccaaa    4380 gaaaagatga aggagaagct gatctatgcc ataactgaag gcaaggttc cttccatctc    4440 tcttaa                                                              4446
```

<210> SEQ ID NO 8
<211> LENGTH: 1481
<212> TYPE: PRT
<213> ORGANISM: Brassica rapa
<400> SEQUENCE: 8

```
Met Glu Asn Arg Gly Gln Lys Arg Met Glu Val Val Gly Glu Pro Pro
1               5                   10                  15

Ala Asp Lys Arg Ala Cys Asn Ser Gln Asp Phe Thr Ser Gly Ala Ser
            20                  25                  30

Ser Ala Gln Ala Gln Gln Ala Asn Gly Asn Thr Asp Ala Asp Met Asp
        35                  40                  45

Thr Ser Ser Ser Ala Ser Pro Ser Ser Arg Ser Asp Gly Glu Gln Asp
    50                  55                  60

Arg Glu Glu Glu Glu Glu Glu Ser Asp Tyr Gly Ser Cys Asp Ser
65                  70                  75                  80
```

```
Asp Asp Glu Asp Pro Arg Arg Val Leu Gln Arg Tyr Gln Arg Gly
            85                  90                  95

Arg Ser Thr Gly Asp Gln Leu Lys Leu Lys Ser Leu Ala Ser Arg Leu
            100                 105                 110

Ser Glu Glu Asn Asp Pro Ser Leu Gln Leu Thr Gly Leu Thr Glu Leu
            115                 120                 125

Cys Glu Val Leu Ser Phe Cys Thr Glu Asp Ser Leu Ser Ile Val Met
130                 135                 140

Ala Asp Leu Leu Ser Arg Val Leu Val Lys Leu Ala Lys His Glu Ser
145                 150                 155                 160

Asn Ala Asp Ile Met Leu Leu Ala Ile Arg Ala Val Thr Tyr Leu Ser
                165                 170                 175

Asp Val Tyr Pro Arg Ser Val Ala Phe Leu Val Lys His Glu Thr Ile
            180                 185                 190

Pro Ala Leu Cys Gln Arg Leu Leu Thr Ile Glu Tyr Leu Asp Val Ala
            195                 200                 205

Glu Gln Cys Leu Gln Ala Leu Glu Lys Ile Ser Arg Asp Gln Pro Val
            210                 215                 220

Ala Cys Leu Asn Ala Gly Ala Ile Met Ala Val Leu Ser Tyr Ile Asp
225                 230                 235                 240

Phe Phe Ser Thr Ser Ile Gln Arg Val Ala Val Ser Thr Val Val Asn
                245                 250                 255

Ile Cys Arg Lys Leu Pro Pro Glu Pro Pro Ser Pro Val Met Asp Ala
                260                 265                 270

Val Pro Val Leu Cys Asn Leu Leu Gln Tyr Glu Asp Arg Gln Leu Val
            275                 280                 285

Glu Ser Val Ala Ile Cys Leu Thr Lys Ile Ala Asp Gln Val Ser Gln
            290                 295                 300

Ser Pro Ala Met Leu Asp Gln Leu Cys Ser His Gly Leu Ile His Gln
305                 310                 315                 320

Ser Thr His Leu Leu Asn Leu Asn Ser Arg Thr Thr Leu Ser Gln Pro
                325                 330                 335

Val Tyr Asn Gly Val Ile Gly Leu Leu Arg Lys Leu Ser Ser Gly Ser
            340                 345                 350

Thr Leu Ala Phe Arg Thr Leu Tyr Glu Leu Asn Ile Gly Tyr Arg Leu
            355                 360                 365

Lys Glu Ile Ile Ser Thr Tyr Asp Ile Ser His Ser Val Ser Ser Thr
            370                 375                 380

Gln Pro Ile His Pro Cys Ser Asn Gln Val His Glu Val Leu Lys Leu
385                 390                 395                 400

Val Ile Glu Leu Leu Pro Ala Ser Pro Val Gly Asp Asn Gln Leu Ala
                405                 410                 415

Leu Glu Lys Glu Ser Phe Leu Val Asp Gln Pro Asn Leu Leu Gln Gln
            420                 425                 430

Phe Gly Ala Asp Met Leu Pro Val Met Thr Gln Val Leu Lys Ser Gly
            435                 440                 445

Ala Ser Val Tyr Val Ser Tyr Gly Cys Leu Ser Ala Ile His Lys Leu
450                 455                 460

Thr Cys Leu Ser Lys Ser Asp Asp Leu Val Glu Leu Leu Asn Asn Ala
465                 470                 475                 480

Asn Ile Ser Ser Val Leu Ala Gly Ile Phe Ser Arg Lys Asp His His
                485                 490                 495
```

```
Val Val Val Val Ala Leu Gln Ile Ala Glu Val Leu Leu Glu Lys Tyr
            500                 505                 510

Arg Asp Ala Phe Leu Asn Ser Phe Ile Lys Glu Gly Val Phe Phe Ala
        515                 520                 525

Ile Ala Ala Leu Leu Thr Ser Asp Arg Gly Gln Gln Ile Asn Pro Val
        530                 535                 540

Ser Gly Phe Ile Gln Gly Ser Val Pro Lys Glu Ile Val Lys Cys Leu
545                 550                 555                 560

Cys Gln Ser Phe Glu Gly Ser Val Ser Ser Ser Gln Thr Cys Lys
                565                 570                 575

Val Gly Asn Asp Ser Val Tyr Ile Leu Ala Thr Arg Ile Lys Glu Ser
        580                 585                 590

Phe Phe Gly Pro Glu Val Phe Asp Ser Gln Lys Gly Leu Thr Asp Val
        595                 600                 605

Leu Gln Asn Leu Lys Asn Leu Ser Ala Glu Leu Asn Asp Leu Val Thr
        610                 615                 620

Val Pro Val Asp Ala His Val Leu His Gly Glu Arg Phe Phe Ser Ile
625                 630                 635                 640

Trp Asn Gln Ile Met Ala Arg Leu Lys Glu Arg Glu Ser Val Ser Thr
                645                 650                 655

Phe Glu Phe Thr Glu Ser Gly Val Val Lys Ala Leu Ala Asn Tyr Leu
                660                 665                 670

Ser Asn Gly Leu Tyr Glu Arg Lys Leu Asn Lys Gly Asp Pro Glu Cys
        675                 680                 685

Asp Ser Leu Pro Leu Val Gly Asn Arg Phe Glu Val Phe Thr Arg Leu
        690                 695                 700

Leu Trp Ser Asp Gly Glu Ala Thr Pro Ser Ala Leu Ile Gln Lys Leu
705                 710                 715                 720

Gln Asn Ser Leu Ser Ser Leu Glu Asn Tyr Pro Ile Val Leu Ser Gln
                725                 730                 735

Phe Leu Lys Gln Arg Asn Cys Phe Ala Ala Ile Pro Asn Gly Arg Cys
                740                 745                 750

Ile Ser Tyr Pro Val Leu Arg Val Arg Phe Ala Lys Ala Glu Gly Glu
        755                 760                 765

Thr Cys Leu Arg Asp Tyr Ser Pro Asn Phe Val Thr Val Asp Pro Leu
770                 775                 780

Cys Tyr Leu Asp Ala Val Ser Gln Cys Leu Trp Pro Gln Val Asn Leu
785                 790                 795                 800

Glu Pro Leu Asn Ser Val Glu Ala Lys Asp Gln Ala Ile Glu Cys Gln
                805                 810                 815

Ser Ser Gln Leu Gln Ser Thr Ser Ile Ser Cys Gln Gly Glu Ser Ser
                820                 825                 830

Ser His Met Glu Ile Asp Cys Pro Asn Ala Ser Gln Leu Gln Gly Ser
        835                 840                 845

Gln Glu Glu Glu Asp Gln Tyr His Leu Ile Asp Ser Gly Glu Glu Asn
        850                 855                 860

Ser Ser Ser Ser Lys Glu Glu Asp Val Arg Pro Arg Leu Leu Phe Arg
865                 870                 875                 880

Leu Glu Gly Leu Glu Leu Asp Pro Ser Leu Thr Val Tyr Gln Ala Ile
                885                 890                 895

Leu Ser His Lys Leu Lys Ser Glu Asn Glu Thr Thr Asn Asp Ser Lys
                900                 905                 910

Leu Ser Gly His His Thr Ile Thr Tyr Glu Arg Ala Pro Gln Leu Ala
```

```
                915                 920                 925
Val Ser His Glu Asn Leu Phe Pro Leu Arg Ser Met Asp Asn Asp Glu
    930                 935                 940

His His Pro Phe Leu Ser Tyr Leu Phe Ala His Arg Leu Gly Leu Arg
945                 950                 955                 960

His Lys Gly Thr Ser Pro Pro Glu Tyr Ala Ile Leu Phe Leu Leu Lys
                965                 970                 975

Ser Leu Glu Gly Met Asn Arg Phe Leu Phe Gln Leu Ile Cys His Glu
            980                 985                 990

Arg Ile Asn Ala Phe Gly Glu Gly Arg Leu Glu Ser Leu Asp Asp Leu
        995                 1000                1005

Thr Val Gln Val Arg Pro Val Pro Tyr Ala Glu Phe Val Ser Ser
    1010                1015                1020

Lys Leu Thr Glu Lys Leu Glu Gln Gln Leu Arg Asp Ser Phe Ala
    1025                1030                1035

Val Ser Pro Cys Gly Leu Pro Pro Trp Phe Asn Asp Leu Met Ala
    1040                1045                1050

Ser Cys Pro Phe Leu Phe Ser Phe Glu Val Lys Ser Lys Tyr Phe
    1055                1060                1065

Arg Leu Ala Ala Phe Gly Pro Gln Val His Asn Gln Pro Gln
    1070                1075                1080

His Leu Gly Ser Ser Asn Val His Gly Ser Leu Pro Arg Lys Lys
    1085                1090                1095

Phe Leu Ala Cys Arg Glu Lys Ile Leu Glu Ser Ala Ala Lys Met
    1100                1105                1110

Met Glu Leu His Gly Thr Gln Lys Val Ala Val Glu Val Ala Tyr
    1115                1120                1125

Ser Glu Glu Val Gly Thr Gly Leu Gly Pro Thr Leu Glu Phe Tyr
    1130                1135                1140

Thr Leu Val Ser Arg Ala Phe Gln Asn Pro Asp Leu Gly Met Trp
    1145                1150                1155

Arg Ser Asp Pro Ser Ser Leu Ala Gly Lys Pro Met Val Pro Pro
    1160                1165                1170

Ser Gly Leu Phe Pro Arg Pro Trp Ser Ala Thr Ser Ala Ala Phe
    1175                1180                1185

Pro Gly Val Leu Gln Lys Phe Val Leu Leu Gly Thr Val Val Ala
    1190                1195                1200

Lys Ala Leu Gln Asp Gly Arg Val Leu Asp Ile Pro Phe Ser Lys
    1205                1210                1215

Thr Phe Tyr Lys Leu Ile Leu Gly Gln Glu Leu Ser Ser Phe Asp
    1220                1225                1230

Ile His Phe Val Asp Pro Glu Leu Cys Lys Thr Leu Val Glu Leu
    1235                1240                1245

Gln Ala Leu Ala Arg Arg Lys Val Ile Ser Glu Ser Gln Ser
    1250                1255                1260

Asp Val Arg Ala Ala Lys Cys Asp Leu Ser Phe Arg Gly Thr Lys
    1265                1270                1275

Ile Glu Asp Leu Cys Leu Asp Phe Ser Leu Pro Gly Tyr Thr Asp
    1280                1285                1290

Tyr Val Leu Ser Pro Arg Phe Ala Asn Asp Met Val Asn Leu Gly
    1295                1300                1305

Asn Leu Glu Glu Tyr Val Lys Ala Ile Val Asn Ala Thr Val Cys
    1310                1315                1320
```

Asn Gly Ile Lys Lys Gln Val Glu Ala Phe Arg Ser Gly Phe Asn
1325                1330                1335

Lys Val Phe Pro Ile Glu His Leu Lys Ile Phe Asn Glu Glu Glu
1340                1345                1350

Leu Glu Thr Leu Leu Cys Gly Glu Arg Asp Leu Phe Asn Met Asn
1355                1360                1365

Glu Val Leu Asp His Ile Lys Phe Asp His Gly Tyr Thr Ser Ser
1370                1375                1380

Ser Pro Pro Val Gln Asn Leu Leu Glu Ile Leu His Glu Phe His
1385                1390                1395

Lys Glu Gln Gln Arg Ala Phe Leu Gln Phe Val Thr Gly Cys Pro
1400                1405                1410

Arg Leu Pro Pro Gly Gly Leu Ala Ser Leu Ser Pro Lys Leu Thr
1415                1420                1425

Ile Val Arg Lys His Gly Ser Asp Ser Ser Glu Thr Asp Leu Pro
1430                1435                1440

Ser Val Met Thr Cys Ala Asn Tyr Leu Lys Leu Pro Pro Tyr Ser
1445                1450                1455

Ser Lys Glu Lys Met Lys Glu Lys Leu Ile Tyr Ala Ile Thr Glu
1460                1465                1470

Gly Gln Gly Ser Phe His Leu Ser
1475                1480

<210> SEQ ID NO 9
<211> LENGTH: 5553
<212> TYPE: DNA
<213> ORGANISM: Solanum lycopersicum

<400> SEQUENCE: 9

```
atggaaactc ggagccggaa acgaacggag gccacgtcat cagcgccttc tgcttcttct      60
ccttcatcag gtcccaccac acgcgctgtt aagaaagctc gttttaccac acgcgccgcc     120
tcaaactcga tctcaactcg ttcccgactc acaaatcgtt cccaagacct acaatcgatg     180
gactccacga atgaatcatc cgggtctggc agccgaacca gcggggaaaa gaatcacggg     240
ttagatagaa ataatccgga agggtaag agaaagagc acgaaattag ggatagagac         300
agagatatgg gattgaacat ggatactgat ggggtgatg aagatgataa tgaaagtgaa       360
ggtggtgctg ggattttgca acataatttg acttcagcaa gtagtgcact tcaaggactg     420
ttgagaaaat tgggtgctgg tttggatgat ttactgccga gttcagcaat ggtgtccgct     480
tcctcgtcgc aacagaatgg gcgtctgaag aagatattat cgggcttgag agctgacggg     540
gaagaaggga gcaaatagaa ggcattgacg cagctttgtg tgatgctttc cattgggaca     600
gaagactctt tgagcacttt ttcagtggac tcttttgtac ctgtcctggt ggggctgctt     660
aatcatatga gtaatcctga tattatgctt ctcgcagcta gggcgttaac ccatttggtt     720
gatgttctgc catcttcttg tgctgctgtt gtgcattatg gagcggtttc atgttttgta     780
gctcgcttac tcacaattga atacatggac ttagctgagc agtctctaca agctttaaag     840
aagatatctc aagaagatcc aactgcttgt ttgcaagcag gtgcactcat ggctgtgctg     900
tcgtatctcg atttcttttc cactggtgtt cagagagtag cactagcaac tgctgctaat     960
atgtgcaaga gctgccttc ggatgctgct gactttgtga tggaagctgt tccattgttg     1020
acgaatctcc ttcagtatca tgatgcaaag gtattagagc atgcttctat ctgcttgacc    1080
cggatagctg aagcatttgc atcatctcca gaaaagctag atgaactctg taatcacgga    1140
```

```
cttgtcacac aggctgcctc cctcatctca accagtaatt ctggaggtgg tcaggcttca    1200
ctcagcacgg aaacttacac aggcttgatc cggcttcttt gtacttgtgc cagtggctca    1260
ccattagggg ctaaaacctt gatgatgctt ggtatcagtg ggatcctcaa ggacatttta    1320
tcagcctctg tctctatttc acctgccatg agcagacctg cggagcagat ttttgagatt    1380
gtgaatcttg caaatgaact acttcctccg ctgcctcaag gaattatctc tcttcctgtt    1440
agcacaaatt tgttcattag aggtcctttt acgcggaaat cctctgctag tggttctagc    1500
aaacaggagg atcttaatgc atcttctcag gaggtatcag ctcatgagaa actattgaat    1560
gatcaacctg aacttctgca acaatttgga atggatctcc ttcctgttct gatacagaca    1620
tatggatcca gtgtaaatac agcagcacgc cacaaatgcc tctcagttat tggaaaactt    1680
atgtatttca gtaatgcaga tatgattcaa tctttaacta atgacactaa cttgtcaagt    1740
ttcttggctg gggttttggc gtggaaggat ccccaagtat tggtccccgc tcttcaaata    1800
gcagagattc taatggagaa gctccctgga ttttttggca agatgtttgt ccgggaaggt    1860
gttgttcatg ctgtagatgc cttgatgttg tctgggtctc atgtttctgc tcctccccat    1920
ccaacacgtg ctgagaaaga gaaacataat agacgccgta gcactaattc caatacagat    1980
gcaatttctg ttgaagatct tacaagtcca gttccaagta ctggatctct gccaaattca    2040
atggaaattc ggaccgttaa ttctagcctc cggatgtcag tcagtacatg tgcaaaagct    2100
ttcaaggata atacttccc atcagattct gaggctgctg aagctggtgt cacggatgat    2160
cttatacgat tgaagaatct ctgcatgaag ttgaatgctg gtattgatga gcagatagct    2220
aaacctaaag gaaaatccaa acatttggt cctcagcttg gggatagcta tgttggaaaa    2280
gaagaaaact tggctgaagt gatagctgcc atgatggggg aactcagcaa agggggatggt    2340 gtttcaactt ttgagttcag tggaagtgga gttgttgctt ctttgctgaa atattttacg    2400
tttgcgtact tttctaagga aagaatctct gatactagta tgtctaagct tcgacaacaa    2460
gcaatcagaa gatacaagtc ttttattgca gttgcccttc ctgctggtgt tgatggtgga    2520
aatatggttc ccatgactgt tctggtccaa aagcttcaaa atgctctatg ttcattggag    2580
cgttttcctg ttgtattgag tcatagttcc agatcatcga caggaaatgc acgtctttct    2640
tcaggtttaa gtgttttgtc tcagcctttt aagctgcgcc tttgcagagc tcaaggagag    2700
aaaaccctcc gtgactactc ttcaaatgtt ttgctgattg atccttttggc aagttttagta    2760 gctattgaag aattcctttg ggcccgagtt gggagacctg aggctgaaca gaaggcatct    2820
gctactggtg gaaactctgg gtctgggact ataccctgctg gaggcagtgc gtcatctcca    2880
tctatgtcca ctcctgcctc tgcatctcgt cgtcattctg ctcgatcaag gtcagcagtt    2940
aatattaatg aaagtgatgg aagctcttca aagggcaaag gtaaagcggt tttgaagcct    3000
gctcaaaaag atcgcagggg aattcgatca agagatcctg ttaaaataag agctgccttg    3060
gagaaggcct taagagagga gcctgttgat ggggagacta gttcagagga tgacgagctg    3120
catccttctc tcattgaact tgatgatgct ttggtgattg aggatgatat gttcgatgaa    3180
gatgaagatg accatgatga tgtgctgagg gatgatcctt ttcctgtctg catggcagat    3240
gaagtgcatg atgttaaatt gggagactct tcggaggata gcccttttgc acagacacca    3300
actggcagca atacaaatgc tggtggtggt tctgggagca gaattgcttc tgctcgggga    3360
tctgattccg ttgagttcag aagtaggaac tcgtatggtt caagggggc aatgtcattt    3420 gctgctgctg ccatggctgg tctttcatct gctagtgtta gaggtgtgag gggcgctaga    3480
```

```
gatcgacatg ggcatcctct actcagctct ggtgatccac caaaactaat attttctgtt     3540
ggtgggaagc cgcttaatag gcagttgact atctaccagg ctatccagcg gcagcttgtt     3600
ctagacgagg atgatgatga gagatatggt ggcaatgatt ttgtatctgg tgacggcagt     3660
agggtttgga gtgatattta cacgatcaca taccagaggg cagacaacca agctgagagg     3720
tcaagtgggt ctgggagttc aatttccaag tctatgaaaa ccagttcttc aacaagttcc     3780
ggtgctgatc cttcattggt tcaagcatca ttgttagata gtatattgca gggagaactt     3840
ccttgtgatc tggagaaaag taaccctact tacagtattt tgtacctctt acgtgtattg     3900
gaggcgctga atcagcttgc cccccgtttg agagtcctgt ccatgattga tgatttctct     3960
gaaggaaaaa tttctagtct agatgagctc ggtactacgg gtatcaaaat cccttctgag     4020
gaatttgtca atagtaagct cactccgaaa ttggcacgac agatccagga tgctcttgca     4080
cttttgtagtg gatctcttcc atcttggtgt taccagttga ccaaggcctg cccatttctt     4140
tttccatttg agactcggcg ccagtacttc tattcaactg cttttgggtt gtcacgtgct     4200
ttatataggc tgcagcaaca gcaaggtgct gatggtaatg ggtctactca tgagagagca     4260
gttagggttg gcagattaca gcgccagaaa gttcgtgtct caaggaaccg cattctggat     4320
tctgctgcaa aagtaatgga gatgtactct agccaaaaag ctgttcttga agttgaatat     4380
tttggtgaag ttggtactgg cctgggtcct acacttgagt tttataccct tataagtcac     4440
gatctacaga aacttggact tggaatgtgg agatctggtt tatcattaac ttcaaatgaa     4500
cattctgtgg aagttcatat cgataataaa ttaagtagaa gtgacggaga tcttgtccaa     4560
gcacctcttg gattattccc acgtccctgg tcaccacata ctggtactgt tgatggaggt     4620
caattctata aagcaattga atatttccgc ttgcttggac gtgttatggc gaaagctctt     4680
caagatggac ggcttttgga ccttccactg tccatggcct tctataagct cgttcttggt     4740
caagaacttg atttgtatga tattctttct tttgacaccg aattggggaa gactttgcaa     4800
gagttgcaag ccctcgtcag tcgaaagcaa tatatagaat caataaaaga tcagaacctg     4860
gacgagtctt atgacatgca ttttcgtggg actccagttg aggatctttg tttagatttc     4920
acacttcctg gctatcctga atatattctt aaagcaggcg acgagaatgt gagtcgcgat     4980
atcgtggatt ttaacttgga ggagtatatt tctttggtag ttgatgctac tgtgaaaact     5040
ggaatcaggc agcaaatgga ggcttttaga tctggcttca atcaggtttt cgactttca     5100
gctctgcaaa tattctctcc ttcagagtta gactatctat tatgtggccg tagagagctg     5160
tggaagcctg agacgctagt agatcacata aaattcgatc atggattcac atccaagagt     5220
cctcctatta ttcatttact agagattatg ggagagttca cacctgagca gcaacgagca     5280
ttctgccagt ttgttactgg tgctcctcgg ctccccgcag gtggtcttgc ttctctgaat     5340
cctaagttga caattgtgag gaagcattca tctagtgctg gcaatgcagc acagaacagt     5400
aatgccccat cagaatctgc agatgaagac ctacccagtg tgatgacatg tgctaattac     5460
ttgaaactcc ctccctattc tactaaggag atcatgtcca agaaattact ctatgccatt     5520
aatgaaggtc aaggatcgtt tgatttgtca taa                                  5553
```

<210> SEQ ID NO 10
<211> LENGTH: 1850
<212> TYPE: PRT
<213> ORGANISM: Solanum lycopersicum

<400> SEQUENCE: 10

Met Glu Thr Arg Ser Arg Lys Arg Thr Glu Ala Thr Ser Ser Ala Pro

-continued

```
1               5                   10                  15
Ser Ala Ser Ser Pro Ser Ser Gly Pro Thr Thr Arg Ala Val Lys Lys
                20                  25                  30

Ala Arg Phe Thr Thr Arg Ala Ala Ser Asn Ser Ile Ser Thr Arg Ser
                35                  40                  45

Arg Leu Thr Asn Arg Ser Gln Asp Leu Gln Ser Met Asp Ser Thr Asn
            50                  55                  60

Glu Ser Ser Gly Ser Gly Ser Arg Thr Arg Arg Gly Lys Asn His Gly
65                      70                  75                  80

Leu Asp Arg Asn Asn Pro Glu Lys Gly Lys Glu Lys Glu His Glu Ile
                    85                  90                  95

Arg Asp Arg Asp Arg Asp Met Gly Leu Asn Met Asp Thr Asp Gly Gly
                100                 105                 110

Asp Glu Asp Asp Asn Glu Ser Glu Gly Gly Ala Gly Ile Leu Gln His
                115                 120                 125

Asn Leu Thr Ser Ala Ser Ser Ala Leu Gln Gly Leu Leu Arg Lys Leu
            130                 135                 140

Gly Ala Gly Leu Asp Asp Leu Leu Pro Ser Ser Ala Met Val Ser Ala
145                     150                 155                 160

Ser Ser Ser Gln Gln Asn Gly Arg Leu Lys Lys Ile Leu Ser Gly Leu
                    165                 170                 175

Arg Ala Asp Gly Glu Glu Gly Lys Gln Ile Glu Ala Leu Thr Gln Leu
                180                 185                 190

Cys Val Met Leu Ser Ile Gly Thr Glu Asp Ser Leu Ser Thr Phe Ser
                195                 200                 205

Val Asp Ser Phe Val Pro Val Leu Val Gly Leu Leu Asn His Met Ser
            210                 215                 220

Asn Pro Asp Ile Met Leu Leu Ala Ala Arg Ala Leu Thr His Leu Val
225                     230                 235                 240

Asp Val Leu Pro Ser Ser Cys Ala Ala Val Val His Tyr Gly Ala Val
                    245                 250                 255

Ser Cys Phe Val Ala Arg Leu Leu Thr Ile Glu Tyr Met Asp Leu Ala
                260                 265                 270

Glu Gln Ser Leu Gln Ala Leu Lys Lys Ile Ser Gln Glu Asp Pro Thr
            275                 280                 285

Ala Cys Leu Gln Ala Gly Ala Leu Met Ala Val Leu Ser Tyr Leu Asp
            290                 295                 300

Phe Phe Ser Thr Gly Val Gln Arg Val Ala Leu Ala Thr Ala Ala Asn
305                 310                 315                 320

Met Cys Lys Lys Leu Pro Ser Asp Ala Ala Asp Phe Val Met Glu Ala
                    325                 330                 335

Val Pro Leu Leu Thr Asn Leu Leu Gln Tyr His Asp Ala Lys Val Leu
                340                 345                 350

Glu His Ala Ser Ile Cys Leu Thr Arg Ile Ala Glu Ala Phe Ala Ser
                355                 360                 365

Ser Pro Glu Lys Leu Asp Glu Leu Cys Asn His Gly Leu Val Thr Gln
            370                 375                 380

Ala Ala Ser Leu Ile Ser Thr Ser Asn Ser Gly Gly Gln Ala Ser
385                 390                 395                 400

Leu Ser Thr Glu Thr Tyr Thr Gly Leu Ile Arg Leu Leu Cys Thr Cys
                405                 410                 415

Ala Ser Gly Ser Pro Leu Gly Ala Lys Thr Leu Met Met Leu Gly Ile
                420                 425                 430
```

```
Ser Gly Ile Leu Lys Asp Ile Leu Ser Ala Ser Val Ser Ile Ser Pro
        435                 440                 445
Ala Met Ser Arg Pro Ala Glu Gln Ile Phe Glu Ile Val Asn Leu Ala
    450                 455                 460
Asn Glu Leu Leu Pro Pro Leu Pro Gln Gly Ile Ile Ser Leu Pro Val
465                 470                 475                 480
Ser Thr Asn Leu Phe Ile Arg Gly Pro Phe Thr Arg Lys Ser Ser Ala
                485                 490                 495
Ser Gly Ser Ser Lys Gln Glu Asp Leu Asn Ala Ser Ser Gln Glu Val
            500                 505                 510
Ser Ala His Glu Lys Leu Leu Asn Asp Gln Pro Glu Leu Leu Gln Gln
            515                 520                 525
Phe Gly Met Asp Leu Leu Pro Val Leu Ile Gln Thr Tyr Gly Ser Ser
        530                 535                 540
Val Asn Thr Ala Ala Arg His Lys Cys Leu Ser Val Ile Gly Lys Leu
545                 550                 555                 560
Met Tyr Phe Ser Asn Ala Asp Met Ile Gln Ser Leu Thr Asn Asp Thr
                565                 570                 575
Asn Leu Ser Ser Phe Leu Ala Gly Val Leu Ala Trp Lys Asp Pro Gln
            580                 585                 590
Val Leu Val Pro Ala Leu Gln Ile Ala Glu Ile Leu Met Glu Lys Leu
            595                 600                 605
Pro Gly Val Phe Gly Lys Met Phe Val Arg Glu Gly Val Val His Ala
        610                 615                 620
Val Asp Ala Leu Met Leu Ser Gly Ser His Val Ser Ala Pro Pro His
625                 630                 635                 640
Pro Thr Arg Ala Glu Lys Glu Lys His Asn Arg Arg Ser Thr Asn
                645                 650                 655
Ser Asn Thr Asp Ala Ile Ser Val Glu Asp Leu Thr Ser Pro Val Pro
                660                 665                 670
Ser Thr Gly Ser Leu Pro Asn Ser Met Glu Ile Arg Thr Val Asn Ser
        675                 680                 685
Ser Leu Arg Met Ser Val Ser Thr Cys Ala Lys Ala Phe Lys Asp Lys
        690                 695                 700
Tyr Phe Pro Ser Asp Ser Glu Ala Ala Glu Ala Gly Val Thr Asp Asp
705                 710                 715                 720
Leu Ile Arg Leu Lys Asn Leu Cys Met Lys Leu Asn Ala Gly Ile Asp
                725                 730                 735
Glu Gln Ile Ala Lys Pro Lys Gly Lys Ser Lys Thr Phe Gly Pro Gln
            740                 745                 750
Leu Gly Asp Ser Tyr Val Gly Lys Glu Glu Asn Leu Ala Glu Val Ile
            755                 760                 765
Ala Ala Met Met Gly Glu Leu Ser Lys Gly Asp Gly Val Ser Thr Phe
        770                 775                 780
Glu Phe Ser Gly Ser Gly Val Val Ala Ser Leu Leu Lys Tyr Phe Thr
785                 790                 795                 800
Phe Ala Tyr Phe Ser Lys Glu Arg Ile Ser Asp Thr Ser Met Ser Lys
                805                 810                 815
Leu Arg Gln Gln Ala Ile Arg Arg Tyr Lys Ser Phe Ile Ala Val Ala
            820                 825                 830
Leu Pro Ala Gly Val Asp Gly Gly Asn Met Val Pro Met Thr Val Leu
        835                 840                 845
```

Val Gln Lys Leu Gln Asn Ala Leu Cys Ser Leu Glu Arg Phe Pro Val
850                 855                 860

Val Leu Ser His Ser Ser Arg Ser Ser Thr Gly Asn Ala Arg Leu Ser
865                 870                 875                 880

Ser Gly Leu Ser Val Leu Ser Gln Pro Phe Lys Leu Arg Leu Cys Arg
            885                 890                 895

Ala Gln Gly Glu Lys Thr Leu Arg Asp Tyr Ser Ser Asn Val Leu Leu
            900                 905                 910

Ile Asp Pro Leu Ala Ser Leu Val Ala Ile Glu Glu Phe Leu Trp Ala
            915                 920                 925

Arg Val Gly Arg Pro Glu Ala Glu Gln Lys Ala Ser Ala Thr Gly Gly
            930                 935                 940

Asn Ser Gly Ser Gly Thr Ile Pro Ala Gly Gly Ser Ala Ser Ser Pro
945                 950                 955                 960

Ser Met Ser Thr Pro Ala Ser Ala Ser Arg Arg His Ser Ala Arg Ser
                965                 970                 975

Arg Ser Ala Val Asn Ile Asn Glu Ser Asp Gly Ser Ser Lys Gly
            980                 985                 990

Lys Gly Lys Ala Val Leu Lys Pro Ala Gln Lys Asp Arg Arg Gly Ile
            995                 1000                1005

Arg Ser Arg Asp Pro Val Lys Ile Arg Ala Ala Leu Glu Lys Ala
    1010                1015                1020

Leu Arg Glu Glu Pro Val Asp Gly Glu Thr Ser Ser Glu Asp Asp
    1025                1030                1035

Glu Leu His Pro Ser Leu Ile Glu Leu Asp Asp Ala Leu Val Ile
    1040                1045                1050

Glu Asp Asp Met Phe Asp Glu Asp Glu Asp His Asp Asp Val
    1055                1060                1065

Leu Arg Asp Asp Pro Phe Pro Val Cys Met Ala Asp Glu Val His
    1070                1075                1080

Asp Val Lys Leu Gly Asp Ser Ser Glu Asp Ser Pro Phe Ala Gln
    1085                1090                1095

Thr Pro Thr Gly Ser Asn Thr Asn Ala Gly Gly Gly Ser Gly Ser
    1100                1105                1110

Arg Ile Ala Ser Ala Arg Gly Ser Asp Ser Val Glu Phe Arg Ser
    1115                1120                1125

Arg Asn Ser Tyr Gly Ser Arg Gly Ala Met Ser Phe Ala Ala Ala
    1130                1135                1140

Ala Met Ala Gly Leu Ser Ser Ala Ser Val Arg Gly Val Arg Gly
    1145                1150                1155

Ala Arg Asp Arg His Gly His Pro Leu Leu Ser Gly Asp Pro
    1160                1165                1170

Pro Lys Leu Ile Phe Ser Val Gly Gly Lys Pro Leu Asn Arg Gln
    1175                1180                1185

Leu Thr Ile Tyr Gln Ala Ile Gln Arg Gln Leu Val Leu Asp Glu
    1190                1195                1200

Asp Asp Asp Glu Arg Tyr Gly Gly Asn Asp Phe Val Ser Gly Asp
    1205                1210                1215

Gly Ser Arg Val Trp Ser Asp Ile Tyr Thr Ile Thr Tyr Gln Arg
    1220                1225                1230

Ala Asp Asn Gln Ala Glu Arg Ser Ser Gly Ser Gly Ser Ser Ile
    1235                1240                1245

Ser Lys Ser Met Lys Thr Ser Ser Ser Thr Ser Ser Gly Ala Asp

-continued

|    |    |    |    |    |    |    |    |    |    |
|----|----|----|----|----|----|----|----|----|----|
|    |    | 1250 |  |   | 1255 |  |   | 1260 |   |

Pro Ser Leu Val Gln Ala Ser Leu Leu Asp Ser Ile Leu Gln Gly
1265                 1270                 1275

Glu Leu Pro Cys Asp Leu Glu Lys Ser Asn Pro Thr Tyr Ser Ile
1280                 1285                 1290

Leu Tyr Leu Leu Arg Val Leu Glu Ala Leu Asn Gln Leu Ala Pro
1295                 1300                 1305

Arg Leu Arg Val Leu Ser Met Ile Asp Asp Phe Ser Glu Gly Lys
1310                 1315                 1320

Ile Ser Ser Leu Asp Glu Leu Gly Thr Thr Gly Ile Lys Ile Pro
1325                 1330                 1335

Ser Glu Glu Phe Val Asn Ser Lys Leu Thr Pro Lys Leu Ala Arg
1340                 1345                 1350

Gln Ile Gln Asp Ala Leu Ala Leu Cys Ser Gly Ser Leu Pro Ser
1355                 1360                 1365

Trp Cys Tyr Gln Leu Thr Lys Ala Cys Pro Phe Leu Phe Pro Phe
1370                 1375                 1380

Glu Thr Arg Arg Gln Tyr Phe Tyr Ser Thr Ala Phe Gly Leu Ser
1385                 1390                 1395

Arg Ala Leu Tyr Arg Leu Gln Gln Gln Gly Ala Asp Gly Asn
1400                 1405                 1410

Gly Ser Thr His Glu Arg Ala Val Arg Val Gly Arg Leu Gln Arg
1415                 1420                 1425

Gln Lys Val Arg Val Ser Arg Asn Arg Ile Leu Asp Ser Ala Ala
1430                 1435                 1440

Lys Val Met Glu Met Tyr Ser Ser Gln Lys Ala Val Leu Glu Val
1445                 1450                 1455

Glu Tyr Phe Gly Glu Val Gly Thr Gly Leu Gly Pro Thr Leu Glu
1460                 1465                 1470

Phe Tyr Thr Leu Ile Ser His Asp Leu Gln Lys Leu Gly Leu Gly
1475                 1480                 1485

Met Trp Arg Ser Gly Leu Ser Leu Thr Ser Asn Glu His Ser Val
1490                 1495                 1500

Glu Val His Ile Asp Asn Lys Leu Ser Arg Ser Asp Gly Asp Leu
1505                 1510                 1515

Val Gln Ala Pro Leu Gly Leu Phe Pro Arg Pro Trp Ser Pro His
1520                 1525                 1530

Thr Gly Thr Val Asp Gly Gly Gln Phe Tyr Lys Ala Ile Glu Tyr
1535                 1540                 1545

Phe Arg Leu Leu Gly Arg Val Met Ala Lys Ala Leu Gln Asp Gly
1550                 1555                 1560

Arg Leu Leu Asp Leu Pro Leu Ser Met Ala Phe Tyr Lys Leu Val
1565                 1570                 1575

Leu Gly Gln Glu Leu Asp Leu Tyr Asp Ile Leu Ser Phe Asp Thr
1580                 1585                 1590

Glu Leu Gly Lys Thr Leu Gln Glu Leu Gln Ala Leu Val Ser Arg
1595                 1600                 1605

Lys Gln Tyr Ile Glu Ser Ile Lys Asp Gln Asn Leu Asp Glu Ser
1610                 1615                 1620

Tyr Asp Met His Phe Arg Gly Thr Pro Val Glu Asp Leu Cys Leu
1625                 1630                 1635

Asp Phe Thr Leu Pro Gly Tyr Pro Glu Tyr Ile Leu Lys Ala Gly
1640                 1645                 1650

| | | | | | | | | | | |
|---|---|---|---|---|---|---|---|---|---|---|
| Asp | Glu | Asn | Val | Ser | Arg | Asp | Ile | Val | Asp | Phe | Asn | Leu | Glu | Glu |
| | 1655 | | | | 1660 | | | | 1665 | |

Tyr Ile Ser Leu Val Val Asp Ala Thr Val Lys Thr Gly Ile Arg
    1670            1675            1680

Gln Gln Met Glu Ala Phe Arg Ser Gly Phe Asn Gln Val Phe Asp
    1685            1690            1695

Phe Ser Ala Leu Gln Ile Phe Ser Pro Ser Glu Leu Asp Tyr Leu
    1700            1705            1710

Leu Cys Gly Arg Arg Glu Leu Trp Lys Pro Glu Thr Leu Val Asp
    1715            1720            1725

His Ile Lys Phe Asp His Gly Phe Thr Ser Lys Ser Pro Pro Ile
    1730            1735            1740

Ile His Leu Leu Glu Ile Met Gly Glu Phe Thr Pro Glu Gln Gln
    1745            1750            1755

Arg Ala Phe Cys Gln Phe Val Thr Gly Ala Pro Arg Leu Pro Ala
    1760            1765            1770

Gly Gly Leu Ala Ser Leu Asn Pro Lys Leu Thr Ile Val Arg Lys
    1775            1780            1785

His Ser Ser Ala Gly Asn Ala Ala Gln Asn Ser Asn Ala Pro
    1790            1795            1800

Ser Glu Ser Ala Asp Glu Asp Leu Pro Ser Val Met Thr Cys Ala
    1805            1810            1815

Asn Tyr Leu Lys Leu Pro Pro Tyr Ser Thr Lys Glu Ile Met Ser
    1820            1825            1830

Lys Lys Leu Leu Tyr Ala Ile Asn Glu Gly Gln Gly Ser Phe Asp
    1835            1840            1845

Leu Ser
    1850

<210> SEQ ID NO 11
<211> LENGTH: 3612
<212> TYPE: DNA
<213> ORGANISM: Oryza sativa

<400> SEQUENCE: 11

```
atggagtgcc ccaaggagtg cctcagccac ggcgtgccag ccgccgtgct gcagttcttc      60
gacttcttct cgatgcacaa gcagaagctg gtgctcaaga tcgtcgccaa cgtcttgggc     120
gacttcagcg cgaaggatgc ggccaaggcc atggaggccg cgcccgttct gtgcaacctc     180
ctgcaatcca ctgacaagac gatactcgac tccgccgttt cttgcttggt tttggtctct     240
gatggtgctt gcgacagtgc ccaacacatg gaaaagcttt acgagcttaa tgcagtccaa     300
gcgacgatga ggttgatgga gaacgacggg tggaagagcc tcagcgatga gactttatct     360
ggcatccttg tcttctcaa agacctagct tctctctcag caagggctgt aaagtctctt     420
tttgagttaa acatttgtga tttgctcaag cagatgataa catactacac ctcgtcgcac     480
agtgatcaca ataaggtgca gacgcttgta gagctcattt attatcttat gccacctctt     540
gaaatgtgtg accatcgtac cgaactaatc attgcaaaga gaatgtcat cacagaacaa     600
agtggataca tccaacagct tgctagcatc cttacttta taatacaggt tgcgaaatct     660
gctgcactat catcaatttg ctacagttgt gttgttgtca tcagaaacat tgttgaatta     720
agcacacctt cttccttggt ggaggtacag aagacagtaa acctgtcaag cttacttgct     780
ggctggttgg cccggaagaa ccgccatatc atattccaaa cgctcaacgt ttcgaagacc     840
```

```
cttctgagaa aagaccagaa attcttcttt gagaccttca tcagggaggg tctaaagcat    900
gcaattgatg caatactaac acaggaaaaa ggaaagagcc gcttgccaga aagttgcctt    960
tgttttgatt tagacttgga gacctcgaca gatgatgcat gcaggattaa taatggtgct   1020
atcctgaaac tagcggagga gataaagaaa aacttcttgg taaaggttgc caagtctcct   1080
cacaagtttg ggtgtgcttt taaaagcata aaggaatttt tttctcgttt gaattgtcat   1140
gccacggcac ccccagctaa agatcaggat ctctgcaagc agttgtctga ttttcaagg    1200
caattattat cggatgaact gccaagtact tctactttg agtttgtgca gagtggatct   1260
atcaaacatt tggcaggtta tctttccaat gggacatact ttaattcaaa tctcaggaat   1320
tgccaggact tgataggga gcttaaggag gtgaaaatcc ggctgcagaa gttcacgcac   1380
ttggctctca gcgtggacaa tgaaagctcg gtgaagccac ttgagatttt ggtggagaaa   1440
ctgatagatg cgttgcatgt gtggtatgac agtttccctg taatcctggc tgatgaacag   1500
tgcacacgtg agagcaccat gattcctctg agggattcag gaactgagga accaatgtca   1560
ctatatataa aattttcgag atcagccagg gaggaggagt tggaggatta tggtggagtt   1620
ctccctgttg atctttcttc gacacctgaa tccattgaag aggtcctgtt gcctgagatc   1680
tgtaaaagaa ctggcaatga aacttcatac aaggaaaaca ctcaagaagc aaatgggagc   1740
agaaaatctg ttgggctcag aaatggtgac gggcacaagt tctcaagatt gaaattctct   1800
tacaaaggaa cacaactcca gtcatctaca ccacttttg agtcaatcct ccgctcaatg   1860
catgaaggag aaaccgatct ccagattgac ccatcttttt gggataaaga acacaagata   1920
gtatacagaa gaagaaacaa aagcaagaaa atatcttccc atagttccta caatattcag   1980
ttgtgccgtg tgcatgaaaa acttgaaatg tcattgctta aggaccccctt tttctccacc   2040
atactcactg gcaagcttcc tggtgatctg gatgaatctg atccatcata taacttcctg   2100
ttcatgctga aagtcctcga agggctcaac cgttttcat atcatctatc aatggatgat   2160
aagttatgca aatttgctga aggctgcctc caagagtttg atgaccttaa ggtggcaatt   2220
tgtccaattc cacgggatca gttcgtgagc agtctactga caaataagtt agagcagcaa   2280
atgcaagata gcttgtttgg ggatggcttg ataccctcgt ggtgtatcta tttggttgaa   2340
acttgcccgt tcttgttgtc attcgaagct cgatggaagt atttctgcct gacggcacat   2400
cactcattca tgacagatga ggctagcagt tcaacagaaa ctaagaagta cagcgtaaca   2460
cggagcaaaa tccttgaaga tgcttcatcg atgttgaaca acatggatc agacaccaaa   2520
ttcattgagg tggaatttga tggagaggtt gggaccggtc gaggcccaac cttcgaattc   2580
tataccacag ttagtcatga actacagaga gtgggtcttg gaatgtggag aggagacgac   2640
accagccaag aatgcgaagc tggttttgtc catgccccct ttggtctctt tccacagcca   2700
tggtcctcag caaacacttc atctcaaggg atcagtttgt ccaatgtggt acaaaaattc   2760
aagcttcttg ggcatcttgt agcaagagca gttttggatg gaagggttct ggatattcct   2820
ctctcgaaag cattttacaa gatcatgctt gagcaggacc ttgatattta tgacattcca   2880
tcatttgatc ccaagttggg caagactgtt atggagtttc aagcacttgt taaaggaag   2940
aagttccttgg aggaaaggc atccaatcca gcagctgatt tgtcctataa aaacgtgcga   3000
ttggaggatt tatgtcttga cttacccctt cctggaaatc cggaatatga acttgtccct   3060
ggaggttcag agaagatggt gacacttgac aatttggagg agtatgtgtc ttcaattgtt   3120
gatgcaacct tgaaaagtgg gatatccaat caaatagaag ctttcaaggc tggaattaac   3180
aaggttttttg ctcttaagac tcttcggttg ttcagtgagg atgagatgga gcgtatacta   3240
```

```
tgtggcgaac aagattcttg ggcttcgaac aaacttgagg atcacatcaa ttttgattat   3300
ggatatgatg cgaacagtgc atcagtaatt agtttcctgg atcttgcg  ggagtttgga   3360 agagaggacc agcgggcgtt cttgcatttt acgactggag ctcctcagct cccacttggt   3420
ggcctagctt cgctcgatcc taagctcacc gtagtgcgaa agcaatgtga tggcaaagta   3480
gacaacgaat taccgagtgt caatacttgc cggcatttct tcaagcttcc accgtactcc   3540
tctaaggaga ttatgagaca gaagctcaaa tatgctatca aggagggttt aggctccttc   3600
caattatcat ga                                                      3612

<210> SEQ ID NO 12
<211> LENGTH: 1203
<212> TYPE: PRT
<213> ORGANISM: Oryza sativa

<400> SEQUENCE: 12

Met Glu Cys Pro Lys Glu Cys Leu Ser His Gly Val Pro Ala Ala Val
1               5                   10                  15

Leu Gln Phe Phe Asp Phe Phe Ser Met His Lys Gln Lys Leu Val Leu
            20                  25                  30

Lys Ile Val Ala Asn Val Leu Gly Asp Phe Ser Ala Lys Asp Ala Ala
        35                  40                  45

Lys Ala Met Glu Ala Ala Pro Val Leu Cys Asn Leu Leu Gln Ser Thr
    50                  55                  60

Asp Lys Thr Ile Leu Asp Ser Ala Val Ser Cys Leu Val Leu Val Ser
65                  70                  75                  80

Asp Gly Ala Cys Asp Ser Ala Gln His Met Glu Lys Leu Tyr Glu Leu
                85                  90                  95

Asn Ala Val Gln Ala Thr Met Arg Leu Met Glu Asn Asp Gly Trp Lys
            100                 105                 110

Ser Leu Ser Asp Glu Thr Leu Ser Gly Ile Leu Gly Leu Leu Lys Asp
        115                 120                 125

Leu Ala Ser Leu Ser Ala Arg Ala Val Lys Ser Leu Phe Glu Leu Asn
    130                 135                 140

Ile Cys Asp Leu Leu Lys Gln Met Ile Thr Tyr Tyr Thr Ser Ser His
145                 150                 155                 160

Ser Asp His Asn Lys Val Gln Thr Leu Val Glu Leu Ile Tyr Tyr Leu
                165                 170                 175

Met Pro Pro Leu Glu Met Cys Asp His Arg Thr Glu Leu Ile Ile Ala
            180                 185                 190

Lys Lys Asn Val Ile Thr Glu Gln Ser Gly Tyr Ile Gln Gln Leu Ala
        195                 200                 205

Ser Ile Leu Thr Phe Ile Ile Gln Val Ala Lys Ser Ala Ala Leu Ser
    210                 215                 220

Ser Ile Cys Tyr Ser Cys Val Val Val Ile Arg Asn Ile Val Glu Leu
225                 230                 235                 240

Ser Thr Pro Ser Ser Leu Val Glu Val Gln Lys Thr Val Asn Leu Ser
                245                 250                 255

Ser Leu Leu Ala Gly Trp Leu Ala Arg Lys Asn Arg His Ile Ile Phe
            260                 265                 270

Gln Thr Leu Asn Val Ser Lys Thr Leu Leu Arg Lys Asp Gln Lys Phe
        275                 280                 285

Phe Phe Glu Thr Phe Ile Arg Glu Gly Leu Lys His Ala Ile Asp Ala
    290                 295                 300
```

| Ile | Leu | Thr | Gln | Glu | Lys | Gly | Lys | Ser | Arg | Leu | Pro | Glu | Ser | Cys | Leu |
| 305 | | | | 310 | | | | 315 | | | | | | | 320 |

| Cys | Phe | Asp | Leu | Asp | Leu | Glu | Thr | Ser | Thr | Asp | Asp | Ala | Cys | Arg | Ile |
| | | | 325 | | | | | 330 | | | | | 335 | | |

| Asn | Asn | Gly | Ala | Ile | Leu | Lys | Leu | Ala | Glu | Glu | Ile | Lys | Lys | Asn | Phe |
| | | | 340 | | | | | 345 | | | | 350 | | | |

| Leu | Val | Lys | Val | Ala | Lys | Ser | Pro | His | Lys | Phe | Gly | Cys | Ala | Phe | Lys |
| | | 355 | | | | | 360 | | | | | 365 | | | |

| Ser | Ile | Lys | Glu | Phe | Phe | Ser | Arg | Leu | Asn | Cys | His | Ala | Thr | Ala | Pro |
| | 370 | | | | | 375 | | | | | 380 | | | | |

| Pro | Ala | Lys | Asp | Gln | Asp | Leu | Cys | Lys | Gln | Leu | Ser | Asp | Phe | Ser | Arg |
| 385 | | | | 390 | | | | 395 | | | | | | | 400 |

| Gln | Leu | Leu | Ser | Asp | Glu | Leu | Pro | Ser | Thr | Ser | Thr | Phe | Glu | Phe | Val |
| | | | | 405 | | | | | 410 | | | | | 415 | |

| Gln | Ser | Gly | Ser | Ile | Lys | His | Leu | Ala | Gly | Tyr | Leu | Ser | Asn | Gly | Thr |
| | | | | 420 | | | | | 425 | | | | 430 | | |

| Tyr | Phe | Asn | Ser | Asn | Leu | Arg | Asn | Cys | Gln | Asp | Leu | Ile | Gly | Glu | Leu |
| | | | 435 | | | | | 440 | | | | 445 | | | |

| Lys | Glu | Val | Lys | Ile | Arg | Leu | Gln | Lys | Phe | Thr | His | Leu | Ala | Leu | Ser |
| | 450 | | | | | 455 | | | | | 460 | | | | |

| Val | Asp | Asn | Glu | Ser | Ser | Val | Lys | Pro | Leu | Glu | Ile | Leu | Val | Glu | Lys |
| 465 | | | | | 470 | | | | | 475 | | | | | 480 |

| Leu | Ile | Asp | Ala | Leu | His | Val | Trp | Tyr | Asp | Ser | Phe | Pro | Val | Ile | Leu |
| | | | | 485 | | | | | 490 | | | | | 495 | |

| Ala | Asp | Glu | Gln | Cys | Thr | Arg | Glu | Ser | Thr | Met | Ile | Pro | Leu | Arg | Asp |
| | | | 500 | | | | | 505 | | | | 510 | | | |

| Ser | Gly | Thr | Glu | Glu | Pro | Met | Ser | Leu | Tyr | Ile | Lys | Phe | Ser | Arg | Ser |
| | | | 515 | | | | | 520 | | | | | 525 | | |

| Ala | Arg | Glu | Glu | Glu | Leu | Glu | Asp | Tyr | Gly | Gly | Val | Leu | Pro | Val | Asp |
| | 530 | | | | | 535 | | | | | 540 | | | | |

| Leu | Ser | Ser | Thr | Pro | Glu | Ser | Ile | Glu | Glu | Val | Leu | Leu | Pro | Glu | Ile |
| 545 | | | | | 550 | | | | | 555 | | | | | 560 |

| Cys | Lys | Arg | Thr | Gly | Asn | Glu | Thr | Ser | Tyr | Lys | Glu | Asn | Thr | Gln | Glu |
| | | | | 565 | | | | | 570 | | | | | 575 | |

| Ala | Asn | Gly | Ser | Arg | Lys | Ser | Val | Gly | Leu | Arg | Asn | Gly | Asp | Gly | His |
| | | | 580 | | | | | 585 | | | | 590 | | | |

| Lys | Phe | Ser | Arg | Leu | Lys | Phe | Ser | Tyr | Lys | Gly | Thr | Gln | Leu | Gln | Ser |
| | | | 595 | | | | | 600 | | | | 605 | | | |

| Ser | Thr | Pro | Leu | Phe | Glu | Ser | Ile | Leu | Arg | Ser | Met | His | Glu | Gly | Glu |
| | 610 | | | | | 615 | | | | | 620 | | | | |

| Thr | Asp | Leu | Gln | Ile | Asp | Pro | Ser | Phe | Trp | Asp | Lys | Glu | His | Lys | Ile |
| 625 | | | | 630 | | | | | 635 | | | | | 640 | |

| Val | Tyr | Arg | Arg | Arg | Asn | Lys | Ser | Lys | Lys | Ile | Ser | Ser | His | Ser | Ser |
| | | | | 645 | | | | | 650 | | | | 655 | | |

| Tyr | Asn | Ile | Gln | Leu | Cys | Arg | Val | His | Glu | Lys | Leu | Glu | Met | Ser | Leu |
| | | | 660 | | | | | 665 | | | | 670 | | | |

| Leu | Lys | Asp | Pro | Phe | Phe | Ser | Thr | Ile | Leu | Thr | Gly | Lys | Leu | Pro | Gly |
| | | 675 | | | | | 680 | | | | | 685 | | | |

| Asp | Leu | Asp | Glu | Ser | Asp | Pro | Ser | Tyr | Asn | Phe | Leu | Phe | Met | Leu | Lys |
| | 690 | | | | 695 | | | | 700 | | | | | | |

| Val | Leu | Glu | Gly | Leu | Asn | Arg | Phe | Ser | Tyr | His | Leu | Ser | Met | Asp | Asp |
| 705 | | | | | 710 | | | | | 715 | | | | | 720 |

```
Lys Leu Cys Lys Phe Ala Glu Gly Cys Leu Gln Glu Phe Asp Asp Leu
            725                 730                 735

Lys Val Ala Ile Cys Pro Ile Pro Arg Asp Gln Phe Val Ser Ser Leu
        740                 745                 750

Leu Thr Asn Lys Leu Glu Gln Gln Met Gln Asp Ser Leu Phe Gly Asp
        755                 760                 765

Gly Leu Ile Pro Ser Trp Cys Ile Tyr Leu Val Glu Thr Cys Pro Phe
        770                 775                 780

Leu Leu Ser Phe Glu Ala Arg Trp Lys Tyr Phe Cys Leu Thr Ala His
785                 790                 795                 800

His Ser Phe Met Thr Asp Glu Ala Ser Ser Thr Glu Thr Lys Lys
                805                 810                 815

Tyr Ser Val Thr Arg Ser Lys Ile Leu Glu Asp Ala Ser Ser Met Leu
            820                 825                 830

Asn Lys His Gly Ser Asp Thr Lys Phe Ile Glu Val Glu Phe Asp Gly
            835                 840                 845

Glu Val Gly Thr Gly Arg Gly Pro Thr Phe Glu Phe Tyr Thr Thr Val
        850                 855                 860

Ser His Glu Leu Gln Arg Val Gly Leu Gly Met Trp Arg Gly Asp Asp
865                 870                 875                 880

Thr Ser Gln Glu Cys Glu Ala Gly Phe Val His Ala Pro Phe Gly Leu
                885                 890                 895

Phe Pro Gln Pro Trp Ser Ser Ala Asn Thr Ser Ser Gly Ile Ser
                900                 905                 910

Leu Ser Asn Val Val Gln Lys Phe Lys Leu Leu Gly His Leu Val Ala
            915                 920                 925

Arg Ala Val Leu Asp Gly Arg Val Leu Asp Ile Pro Leu Ser Lys Ala
        930                 935                 940

Phe Tyr Lys Ile Met Leu Glu Gln Asp Leu Asp Ile Tyr Asp Ile Pro
945                 950                 955                 960

Ser Phe Asp Pro Lys Leu Gly Lys Thr Val Met Glu Phe Gln Ala Leu
                965                 970                 975

Val Lys Arg Lys Lys Phe Leu Glu Arg Ala Ser Asn Pro Ala Ala
                980                 985                 990

Asp Leu Ser Tyr Lys Asn Val Arg Leu Glu Asp Leu Cys Leu Asp Phe
        995                 1000                1005

Thr Leu Pro Gly Asn Pro Glu Tyr Glu Leu Val Pro Gly Gly Ser
    1010                1015                1020

Glu Lys Met Val Thr Leu Asp Asn Leu Glu Glu Tyr Val Ser Ser
    1025                1030                1035

Ile Val Asp Ala Thr Leu Lys Ser Gly Ile Ser Asn Gln Ile Glu
    1040                1045                1050

Ala Phe Lys Ala Gly Ile Asn Lys Val Phe Ala Leu Lys Thr Leu
    1055                1060                1065

Arg Leu Phe Ser Glu Asp Glu Met Glu Arg Ile Leu Cys Gly Glu
    1070                1075                1080

Gln Asp Ser Trp Ala Ser Asn Lys Leu Glu Asp His Ile Asn Phe
    1085                1090                1095

Asp Tyr Gly Tyr Asp Ala Asn Ser Ala Ser Val Ile Ser Phe Leu
    1100                1105                1110

Glu Ile Leu Arg Glu Phe Gly Arg Glu Asp Gln Arg Ala Phe Leu
    1115                1120                1125
```

-continued

| His | Phe 1130 | Thr | Thr | Gly | Ala | Pro 1135 | Gln | Leu | Pro | Leu 1140 | Gly | Gly | Leu | Ala |
| Ser 1145 | Leu | Asp | Pro | Lys | Leu | Thr 1150 | Val | Val | Arg | Lys 1155 | Gln | Cys | Asp | Gly |
| Lys | Val 1160 | Asp | Asn | Glu | Leu | Pro 1165 | Ser | Val | Asn | Thr 1170 | Cys | Arg | His | Phe |
| Phe | Lys 1175 | Leu | Pro | Pro | Tyr | Ser 1180 | Ser | Lys | Glu | Ile 1185 | Met | Arg | Gln | Lys |
| Leu | Lys 1190 | Tyr | Ala | Ile | Lys | Glu 1195 | Gly | Leu | Gly | Ser 1200 | Phe | Gln | Leu | Ser |